United States Patent [19]
Nyyssönen et al.

[11] Patent Number: 5,610,034
[45] Date of Patent: *Mar. 11, 1997

[54] IMMUNOGLOBULIN PRODUCTION BY TRICHODERMA

[75] Inventors: Eini Nyyssönen; Sirkka Keränen; Merja Penttilä, all of Helsinki; Kristiina Takkinen, Espoo; Jonathan K.C. Knowles, Helsinki, all of Finland

[73] Assignee: Alko Group Ltd., Helsinki, Finland

[*] Notice: The portion of the term of this patent subsequent to Dec. 28, 2020, has been disclaimed.

[21] Appl. No.: 756,251

[22] Filed: Aug. 30, 1991

Related U.S. Application Data

[63] Continuation-in-part of Ser. No. 552,757, Jul. 16, 1990, abandoned, which is a continuation-in-part of Ser. No. 496,155, Mar. 19, 1990, which is a continuation of Ser. No. 44,077, Apr. 29, 1987, abandoned.

[51] Int. Cl.$^6$ ............................ C12N 15/80; C12N 15/13
[52] U.S. Cl. .................... 435/69.6; 435/69.8; 435/172.3; 435/254.6; 435/320.1; 536/23.53; 536/24.1
[58] Field of Search ................................ 435/69.6, 69.8, 435/69.1, 172.3, 320.1, 254.6; 536/23.53, 24.1

[56] References Cited

U.S. PATENT DOCUMENTS

| | | | |
|---|---|---|---|
| 4,399,216 | 8/1983 | Axel et al. | 435/6 |
| 4,935,349 | 6/1990 | McKnight et al. | 435/69.5 |

FOREIGN PATENT DOCUMENTS

| | | |
|---|---|---|
| 125023 | 11/1984 | European Pat. Off. |
| 137280 | 4/1985 | European Pat. Off. |
| 173494 | 3/1986 | European Pat. Off. |
| 215594 | 3/1987 | European Pat. Off. |
| 222279 | 5/1987 | European Pat. Off. |
| 234592 | 9/1987 | European Pat. Off. |
| 244234 | 11/1987 | European Pat. Off. |
| 314161 | 5/1989 | European Pat. Off. |
| 2116567 | 9/1983 | United Kingdom |
| WO85/04672 | 10/1985 | WIPO |
| WO90/15860 | 12/1990 | WIPO |

OTHER PUBLICATIONS

Durand, H. et al., in *Biochem & Chem. of Cellulose Degradation*, Aubert et al., eds., Academic Press 1988, pp. 135–151.
Shoemaker, S. et al., *Bio/Technology* 1:691–696 (1983).
Teeri, T. et al., *Bio/Technology* 1:696–699 (1983).
Van Arsdell, J. N. V. et al., *Bio/Technology* 5:60–64 (1987).
Teeri, T. et al., *Gene* 51:43–52 (1987).
Chen, C. M. et al., *Bio/Technology* 5:274–278 (1987).
Saloheimo, M. et al., *Gene* 63:11–21 (1988).
Tilburn, J. et al., *Gene* 26:205–221 (1983).
Yelton, M. et al., *Proc. Natl. Acad. Sci. USA* 81:1470–1474 (1984).
Kelly, J. M. et al., *Embo J.* 4:475–479 (1985).
Gomi, K. et al., *Agric. Biol. Chem.* 51:2549–2555 (1987).
Better, M. et al., *Science* 240:1041–1043 (1988).
Harkki, A. et al., *Enzyme Microb. Technol.* 13:227–233 (1991).
Horwitz, A. H. et al., *Proc. Natl. Acad. Sci. USA* 85:8678–8682 (1988).
Penttilä, M. et al., *Gene* 61:155–164 (1987).
Nevalainen, H., Tech. Res. Centre of Finland, Publications 26 (1985), Espoo, Finland.
Morrison, S. L., "In Vitro Antibodies: Strategies for Production and Application," *Annu. Rev. Immunol.* 10:239–265 (1992).
Takkinen, K., et al., "An Active single–chain antibody containing a cellulase linker domain is secreted byu *Escherichia coli*," *Protein Eng.* 4(7):837–841 (1991).
Stangl, H. et al., "Characteriztion of the *Trichoderma reesei* cbh2 promoter," *Curr. Genet.* 23:115–122 (1991).
Nevalainen, K. M. et al., "The Molecular Biology of *Trichoderma* and Its Application to the Expression of Both Homologous and Heterologous Genes," In: *Molecular Industrial Mycology*, edited by Leong, S. A. et al., Marcel Dekker, Inc. pub., ch. 6, pp. 129–148 (1991).
Unkles, S. E., "Fungal biotechnology and the nitrate assimilation pathway," In: *Molecular and Genetic Aspects of Nitrate Assimilation*, eds. Wray, J. L. et al., ch. 22, pp. 341–363 (1989).
Berka, R. M. et al., "The Development Of Gene Expression Systems For Filamentous Fungi," *Biotech. Adv.* 7:127–154 (1988).
Wood, C. R. et al., *Nature* 314:446–449 (1985).
John, M. A. et al., *Enzyme Microb. Technol.* 6:386–389 (1984).
Harkki, A. et al., *Bio/Technol.* 7:596–603 (1989).

*Primary Examiner*—John L. LeGuyader
*Attorney, Agent, or Firm*—Sterne, Kessler, Goldstein and Fox, p.l.l.c.

[57] ABSTRACT

Methods for the production of recombinant immunoglobulins in a Trichoderma host are described.

48 Claims, 30 Drawing Sheets

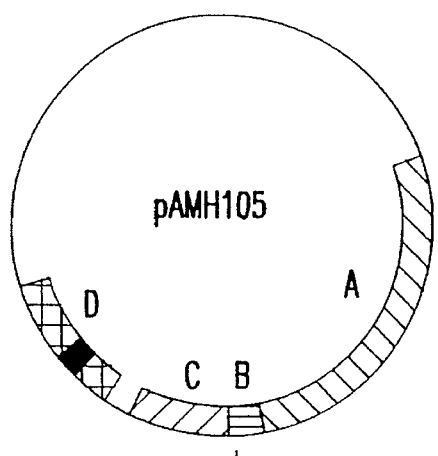

A = pcbh1 AREA (~2.4 kb)

B = ss OF cbh1

C = 5' END OF THE cbh1 GENE CODING FOR THE AMINO ACIDS 1-57

D = A 140 bp FRAGMENT FROM pR26 INCLUDING THE preproC 5' END UNTIL THE FIRST PstI SITE IN THE CODING REGION OF THE GENE, ■ = ss POLYLINKER OF pTZ19R
INCLUDING SacI-KpnI-XmaI/SmaI-BamHI-XbaI-SalI/AccI/HincII-PstI

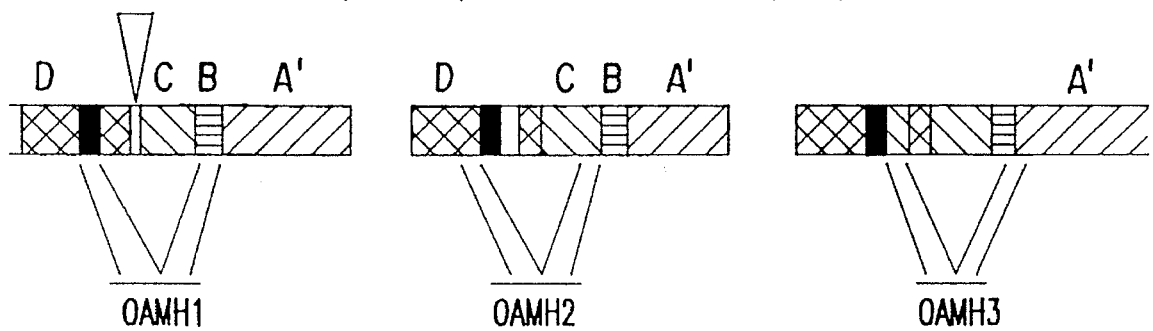

—ELONGATION WITH KLENOW AND LIGASE
—DIGESTION WITH SmaI (SmaI IN THE POLYLINKER)
—TRANSFORMATION I
—ISOLATION OF PLASMID DNA FROM THE POOL OF TRANSFORMANTS
—DIGESTION WITH SmaI
—TRANSFORMATION II
—THE SCREENING OF RIGHT CLONES
—SEQUENCING OF THE POTENTIAL RIGHT CLONES pAMH1103   pAMH1106   pAMH1101

FIG. 9

NOR 202

5'                           3'
TG'GCC'ACA'GCT'CGT'GC

NOR 203

5'                           3'
ACG'AGC'TGT'GGC'CAA'GA

OLIGO FOR MAKING A ss FUSION (Φ)

```
           3'                                              5'
OAMH1      TAG'AGC'CGG'AAG'AAC'CGA'GAG'AGG'GTC'CCG'
                                  ⌐⌐
           coding region of  ←──┘ └──→  coding region of
           aa 8-12 from CBHI ss          aa 12-16 from proC ss
```

OLIGO FOR MAKING A FUSION BETWEEN MATURE PROTEINS

```
           3'                                              5'
OAMH2      ACC'GTC'TTT'ACG'AGC'CCG'CGA'CTC'TAG'TGG'
                                  ⌐⌐
           coding region of  ←──┘ └──→  coding region of
           aa 16-20 from mature CBHI    aa 16-20 from preproC
```

OLIGO FOR JOINING THE PROMOTER OF cbh1 TO CHYMOSIN ss

```
           3'                                              5'
OAMH3      GCC'TGA'CCG'TAG'TAC'TCC'ACA'GAG'CAC'
                                  ⌐⌐
           12 ATG preceding ←──┘ └──→  coding region of
           bases from cbh1            5 first aa from preproC
           gene
```

FIG.10

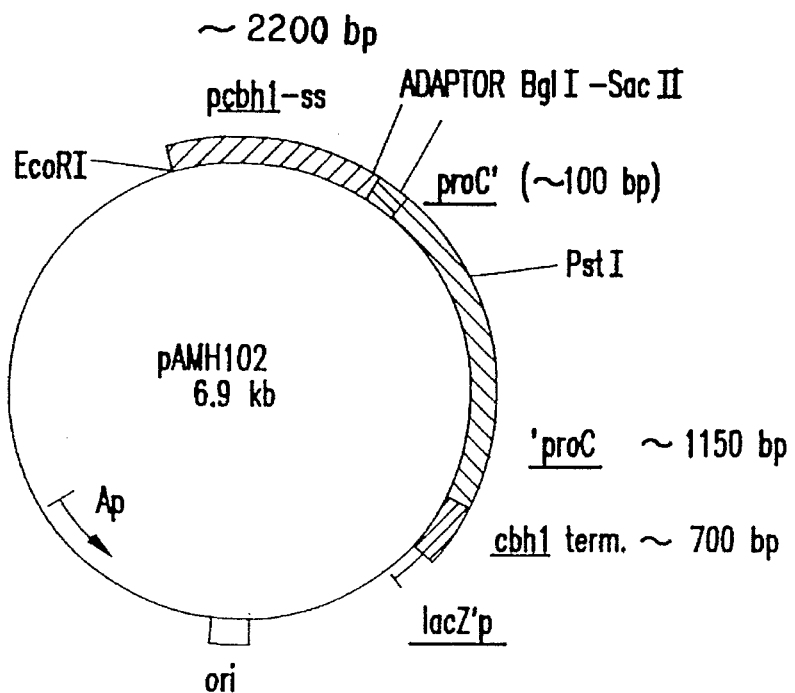
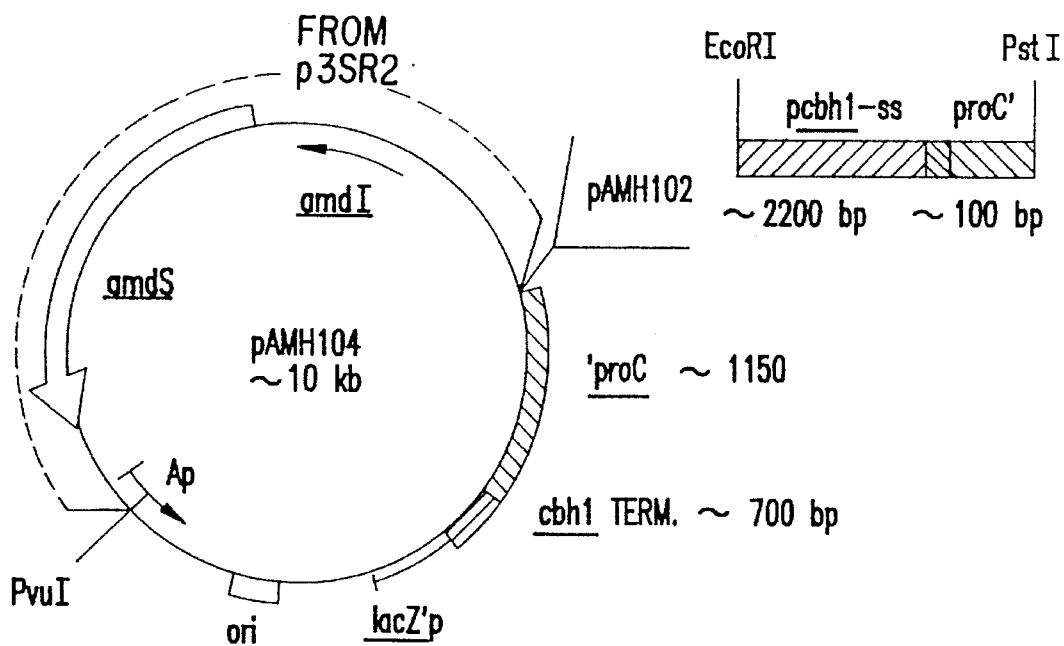
FIG.11

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

TGGCCACAGC TCGTGC                                                                16

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

ACGAGCTGTG GCCAAGA                                                               17

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

GCCCTGGGAG AGAGCCAAGA AGGCCGAGAT                                                 30

( 2 ) INFORMATION FOR SEQ ID NO:4:

( i ) SEQUENCE CHARACTERISTICS:
        ( A ) LENGTH: 30 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:4:

GGTGATCTCA GCGCCCGAGC ATTTCTGCCA 30

(2) INFORMATION FOR SEQ ID NO:5:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:5:

CACGAGACAC CTCATGATGC CAGTCCG 27

(2) INFORMATION FOR SEQ ID NO:6:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: CDS
(B) LOCATION: 1..36

(xi) SEQUENCE DESCRIPTION: SEQ ID NO:6:

| CCC | AGG | GAT | TGT | GGT | TGT | AAG | CCT | TGC | ATA | TGT | ACA | 36 |
| Pro | Arg | Asp | Cys | Gly | Cys | Lys | Pro | Cys | Ile | Cys | Thr | |
| 1 | | | | 5 | | | | | 10 | | | |

(2) INFORMATION FOR SEQ ID NO:7:

(i) SEQUENCE CHARACTERISTICS:
(A) LENGTH: 48 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: CDS
(B) LOCATION: 1..48

(xi) SEQUENCE DESCRIPTION: SEQ ID NO:7:

| CCC | AGG | GAT | TGT | GGT | GAC | ACA | GTG | ATC | AAG | AGG | AGG | AAA | TAA | CAT | ATG | 48 |
| Pro | Arg | Asp | Cys | Gly | Asp | Thr | Val | Ile | Lys | Arg | Arg | Lys | * | His | Met | |
| 1 | | | | 5 | | | | | 10 | | | | | 15 | | |

(2) INFORMATION FOR SEQ ID NO:8:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:8:

CAGCCCGGGCTG 12

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GGACTGGCAT CATGCAG 17

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

GATCCTGCAT GATGCCAGTCC GC 23

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

AATTCGGTAC CGCATGCGTC GACCTCGAG 29

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

AATTCTCGAG GTCGACGCAT GCGGTACCG 29

(2) INFORMATION FOR SEQ ID NO:13:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:13:

Pro Gly Gly Asn Arg Gly Thr Thr Thr Thr Arg Arg Pro Ala Thr Thr
1               5                   10                  15

Thr Gly Ser Ser Pro Gly Pro Thr Gln Ser His Tyr
            20                  25

(2) INFORMATION FOR SEQ ID NO:14:

(i) SEQUENCE CHARACTERISTICS:
  (A) LENGTH: 81 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:14:

```
TCATAGAGCT  CCCCGGGGGT  AACCGCGGTA  CCACCACTAC  CCGTGGTCCG  GCTACCACCA        60

CTGGCTCGAG  TCCAGGGCCC  A                                                    81
```

(2) INFORMATION FOR SEQ ID NO:15:

(i) SEQUENCE CHARACTERISTICS:
  (A) LENGTH: 45 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:15:

```
ATGTTTCTAG  AATAATGAGA  CTGGGTGGGC  CCTGGACTCG  AGCCA                        45
```

IMMUNOGLOBULIN PRODUCTION BY TRICHODERMA

CROSS-REFERENCE TO RELATED APPLICATIONS

This application is a Continuation-In-Part application of U.S. application Ser. No. 07/552,757, filed Jul. 16, 1990, now abandoned which is a Continuation-In-Part of U.S. application Ser. No. 07/496,155 filed Mar. 19, 1990, which is a continuation of U.S. application Ser. No. 07/044,077, filed Apr. 29, 1987, now abandoned.

FIELD OF THE INVENTION

The present invention is related to heterologous protein production by Trichoderma, and specifically to immunoglobulin production by Trichoderma. Methods for the production of such immunoglobulins by genetically engineering members of the species Trichoderma are disclosed. These preparations are especially useful for the treatment of medical conditions.

BACKGROUND OF THE INVENTION

I. Molecular Biology of Trichoderma

Filamentous fungi are lower eukaryotes widely used in biotechnology to make various fermentation products. Fungi secrete many industrially important enzymes such as glucoamylase, proteases, lactase, pectinases and glucose oxidase.

Filamentous fungi have a number of advantages for biotechnology. They generally produce high amounts of proteins, cultivation in large scale is not complicated and separation of the mycelium from the culture liquid after the fermentation is easy. For example, certain hypercellulolytic strains of the filamentous fungi Trichoderma are capable of secreting over 40 grams of cellulases per liter of culture medium (Durand, H. et al., in *Biochemistry and Genetics of Cellulase Degradation*, Academic Press, San Diego, 135–151 (1988); Durand, H. et al., *Enzyme Microbiol. Technology* 10:341–346 (1988)). In addition, there are indications that Trichoderma does not hyperglycosylate proteins as Saccharomyces yeast does (EP 215,594; Penttilä, M., *Construction and Characterization of Cellulolytic Yeasts*, VTT Publication Series No. 39, VTT Technical Research Center, Espoo, Finland, (1987)).

The mesophilic imperfect fungus *Trichoderma reesei* (now also known as *Trichoderma pseudokoningii* Rafai and formerly *T. viride*) (*Can. J. Bot.* 62:924; Simmons, E. G., In: *Abstracts of Second International Mycological Congress*, Tampa, Fla., Aigelow, H. E., et al., (eds.), p. 618 (1977)) produces substantial amounts of enzymes needed in the conversion of cellulosic biomass and is probably the most widely investigated of all cellulase-producing organisms.

For hydrolysis of cellulose to glucose, three types of enzyme activity are needed: randomly cleaving endoglucanases (1,4,-β-D-glucan glucanohydrolase, EC 3.2.1.4) which usually attack substituted soluble substrates and show no activity to crystalline cellulose; cellobiohydrolase (1,4-β-D-glucan cellobiohydrolase, EC 3.2.1.91) capable of degrading crystalline cellulose but having no activity towards derivatized cellulose and β-glucosidase (β-D-glucoside glycohydrolase, EC 3.2.1.21) attacking cellobiose and cello-oligosaccharides to yield glucose. Synergistic action between some of these enzymes has been demonstrated (Berghem, L. E. R., et al., *Eur. J. Biochem.* 97:21–30 (1973); Gong, C. S., et al., *Adv. Chem. Ser.* 181:261–287 (1979); Fägerstam, L. G., et al., *FEBS Letters* 119:97–100 (1980)).

Fungal cellulases have been purified and characterized and all three main types of enzymes have been shown to occur in multiple forms (Enari, T. M., In: Microbial Enzymes and Biotechnology, Fogarty, W. M. (ed.), Applied Science Publishers, London and New York, pp. 183–223 (1983)). Two immunologically distinctive cellobiohydrolases, CBH I and CBH II have been detected from the culture medium of *T. reesei* (Fägerstam, L. G., et al., *FEBS Letters* 119:97–100 (1980); Gilbert, I. G., et al., *Ann. Reports on Fermentation Processes* 6:323–358 (1983)). Five to eight electrophoretically distinct endoglucanases have been reported, many of them showing varying substrate specificities (Shoemaker, S. P., et al., *Biochim. Biophys. Acta* 523:133–146 (1978); Shoemaker, S. P., et al., *Biochim. Biophys. Acta* 523:147–161 (1978); Bissett, F. H., *J. Chromatog.* 178:517–523 (1979); Farkas, V. A., et al., *Biochem. Biophys. Acta* 706:105–110 (1982)). Characterization of two extracellular β-glucosidases has been reported (Enari, T. M., et al., In: *Proceedings of 2nd International Symposium on Bioconversion and Biochemical Engineering*, Ghose, T. K. (ed.), Indian Institute of Technology, New Delhi, 1:87–95 (1980)).

Intensive strain development using the direct approach of mutation and screening has successfully produced several high-yielding *T. reesei* mutant strains (Bailey, M. J., et al., *Enzyme Microb. Technol.* 3:153–157 (1981); Andreotti, R., et al., In: *Proceedings of 2nd International Symposium on Bioconversion and Biochemical Engineering*, Ghose, T. K. (ed.), Indian Institute of Technology, New Delhi, 1:353–388 (1980); Farkas, V., et al., *Folia Microbiol.* 26:129–132 (1981); Montenecourt, B. S., et al., *Adv. Chem. Ser.* 181:289–301 (1979); Mandels, M., et al., *Appl. Microbiol.* 21:152–154 (1971); Gallo, B. J., et al., *Biotechnol. Bioengineer. Symp.* 8:89–101 (1979); Warzywoda, M. et al., *Biotechnol. Lett* 5:243–246 (1983); Montenecourt, B. S., et al., *Appl. Environ. Microbiol.* 34:777–782 (1977); Sheir-Neiss, G., et al., *Appl. Microbiol. Biotechnol.* 20:46–53 (1984); Shoemaker, S. P., et al., In: *Trends in the Biology of Fermentations for Fuels and Chemicals*, Hollaender, A. E. (ed.), Plenum Press, pp. 89–109 (1981); Nevalainen, K. M. H., et al., *Enzyme Microb. Technol.* 2:59–60 (1980)). The amount of extracellular protein produced by the best *T. reesei* routants is more than 50% of the total cell protein. A major part of the secreted protein comprises cellulases among which the CBH I component is most abundant, representing up to 60% of the secreted cellulase proteins.

The gene for CBH I has been cloned by Shoemaker et al. (Shoemaker, S., et al., *Bio/Technology* 1:691–695 (1983)) and Teeri et al. (Teeri, T., et al., *Bio/Technology* 1:696–699 (1983)) and the entire nucleotide sequence of the gene has been published (Shoemaker, S., et al., *Bio/Technology* 1:691–696 (1983)). From *T. reesei*, the gene for the major endoglucanase EG I has also been cloned and characterized (Penttilä, M., et al., *Gene* 45:253–263 (1986); Patent Application EP 137,280; Van Arsdell, J. N. V., et al., *Bio/Technology* 5:60–64 (1987)). Other isolated cellulase genes are cbh2 (Teeri et al., *Gene* 51:43–52 (1987); Patent Application WO 85/04672; Chen, C. M., et al., *Bio/Technology* 5:274–278 (1987)) and egl2, previously called egl3 (Saloheimo, M., et al., *Gene* 63:11–21 (1988)).

The molecular biology of industrially important filamentous fungi is in general not well known. This is partly due to the lack of the sexual reproduction cycle and/or genetic transformation system. Transformation systems have been developed for a number of filamentous fungi, for example,

*Neurospora crassa* (Case, M., et al., *Proc. Natl. Acad. Sci. USA* 76:5259–5263 (1979)), *A. nidulans* (Ballance, J., et al., *Biochem. Biophys. Res. Commun.* 112:284–289 (1983); Tilburn, J., et al., *Gene* 26:205–221 (1983); Yelton, M., et al., *Proc. Natl. Acad. Sci. USA* 81:1470–1474 (1984)), and *A. niger* (Kelly, J. M., et al., *EMBO Journal* 4:475–479 (1985)), *A. oryzae* (Gomi, K. et al., *Agric. Biol. Chem.* 51:2549:2555 (1987) and Mattern, I. E. et al., *Mol. Gen. Genet.* 210:460–461 (1987) and *A. awamori* (Berka, R. M. et al., *Gene* 86:153–162 (1990) generally having their basis in complementation of the mutant host by respective functional gene carried by the vector molecule. However, of these fungi only *A. niger*, *A. awamori* and *A. oryzae* are of industrial interest at the moment.

In the classification of fungi, the genus Aspergillus is included in the class Ascomycetes, sub-class Euascomycetes. Euascomycetes are divided into three groups, Plectomycetes, Pyrenomycetes and Discomycetes on the basis of the fruiting bodies. The most important genera are Aspergillus and Penicillium (Doi, Y., *Bull. Nat. Sci. Mus. Tokyo* 11:185–189 (1968)). Trichoderma, instead, is classified as a member of Fungi imperfecti. Fungi imperfecti is a catch-all category of fungi which have no sexual reproduction or obvious affinities with sexually reproducing genera, such as the highly characteristic Aspergillus. Although Trichoderma has been reported to possess a poorly defined sexual stage being an imperfect state of the perfect ascomycete species Hypocrea (Beja da Costa, M., et al., *Biotechnol. Biogen.* 22:2429–2432 (1980)), the genera Aspergillus and Trichoderma are clearly to be considered taxonomically very different. It has also been shown that the argB gene from *Aspergillus nidulans* and the pyr4 gene from *Neurospora crassa* do not hybridize, under non-stringent conditions, to the respective Trichoderma genes, thus supporting the idea that Trichoderma is evolutionarily quite distinct from other Ascomycetes.

Due to its exceptional ability to secrete proteins into the growth medium *Trichoderma reesei* is a good candidate as a possible host for the production of proteins. However, genetic studies of *T. reesei* have so far been directed almost exclusively to improving the cellulose-producing properties of the fungus and the only technique used for the development of hypercellulotic Trichoderma strains has been traditional mutagenesis and screening.

In the fungal transformation systems first developed, namely for Aspergillus and Neurospora, transformation is carried out using protoplasts. The transforming DNA is usually integrated into the host genome. To provide a selection system for identifying stable transformants the vector system must carry a functional gene (a selection marker) which either complements a corresponding mutation of the host genome or supplies an activity, usually an enzyme, required for the growth of the prototrophic strain on a particular growth medium.

Durand et al., in *Biochemistry and Chemistry of Cellulose Degradation*, Aubert et al., eds., Academic Press, 1988, pp. 135–151 reported a transformation system for Trichoderma which was based on phleomycin resistance. However the transformants were unstable unless restreaked or kept on phleomycin plates for a long time (Berges, T. et al., in *Abstracts, Tricel 89, International Symposium on Trichoderma Cellulases*, Vienna, 1989, p.21, also reports a transformation system for Trichoderma). However, the Berges system also results in unstable transformants.

II. Immunoglobulins

Immunoglobulins consist of two identical light chains and two identical heavy chains linked by sulphur bridges. The polypeptide chains of immunoglobulins are formed from successive domains, which can fold up independently. Light chains consist of two domains, heavy chains usually four-five domains. The ability of immunoglobulins to recognize and specifically bind their antigens is due to differences in the variable domains which reside at the N-terminal ends of both the light and heavy chains.

An antibody molecule can be proteolysed into two parts, the so-called Fc and Fab fragments. The Fab fragment includes the sites from the variable domains of both the light and heavy chains which are responsible for the identification and binding of antigens.

The domains of the Fc fragment play roles in the activation of the immune response in a cell. Biochemical tests have shown that the Fc fragment is not necessary for antigen binding.

Through genetic engineering it is possible to produce just the Fab antigen-binding sites of antibodies (Better, M., et al., *Science*, 240:1041–1042 (1988); Cabilly, S., *Gene* 85:552–553 (1989). By combining independently folding domains of antibodies in various ways it has also been possible to produce chimeric antibodies (Morrison, S. L., EP 173,494; Cabilly, S., EP 125,023). It has, for example, been possible to combine human antibody domains with variable mouse antibody domains thus changing the antibody spectrum. Genetic engineering also allows the production of single-chain antibodies, in which an antigen-binding site is formed by only one polypeptide chain.

Monoclonal antibodies are produced in hybridoma and myeloma tissue cultures, often with human or mouse hybridoma cell lines. The methods are fairly expensive and the yields of monoclonal antibodies from human hybridoma cell lines are relatively low (1 µg/ml for human hybridomas compared to 100 µg/ml for mouse hybridomas).

In addition, most human monoclonal antibodies obtained in cell culture are of the IgM type. When it is desirable to obtain human monoclonals of the IgG type, it has been necessary to utilize cell sorting techniques to separate the few cells which have switched to producing antibodies of the IgG or other type from the majority producing antibodies of the IgM type. This greatly increases the expense and the yield of human IgG type monoclonal antibodies is even lower than that of the IgM type.

Efforts have been made to develop better methods, by transferring antibody genes into a host organism, such as the bacterium *Escherichia coli* (Better, M., et al., *Science*, 240:1041–1042 (1988)) and the yeast *Saccharomyces cerevisiae* (Horwitz, A. H., et al., *Proc. Natl. Acad. Sci. USA* 85:8678–8682 (1988). These have been used for the production of Fab sites. *E. coli* has also been used for the production of single chain antibodies. However, yield of the active product is still low, probably, for the most part, because of the naturally poor protein secretion capacity of the organisms. Thus, there remains a need for an economical manner in which to produce the amounts of immunoglobulins, and especially monoclonal antibodies needed for industrial and medical applications.

SUMMARY OF THE INVENTION

Recognizing the importance of immunoglobulin and especially monoclonal antibody applications in industry and medicine and cognizant of the high cost of producing antibodies in the quantities needed for such applications, the inventors have investigated the use of recombinant DNA techniques in the design of hosts which would be useful as a large-scale source of recombinantly produced immunoglobulins.

These studies have resulted in the development of fungal hosts which express large amounts of heterologous proteins, and especially immunoglobulins, immunoglobulin peptides, and biologically active portions of such immunoglobulins and immunoglobulin peptides.

The present invention describes a recombinant DNA cloning vector and vector system for the transformation of Trichoderma for the expression of such heterologous proteins, and especially for the expression of recombinantly produced immunoglobulins, immunoglobulin peptides, and biologically active portions of such immunoglobulins and immunoglobulin peptides. Transformation of Trichoderma with the present vector or vector system will provide a high level expression and secretion of the desired heterologous protein when the transformed microorganism is grown in a suitable culture medium.

According to its first aspect the present invention provides a vector, such vector comprising:

a) at least one gene encoding a desired expressible protein, or biologically active fragment thereof, and b) a selection marker capable of providing selection of Trichoderma hosts which have been transformed with such vector.

According to its second aspect, the present invention provides a vector system of one or more plasmids, such vector system comprising:

a) at least one gene encoding a desired protein product, or biologically active fragment thereof, and b) at least one selection marker capable of providing selection of Trichoderma hosts which have been transformed with such vector, such selection markers being provided to such Trichoderma host on a plasmid(s) which is not the same plasmid as that providing one or more genes encoding a desired protein product.

In a preferred embodiment of the first and second aspects of the present invention, the gene encoding a desired protein product or biologically active fragment thereof is a gene encoding an immunoglobulin or immunologically active fragment thereof.

In another embodiment of the first and second aspects of the present invention, the gene encoding a desired protein product or biologically active fragment thereof is flanked on its 5' end, and operably linked in reading phase to, a signal or leader sequence, such signal or leader sequence being is capable of directing secretion of such desired protein out of such Trichoderma host cell, such amino acid sequence being capable of cleavage from said desired protein or biologically active fragment thereof.

In another embodiment of the first and second aspects of the present invention, the gene encoding a desired protein product or biologically active fragment thereof is flanked, and operably linked to, (and, if necessary, in reading phase with,) one or more DNA regulatory elements selected from the group consisting of promoters, enhancers, signal/leader sequences, terminators, and combinations thereof, such DNA sequences being operably linked to such gene to control expression and/or secretion of the desired protein product.

In another embodiment of the first and second aspects of the present invention, the DNA regulatory sequences which are operably linked to the gene encoding a desired protein product or biologically active fragment thereof are DNA sequences homologous to Trichoderma genomic sequences.

In another embodiment of the first and second aspects of the present invention, the homologous DNA regulatory sequences which are operably linked to the gene encoding a desired protein product or biologically active fragment thereof are selected from the DNA regulatory regions of a gene expressed on glucose, the cbh1 gene, the cbh2 gene, the egl1 gene and the egl2 gene.

In another embodiment of the first and second aspects of the present invention, the selection marker capable of providing selection of Trichoderma hosts which have been transformed with such vector is selected from the group consisting of phleomycin resistance, amdS, trpC and argB selection.

According to its third aspect, the present invention provides a method for transformation of Trichoderma, wherein a suitable Trichoderma strain is transformed with the present vector or vector system.

According to its fourth aspect, the present invention provides a method for the production of a heterologous protein, in Trichoderma, such method comprising transforming Trichoderma with the present vector or vector system, culturing the transformed strain in a suitable medium and recovering the expressed and secreted product from the medium.

In a preferred embodiment of the fourth aspect, such heterologous protein is selected from the group consisting of an immunoglobulin, an immunoglobulin light chain, an immunoglobulin heavy chain, and immunologically active fragments of such immunoglobulin, immunoglobulin light chain, and immunoglobulin heavy chain.

According to its fifth aspect, the present invention provides a method for the production of an immunoglobulin, an immunoglobulin heavy chain, an immunoglobulin light chain, or biologically active fragments of such immunoglobulin or immunoglobulin heavy chain or immunoglobulin light chain, in Trichoderma, such method comprising transforming Trichoderma with the present vector or vector-system, culturing the transformed strain in a suitable medium and recovering the expressed and secreted immunoglobulin product from the medium.

In another embodiment of the fourth and fifth aspects of the invention such immunoglobulin, such immunoglobulin, immunoglobulin heavy chain, immunoglobulin light chain, or biologically active fragments of such immunoglobulin or immunoglobulin heavy chain or immunoglobulin light chain are reassociated in vitro with another immunoglobulin, an immunoglobulin heavy chain, an immunoglobulin light chain, or biologically active fragments of such immunoglobulin or immunoglobulin heavy chain or immunoglobulin light chain.

According to its sixth aspect, the present invention provides Trichoderma strains which have been stably transformed with a desired gene using the vector and vector systems of the invention.

According to its seventh aspect, the present invention provides fusion proteins

According to its eighth aspect, the present invention provides compositions which are enriched in such heterologous proteins, and especially in immunoglobulins, immunoglobulin heavy chains, immunoglobulin light chains, or biologically active fragments of such immnunoglobulins, immunoglobulin heavy chains and immunoglobulin light chains.

BRIEF DESCRIPTION OF THE DRAWINGS

Figures of the constructions are not to scale.

FIG. 9 shows the construction of plasmids pAMH1103, pAHM1106 and pAMH1101 by loop-mutagenesis using synthesized oligonucleotides OAMH1, OAMH2 and OAMH3.

FIG. 10 shows the linkers NOR 202, NOR 203, OAMH1, OAMH2 and OAMH3.

FIG. 11 shows the restriction maps of plasmids pAMH102 and pAMH104.

DETAILED DESCRIPTION OF THE INVENTION

I. Deposit Information

Figure 1:
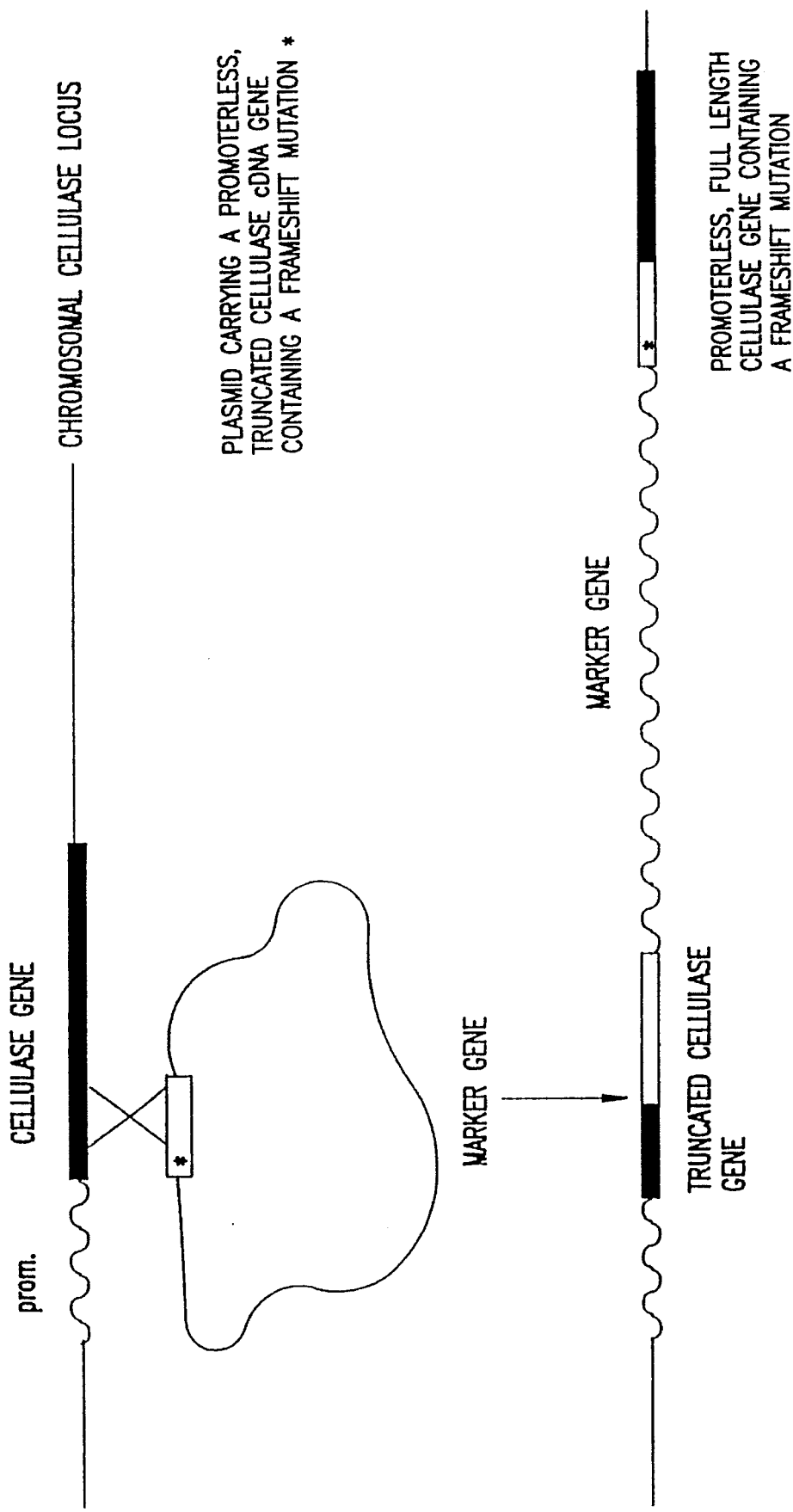
FIG. 1 shows the principle of the inactivation of a chromosomal cellulase gene.

The following deposits of biological material have been made in this matter at the Centraalbureau voor Schimmelcultures, P.O Box 273, Oosterstraat 1, 3740 AG Baarn, The Netherlands: light chain producing *T. reesei* strain pEN304/RUT-C-30) as accession No. CBS 252.90 (on Jun. 25, 1990); CBHI-IgG1 Fab fusion antibody producing *T. reesei* strain (pEN304/pEN209/RUT-C-30) as accession no. CBS 287.91 (on Jun. 3, 1991) and IgG1 Fab antibody producing *T. reesei* strain (pEN304/pAJ202/RUT-C-30) as accession no. CBS 288.91 (on Jun. 3, 1991). Deposits have also been made at Deutsche Sammlung von Mikroorganismen und Zellkulturen Gmbh (German Collection of Microorganisms and Cell Cultures), Mascheroder Weg 1b D-3300 Braunschweig, Germany; plasmid pAJ202 in *E. coli* as accession no. DSM 6584 (on Jun. 21, 1991); plasmid pEN209 in *E. coli* as accession no. DSM 6585 (on Jun. 21, 1991); plasmid pEN304 in *E. coli* as accession no. DSM 6586 (on Jun. 21, 1991); plasmid pEN401 in *E. coli* as accession no. DSM 6587 (on Jun. 21, 1991) and plasmid pEN402 in *E. coli* as accession no. DSM 6588 (on Jun. 21, 1991).

II. Definitions

In the description that follows, a number of terms used in recombinant DNA (rDNA) technology and immunology are extensively utilized. In order to provide a clear and consistent understanding of the specification and claims, including the scope to be given such terms, the following definitions are provided.

Gene

A DNA sequence containing a template for a RNA polymerase. RNA that codes for a protein is termed messenger RNA (mRNA) and, in eukaryotes, is transcribed by RNA polymerase II.

A "complementary DNA" or "cDNA" gene includes recombinant genes synthesized by reverse transcription of mRNA and from which intervening sequences (introns) have been removed.

By a protein homologous to a Trichoderma host of the invention is meant that an untransformed Trichoderma of the same species as the host species naturally produces some amount of the native protein; by a gene homologous to a Trichoderma host of the invention is meant a gene found in the genome of an untransformed Trichoderma of the same species as the host species.

By a protein heterologous to a Trichoderma host of the invention is meant that an untransformed Trichaderma of the same species as the host species does not naturally produce some amount of the native protein; by a gene heterologous to a Trichoderma host of the invention is meant a gene not found in the genome of an untransformed Trichaderma of the same species as the host species.

Cloning vehicle

A plasmid or phage DNA or other DNA sequence (such as a linear DNA) which provides an appropriate nucleic acid environment for the transfer of a gene of interest into a host cell. The cloning vehicles of the invention may be designed to replicate autonomously in prokaryotic and eukaryotic hosts. In Trichoderma, the cloning vehicles generally do not autonomously replicate and instead, merely provide a vehicle for the transport of the gene of interest into the Trichoderma host for subsequent insertion into the Trichoderma genome. The cloning vehicle may be further characterized by one or a small number of endonuclease recognition sites at which such DNA sequences may be cut in a determinable fashion without loss of an essential biological function of the vehicle, and into which DNA may be spliced in order to bring about replication and cloning of such DNA. The cloning vehicle may further contain a marker suitable for use in the identification of cells transformed with the cloning vehicle. The word "vector" is sometimes used for "cloning vehicle." Alternatively, such markers may be provided on a cloning vehicle which is separate from that supplying the gene of interest.

Expression vehicle

A vehicle or vector similar to a cloning vehicle but which is capable of expressing a gene of interest which has been cloned into it, after transformation into a desired host. In a preferred embodiment, such expression vehicle provides for an enhanced expression of a gene of interest which has been cloned into it, after transformation into a desired host.

In a preferred embodiment, the gene of interest which it is desired to express is provided to a fungal host as part of a cloning or expression vehicle and integrates into the fungal chromosome. Sequences which derive from the cloning vehicle or expression vehicle may also be integrated with the gene of interest during the integration process.

Expression vehicles also include plasmids or other vectors which carry a gene of interest, for example, a functionally complete constant heavy or light chain sequence, or a desired biologically active portion thereof, or a portion thereof, which, when reassociated with another peptide results in a biologically active protein product. Such genes of interest usually have appropriate restriction sites engineered so that any sequence with the appropriate cohesive ends can be easily inserted thereinto. Such vehicles can be used as intermediates for the expression of any desired protein in any appropriate Trichoderma host.

Immunoglobulin

The term "immunoglobulin" is meant to include proteins which possess immunological properties (such as antigen binding), for example, a multisubunit antibody containing two heavy chains and two lights chains. As used herein, the term also refers to a protein which contains the amino acid sequence of the individual light or heavy chain of such an antibody, such light or heavy chains being capable of being modified (for example, by reassociation with another immunoglobulin) to reveal their inherent immunological activity.

An "immunoglobulin gene" as used herein refers to a DNA sequence which encodes a single peptide such as an immunoglobulin heavy or light chain, a fragment thereof, or a single chain containing regions of such chains linked to each other.

Constant or Variable

The terms "constant" and "variable" are used functionally to denote those regions of the immunoglobulin chain, either heavy or light chain, which code for properties and features possessed by the variable and constant regions on natural antibodies. It is not necessary for the complete coding regions for variable or constant regions to be present, as long as a functionally operating regions is present and available.

Domain

The term "domain" is used to describe an independently folding part of a protein which may or may not function independently. General definitions for domain borders in natural proteins are found in Argos, P., *J. Mol. Biol.* 211:943–958 (1990).

Functional Derivative

A "functional derivative" of a protein is a smaller peptide of that protein, such peptide possessing a desired biological activity (either functional or structural), or modifiable in a known way to reveal such activity. For example, a functional derivative of an immunoglobulin heavy chain may be that fragment of the heavy chain which is found in the Fab fragment and which does not reveal its inherent activity until, with an appropriate functional derivative of a light chain, it is reassociated into an immunologically active Fab fragment. As used herein, a protein is said to be a "chemical derivative" of another protein when it contains additional chemical moieties not normally a part of the protein. Such moieties may improve the protein's solubility, absorption, biological half life, etc. The moieties may alternatively decrease the toxicity of the protein, eliminate or attenuate any undesirable side effect of the protein, etc. Moieties capable of mediating such effects are disclosed in *Remington's Pharmaceutical Sciences* (1980). Procedures for coupling such moieties to a protein are well known in the art.

A functional derivative of a protein may or may not contain post-translational modifications such as covalently linked carbohydrate, depending on the necessity of such modifications for the performance of a specific function. The term "functional derivative" is intended to include the "fragments," "variants," "analogues," or "chemical derivatives" of a molecule.

Fragment

A "fragment" of a protein is meant to refer to a peptide which possesses some but not all of the amino acid sequence of a longer protein.

As used herein, a protein is said to be an immunologically active fragment of a protein if such protein possesses a function found in a native immunoglobulin, or can be modified (for example, by reassociation with another immunoglobulin fragment) to reveal such function.

Variant

A "variant" of a protein is meant to refer to a protein substantially similar in structure and biological activity to a protein which is found in nature, or a fragment thereof, but which has been engineered to contain a different amino acid sequence. Thus, provided that two proteins possess a similar activity, they are considered variants as that term is used herein even if the primary structure of one of the protein does not possess the identical amino acid sequence to that found in the other.

III. Construction and Identification Of Antibodies

In the following description, reference will be made to various methodologies well-known to those skilled in the art of immunology. Standard reference works setting forth the general principles of immunology include the work of Catty, D. (*Antibodies, A Practical Approach*, Vol. 1, IRL Press, Washington, D.C. (1988)); Klein, J. (*Immunology: The Science of Self-Nonself Discrimination*, John Wiley & Sons, New York (1982)); Kennett, R., et al. (*Monoclonal Antibodies, Hybridoma: A New Dimension in Biological Analyses*, Plenum Press, New York (1980)); Campbell, A. ("Monoclonal Antibody Technology," In: *Laboratory Techniques in Biochemistry and Molecular Biology*, Volume 13 (Burdon, R., et al,, eds.), Elsevier, Amsterdam (1984)); and Eisen, H. N., (In: *Microbiology*, 3rd Ed, (Davis, B. D., et al., Harper & Row, Philadelphia (1980)), An antibody is said to be "capable of binding" a molecule if it is capable of specifically reacting with the molecule to thereby bind the molecule to the antibody. The term "epitope" is meant to refer to that portion of an antigen which can be recognized and bound by an antibody. An antigen may have one, or more than one epitope. An "antigen" is capable of inducing an animal to produce antibody capable of binding to an epitope of that antigen. The specific reaction referred to above is meant to indicate that the antigen will react, in a highly selective manner, with its corresponding antibody and not with the multitude of other antibodies which may be evoked by other antigens.

The term "immunoglobulin," "antibody" (Ab) or "monoclonal antibody" (Mab) as used herein is meant to include intact molecules as well as fragments thereof, peptides thereof, and biologically active fragments of such intact molecules and peptides, such as, for example, Fab and F(ab')$_2$ fragments which are capable of binding an antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

Because immunoglobulins usually contain two pairs of chains bound together by disulphide bridges, the term "immunoglobulin" is meant herein to encompass the individual immunoglobulin chains ("immunoglobulin peptides") even though such chains may require reassociation with a second immunoglobulin chain to reveal a biological activity inherent in their structure.

The immunoglobulins of the invention may be of any type (class) such as, for example, IgM, IgG, IgA, IgD and IgE as well as any of the various subtypes of the individual classes. The light chain may be either κ (kappa) or λ (lambda). The heavy chains may be μ (mu), γ (gamma), δ (delta), α (alpha) or ε (epsilon). In animals, different gene families encode the light and heavy chains. Biologically active portions of such chains, or domains from the various chains may be genetically recombined as desired.

Light and heavy chains are divided into domains of structural and functional homology. The variable regions of both light ($V_L$) and heavy ($V_H$) chains determine the immunoglobulin's recognition and specificity. The constant region domains of light ($C_L$) and heavy ($C_H$) chains confer important biological properties such as antibody chain association, secretion, transplacental mobility, complement binding, and the like.

A complex series of events leads to immunoglobulin gene expression in B cells. The V (variable) region gene sequences conferring antigen specificity and binding are located in separate germ line gene segments called $V_H$, D (diversity) and $J_H$ ("J" for joining); or $V_L$ and $J_L$. These gene segments are joined by DNA rearrangements to form the complete V regions expressed in heavy and light chains respectively. The rearranged, joined ($V_L$-$J_L$ and $V_H$-D-$J_H$) V segments then encode the complete variable regions or antigen binding domains of light and heavy chains, respectively.

A hybridoma source of a monoclonal antibodies which it is desired to clone and express according to the present invention is prepared by any of a variety of methods. Monoclonal antibodies can be prepared using hybridoma technology (Kohler et al., *Nature* 256:495 (1975); Kohler et *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., pp. 563–681 (1981)). In general, such procedures involve immunizing an animal with the desired protein. The splenocytes of such animals are extracted and fused with a suitable myeloma cell line. Any suitable myeloma cell line may be employed in accordance with the present invention; however, it is preferable to employ the parent myeloma cell line (SP$_2$O), available from the American Type Culture Collection, Rockville, Md. After fusion, the resulting hybridoma cells are selectively maintained in HAT medium, and then cloned by limiting dilution, for example, as described by Wands, J. R., et al., *Gastroenterology* 80:225–232 (1981), which reference is herein incorporated by reference. The hybridoma cells obtained through such a selection are then assayed to identify clones which secrete antibodies capable of binding the desired protein.

Through application of the above-described methods, additional cell lines capable of producing antibodies which recognize epitopes of a desired protein can be obtained.

A wide range of source hybridomas are immediately available for the preparation of the recombinant immunoglobulin constructs of the invention. For example, see the catalogue *ATCC Cell Lines and Hybridomas*, American Type Culture Collection, 12301 Parklawn Drive, Rockville, Md. 20852 U.S.A., and the ECACC Catalogue, 2nd edition, PHLS CAMR Porton Down, Salisbury, Wills, U.K. Hybridomas secreting monoclonal antibodies reactive to a wide variety of antigens are listed therein, are available from the collection, and usable in the invention. Of particular interest are hybridomas secreting antibodies which are reactive with viral antigens, bacterial antigens, and tumor antigens.

If polyclonal antibodies are desired, cells expressing a desired protein, or an antigenic fragment thereof, can be administered to an animal in order to induce the production of sera containing polyclonal antibodies that are capable of specifically binding the protein. In another method, a protein is isolated or a peptide fragment is chemically synthesized and purified by HPLC to render it substantially free of contaminants. Such a preparation is then introduced into an animal in order to produce polyclonal antisera of high specific activity. Such polyclonal antibodies may be especially useful in identifying clones which secrete a desired monoclonal antibody which is produced according to the methods of the invention.

IV. Trichoderma Hosts

The host strain may either be a prototrophic or an auxotrophic Trichoderma strain depending on the selection marker used in the transformation procedure. If a selection marker is used which complements a corresponding mutation of the host genome auxotrophic Trichoderma mutants must be constructed. Auxotrophic Trichoderma mutants may be produced by known methods for producing mutant strains.

Auxotrophic Trichoderma mutants requiring uracil, tryptophan or arginine for growth may be isolated by a filtration enrichment technique as described by Nevalainen (Nevalainen, H., Technical Research Center of Finland, Publication 26 (1985)). From arginine requiring auxotrophs, mutants deficient in the argB gene were identified by using a series of minimal plates supplied by different intermediates in the arginine biosynthesis.

Mutants having a trpC gene defect can be characterized by the lack of the PRA isomerase-InGP synthetase activity in their mycelia (Creighton, T. E., *Biochem. J.* 120:699–707 (1970)). The trpC-character of the mutants showing no enzyme activity may be confirmed by e.g. transformation and complementation with the trpC-plasmid of *A. nidulans* (Yelton, M., et al., *Proc. Natl. Acad. Sci. USA* 81:1470–1474 (1984)).

V. Design of the Recombinant Constructs

The process for genetically engineering the hosts of the invention is facilitated through the cloning of genetic sequences which are capable of encoding a desired protein and through the expression of such genetic sequences. As used herein, the term "genetic sequences" is intended to refer to a nucleic acid molecule (preferably DNA). Genetic sequences which are capable of encoding a desired protein are derived from a variety of sources. These sources include genomic DNA, cDNA, synthetic DNA, and combinations thereof, preferably from sources which naturally the desired protein.

Hybridoma cell lines which produce immunoglobulins and especially monoclonal antibodies of defined specificity are especially useful for the isolation of mRNA or genomic DNA for subsequence cloning of genes capable of expressing immunoglobulins according to the invention. Such mRNA or genomic DNA can be isolated by techniques known in the art, for example, as described in Maniatis, T. et al., *Molecular Cloning (A Laboratory Manual)*, Cold Spring Harbor Laboratory, 2nd edition, 1989.

A wide range of source hybridomas are available for the preparation of mRNA or genomic DNA. For example, see the catalogue *ATCC Cell Lines and Hybridomas*, American Type Culture Collection, 12301 Parklawn Drive, Rockville, Md. 20852 U.S.A., and the ECACC Catalogue, 2nd edition, PHLS CAMR Porton Down, Salisbury, Wills, U.K. Hybridomas secreting immunoglobulins and especially monoclonal antibodies reactive with a wide variety of antigens are listed therein, are available from the collection, and usable in the invention. Of particular interest are hybridomas secreting antibodies which are reactive with viral antigens, bacterial antigens, and tumor antigens.

The recombinant protein preparations according to this invention are produced by the fungus Trichoderma which has been modified by recombinant DNA techniques. The Trichoderma hosts of the invention are modified so as to express a natural or chimetic immunoglobulin. By "natural" immunoglobulin is meant an immunoglobulin whose coding sequence was originally formed as a result of genomic rearrangements in an animal cell. By a "chimetic" immunoglobulin is meant an immunoglobulin whose coding sequence was originally formed as a result of in vitro recombinant DNA techniques.

The Trichoderma hosts of the invention may be modified to produce an increased amount of one or more immunoglobulins and especially immunoglobulin chains. According to this invention, it is possible to enrich Trichoderma hosts for a desired immunoglobulin by inserting a gene encoding such immunoglobulin such that expression of the desired gene is operably linked to a promoter. In a preferred embodiment, the promoter is a strong homologous promoter. In a highly preferred embodiment, the desired gene is inserted into the cbh1 locus or a cassette comprising a desired gene already operably linked to the homologous cbh1 promoter is inserted into the cbh1 locus (U.S. application Ser. No. 07/524,308, incorporated herein by reference). In addition to cbh1, other homologous genes which can provide promoters and other transcriptional, translational, and secretion control signals useful in the expression vectors of the invention include, for example, the cellulase genes cbh2, egl1, egl2, previously called egl3 (which encode the proteins cellobiohydrolase I, cellobiohydrolase II, endoglucanase I and endoglucanase II) or combinations of these genes as genes expressed on glucose (Knowles, J. et al., *TIBTECH* 5:255–261 (1987)). An example of a promoter derived from a gene for a protein heterologous to Trichoderma is the Aspergillus glucoamylase promoter, and the Aspergillus amdS, gpd, argB promoters (Penttilä, M. et al., *Gene* 61:155–164 (1987) and trpC promoters. Synthetic promoters may be constructed containing regulatory regions derived from two or more different natural promoters.

Eliminating the activity of any of the cellulase genes will result in a host which is partially or completely deficient in its ability to degrade cellulose to glucose.

Such cellulase deficient strains can be obtained, for example, by transformation of Trichoderma with a plasmid containing only part of the homologous coding region (insertional activation). This is described in EP 244,234. Alternatively, cellulase deficient strains can also be prepared by gene replacement strategy in which the 5' and 3' flanking DNA is utilized to obtain homologous recombination. In between the flanking regions, a marker gene or gene coding for the desired protein product can be placed. *T. reesei* strains deficient in different cellulase enzymes can be identified by using, for example, an ELISA test which uses antibodies, and especially monoclonal antibodies, against the different cellulases to characterize the presence or absence of a specific cellulase (U.S. application Ser. No. 07/524,308).

Integration of a desired gene with homologous recombination may be done with a circular DNA, which integrates in a col inear manner into the Trichoderma chromosomal DNA. However, the use of a linear DNA especially helps in directing integration into a homologous locus. In a highly preferred embodiment, the integration of a desired gene is directed into the Trichoderma cbh1 locus.

Clones of the cellulase enzymes which may be used to provide a source of homologous transcriptional and translational regulatory sequences for the hosts of the invention are known in the art. For example, the gene for the native cellobiohydrolase CBH I sequence has been cloned by Shoemaker et al. (Shoemaker, S., et al., *Bio/Technology* 1:691–695 (1983)) and Teeri et al. (Teeri, T., et al., *Bio/Technology* 1:696–699 (1983)) and the entire nucleotide sequence of the gene is known (Shoemaker, S., et al., *Bio/Technology* 1:691–695 (1983)). From *T. reesei*, the gene for the major endoglucanase (EG I) has also been cloned and characterized (Penttilä, M., et al., *Gene* 45:253–263 (1986); Patent Application EP 137,280; Van Arsdell, J. N. V., et al., *Bio/Technology* 5:60–64 (1987)). Other isolated cellulase genes are cbh2 (Teeri et al., *Gene* 51:43–52 (1987); Patent Application WO 85/04672; Chen, C. M., et al., *Bio/Technology* 5:274–278 (1987)) and egl2 previously called egl3 (Saloheimo, M., et al., *Gene* 63:11–21 (1988)).

According to this invention, the genetic constructs which encode a desired protein, such as a desired immunoglobulin, and especially an immunoglobulin chain may be introduced into the genome of Trichoderma. Enhanced expression can also be achieved by using strong promoters such as cbh1 and, if desired, additional or modified regulatory regions, such as, for example, enhancer sequences may be used. Preferably, such regulatory sequences are homologous to Trichoderma. A regulatory region, and especially a promoter, may be modified to contain only those sequence elements needed for expression and/or to retain a region which is responsible for high expression levels. Enhancer sequences may be introduced concurrently with the gene of interest as a separate DNA element but operably-linked to such gene of interest, for example, as a DNA sequence which is colinear with that providing the gene of interest (for example, in a 5' or 3' non-translating sequence, or in an intron).

In a highly preferred embodiment, according to this invention increased amounts of a desired protein are achieved by introducing the gene producing such desired protein into a specific locus and/or introducing the gene in multicopies into the genome of Trichoderma as described above.

In another embodiment, a gene encoding a desired protein can also be integrated into the genome of Trichoderma by using a vector which provides cloning sites allowing insertion of a gene of interest into an expression cassette in a manner which operably links the gene of interest to a promoter and terminator sequence. Preferably, the cbh1 gene promoter and terminator are used. The cassette may further provide a stuffer fragment between the promoter and terminator sequences which can be removed. For example, a general expression vector such as pAMH110, which is described in the patent application EP 244,234 may be used. pAMH110 is derived from pUC19 (Yanisch-Perron et al., Gene 33:103–119 (1985)). The stuffer fragment in pAMH110 may be removed by digestion with SacII and NdeI. After the ends of a double-stranded DNA sequence which encodes a desired protein are made blunt, any DNA, cDNA or chromosomal DNA can be inserted between the promoter and terminator. The desired gene can be inserted to the cbh1 expression cassette in the plasmid pAMH110 between the cbh1 promoter and terminator.

Transcriptional regulatory elements of other genes may be used where it is desired not to use the cbh1 elements. For example a vector construction comprising the 3-phosphoglycerate kinase gene (pgk) transcriptional regulatory regions may be used as 3-phosphoglycerate kinase, a key enzyme for ATP generation by glycolysis, is expressed in the presence of glucose under which conditions the synthesis of cellulases is repressed.

While the inventors do not intend to be bound by any particular theory, the effectiveness of the expression of the desired gene seems to be dependent both on the number of copies of the desired gene integrated to the genome of Trichoderma and on the location of integration of the gene in the genome.

The DNA constructions prepared according to this invention can be used to transform any Trichoderma strain. Such strains include, for example, T. reesei strains QM9414 (ATCC 26921), RUT-C-30 (ATCC 56765), and highly productive mutants like VTT-D-79125, which is a descendant of QM9414 (Nevalainen 1985, Technical Research Centre of Finland Publications 26, (1985), Espoo, Finland). The transformation of Trichoderma may be performed by any technique known in the art and especially by the technique taught in U.S. application Ser. No. 07/044,077, filed Apr. 29, 1987.

The Trichoderma host cells may be cultivated and the desired enzymes produced by cultivating the host strain having the desired properties under any conditions which allow expressing of the desired enzymes. For example, a Trichoderma host strain having the desired properties may be cultivated in a liquid cultivation medium, which may comprise, for example, 6% Solka Floc cellulose, 3% distiller's spent grain, 0.5% $KH_2PO_4$, 0.5% $(NH_4)_2SO_4$, 0.1% struktol. If a desired recombinant gone is placed under the control of the cbh1 promoter in Trichoderma it will be sensitive to glucose repression and require an inducer such as, for example, cellulose, lactose or sophorose (Allen et al., Biotechnology and Bioengineering 33:650–656 (1989)). The pH in Trichoderma cultivation should be kept at approximately pH 5 by the addition of phosphoric acid or ammonia and the temperature may be kept at 30° C. during the cultivation. However, the temperature and pH should be adjusted according to the strain and according to the protein to be produced (Merivuori et al., Biotechnology Lett. 12:117–120 (1990)).

Vector systems may be used in the method of producing the recombinant proteins, and especially the immunoglobulins of the invention. Such vector systems may be constructed so as to provide (a) on a first vector, agene which encodes at least one desired gene, for example, agene encoding an immunoglobulin chain or immunologically active fragment thereof, to be integrated to the genome of Trichoderma and (b) on a second vector, another gene which encodes at least one desired gene, for example, a gene encoding another immunoglobulin chain or immunologically active fragment thereof, to be integrated to the genome of Trichoderma; and (c) a selectable marker which provides selection of Trichoderma which contain (a) and/or (b). Alternatively, a selectable marker may be provided on a separate vector.

In another embodiment, two cassettes encoding two different genes of interest are provided at different sites on the same vector.

The cloned DNA which is used in the hosts of the invention may or may not include naturally occurring introns. Moreover, such genomic DNA may be obtained in association with the native 5' promoter region of the DNA genetic sequences and/or with the 3' transcriptional termination region if such sequences are capable of functioning in Trichoderma. Further, such genomic DNA may be obtained in association with the genetic sequences which encode the 5' non-translated region of the mRNA and/or with the genetic sequences which encode the 3' non-translated region. To the extent that the Trichoderma host cell can recognize the transcriptional and/or translational regulatory signals associated with the expression of the mRNA and protein, then the 5' and/or 3' non-transcribed regions of the native gene, and/or, the 5' and/or 3' non-translated regions of the mRNA, may be retained and employed for transcriptional and translational regulation. Genomic DNA can be extracted by means well known in the art (for example, see Guide to Molecular Cloning Techniques, S. L. Berger et al., eds., Academic Press (1987)). Alternatively, mRNA can be isolated from any cell which produces or expresses the desired protein, and used to produce cDNA by means well known in the art (for example, see Guide to Molecular Cloning Techniques, S. L. Berger et al., eds., Academic Press (1987)). Preferably, the mRNA preparation used will be enriched in mRNA coding for a desired protein, either naturally, by isolation from a cells which are producing large amounts of the protein, or in vitro, by techniques commonly used to enrich mRNA preparations for specific sequences, such as sucrose gradient centrifugation, or both.

For cloning into a vector, such suitable DNA preparations (either genomic DNA or cDNA) are randomly sheared or enzymatically cleaved, respectively, and ligated into appropriate vectors to form a recombinant gene (either genomic or cDNA) library.

A DNA sequence encoding a desired protein may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis et al., Molecular Cloning (A Laboratory Manual), Cold Spring Harbor Laboratory, 1982), and are well known in the art.

Libraries containing clones encoding a desired protein, such as an immunoglobulin chain and especially a chain of a monoclonal antibody, may be screened and a clone to the desired protein identified by any means which specifically selects for that protein's DNA such as, for example, a) by hybridization with an appropriate nucleic acid probe(s) containing a sequence specific for the DNA of this protein, or b) by hybridization-selected translational analysis in which native mRNA which hybridizes to the clone in question is translated in vitro and the translation products are further characterized, or, c) if the cloned genetic sequences are themselves capable of expressing mRNA, by immunoprecipitation of a translated protein product produced by the host containing the clone.

Oligonucleotide probes specific for the desired protein which can be used to identify clones to such protein can be designed from knowledge of the amino acid sequence of the protein and if desired, obtained commercially.

Because the genetic code is degenerate, more than one codon may be used to encode a particular amino acid (Watson, J. D., In: *Molecular Biology of the Gene*, 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code (Watson, J. D., In: *Molecular Biology of the Gene*, 3rd Ed., W. A. Benjamin, Inc., Menlo Park, Calif. (1977)), one or more different oligonucleotides can be identified from the amino acid sequence, each of which would be capable of encoding the protein. The probability that a particular oligonucleotide will, in fact, constitute the actual protein's sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:1–12 (1985). Using the "codon usage rules" of Lathe, a single oligonucleotide sequence, or a set of oligonucleotide sequences, that contain a theoretical "most probable" nucleotide sequence capable of encoding the protein's sequence is identified.

The suitable oligonucleotide, or set of oligonucleotides, which is capable of encoding a fragment of the protein's gene (or which is complementary to such an oligonucleotide, or set of oligonucleotides) may be synthesized by means well known in the art (see, for example, *Synthesis and Application of DNA and RNA*, S. A. Narang, ed., 1987, Academic Press, San Diego, Calif.) and employed as a probe to identify and isolate the desired cloned gene by techniques known in the art. Techniques of nucleic acid hybridization and clone identification are disclosed by Maniatis, T., et al. (In: *Molecular Cloning, A Laboratory Manual*, Cold Spring Harbor Laboratories, Cold Spring Harbor, N.Y. (1982)), and by Hames, B. D., et al. (In: *Nucleic Acid Hybridization, A Practical Approach*, IRL Press, Washington, D.C. (1985)). Those members of the above-described gene library which are found to be capable of such hybridization are then analyzed to determine the extent and nature of the desired genomic coding sequences which they contain.

To facilitate the detection of the desired DNA encoding sequence, the above-described DNA probe is labeled with a detectable group. Such detectable group can be any material having a detectable physical or chemical property. Such materials have been well-developed in the field of nucleic acid hybridization and in general most any label useful in such methods can be applied to the present invention. Particularly useful are radioactive labels, such as $32_P$, $3_H$, $14_C$, $35_S$, $125_I$, or the like. Any radioactive label may be employed which provides for an adequate signal and has a sufficient half-life. The oligonucleotide may be radioactively labeled, for example, by "nick-translation" by well-known means, as described in, for example, Rigby, P. J. W., et al., *J. Mol. Biol.* 113:237 (1977) and by T4 DNA polymerase replacement synthesis as described in, for example, Deen, K. C., et al., *Anal. Biochem.* 135:456 (1983).

Alternatively, polynucleotides are also useful as nucleic acid hybridization probes when labeled with a non-radioactive marker such as biotin, an enzyme or a fluorescent group. See, for example, Leary, J. J., et al., *Proc. Natl. Acad. Sci. USA* 80:4045 (1983); Renz, M., et al., *Nucl. Acids Res.* 12:3435 (1984); and Renz, M., *EMBO J.* 6:817 (1983).

Thus, in summary, the actual identification of protein's sequence (or a partial sequence of the protein) permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing the protein's gene.

In an alternative way of cloning a gene, a library is prepared using an expression vector, by cloning DNA or, more preferably cDNA prepared from a cell capable of expressing a desired protein, into an expression vector. The library is then screened for members which express the protein, for example, by screening the library with antibodies to the protein, and especially, in this case, antibodies which recognize a desired immunoglobulin or fragment thereof.

The above discussed methods are, therefore, capable of identifying genetic sequences which are capable of encoding a desired immunoglobulin or fragments of this protein. In order to further characterize such genetic sequences, and, in order to produce the recombinant immunoglobulin, it is desirable to express the protein which this sequence encodes. Such expression identifies those clones which express proteins possessing characteristics of the desired protein, and especially, the desired immunoglobulin. Such characteristics may include the ability to specifically bind antibodies directed against the protein, the ability to elicit the production of antibody which are capable of binding the protein, and the ability to provide a function specific to the protein, among others.

The cloned protein encoding sequences, obtained through the methods described above, and preferably in a double-stranded form, may be operably linked to sequences controlling transcriptional expression in an expression vector, and introduced into a Trichoderma host cell to produce recombinant protein or a functional derivative thereof.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a protein encoding sequence and a promoter region sequence linked to the 5' end of the encoding sequence) are said to be operably linked if induction of promoter function results in the transcription of the protein encoding sequence mRNA and if the nature of the linkage between the two DNA sequences does not (1) result in the introduction of a frame-shift mutation, (2) interfere with the ability of the expression regulatory sequences to direct the expression of the mRNA or protein, or (3) interfere with the ability of the template to be transcribed by the promoter region sequence. Thus, a promoter region would be operably linked to a DNA sequence if the promoter were capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively.

Expression of the protein in the Trichoderma hosts requires the use of regulatory regions functional in such hosts. A wide variety of transcriptional and translational regulatory sequences can be employed, since Trichoderma generally recognize transcriptional controls, such as, for example, those of other filamentous fungi. In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell.

As is widely known, translation of eukaryotic mRNA is initiated at the codon which encodes the first methionine. For this reason, it is preferable to ensure that the linkage between a eukaryotic promoter and a DNA sequence which encodes the protein, or a functional derivative thereof, does not contain any intervening codons which are capable of encoding a methionine. The presence of such codons results either in a formation of a fusion protein (if the AUG codon is in the same reading frame as the protein encoding DNA sequence) or a frame-shift mutation (if the AUG codon is not in the same reading frame as the protein encoding sequence).

The secretion of the expressed product the gene for the desired product is preferably provided with a preregion ensuring effective direction of the expressed product into the secretory pathway of the cell. In a preferred embodiment, a desired protein is secreted into the surrounding medium due to the presence of a homologous Trichoderma secretion signal sequence.

Such preregion may provide the signal sequence of an immunoglobulin molecule or may provide a signal sequence of a different protein. There are many heterologous signal sequences which can be used. The preregion might be naturally occurring signal or leader peptide or parts thereof or a synthetic signal/leader sequence, especially a synthetic sequence containing codons preferred in the desired host. The preregion is generally cleaved off from the desired product during secretion whereupon the mature product can be isolated from the culture medium. The signal/leader sequence may be derived from the signal/leader sequence of the gene encoding the desired protein or may be derived from genes for other secreted proteins either from Trichoderma or from any other source of organism. Examples of signal/leader sequences derived from genes encoding a protein secreted by Trichoderma are cbh1 signal sequence or the egl1 signal sequence or parts thereof. Signal/leader sequences derived from genes encoding secreted proteins heterologous to Trichoderma may be derived from genes for Aspergillus amylases or glucoamylase. The desired coding sequence of a protein may be linked to any signal sequence which will allow secretion of the protein from a Trichoderma host, for example, a yeast sequence (Wood, C. R., et al., *Nature* 314:446–449 (1985); Kaiser, C. A. *Science* 235:312–317 (1987)).

Transcriptional initiation regulatory signals can be selected which allow for repression or activation, so that expression of the operably linked genes can be modulated. Of interest are regulatory signals which are temperature-sensitive so that by varying the temperature, expression can be repressed or initiated, or are subject to chemical regulation, e.g., substrate or metabolite regulation.

If desired, the non-transcribed and/or non-translated regions 3' to the sequence coding for a protein can be obtained by the above-described cloning methods. The 3'-non-transcribed region may be retained for its transcriptional termination regulatory sequence elements; the 3-non-translated region may be retained for its translational termination regulatory sequence elements, or for those elements which direct polyadenylation in eukaryotic cells.

In a preferred embodiment, genetically stable transformants of Trichoderma are constructed whereby a desired monoclonal antibody's DNA is integrated into the host chromosome. The coding sequence for the desired monoclonal antibody may be from any source. Such integration may occur de novo within the cell or, in a most preferred embodiment, be assisted by transformation with a vector which functionally inserts itself into the host chromosome, for example, DNA elements which promote integration of DNA sequences in chromosomes.

Cells which have stably integrated the introduced DNA into their chromosomes are selected by also introducing one or more markers which allow for selection of host cells which contain the expression vector in the chromosome. The selectable marker gene can either be directly linked to the DNA gene sequences to be expressed, or introduced into the same cell by co-transfection. Different selection markers may be used, e.g., argB (*A. nidulans* or *T. reesei*), and amdS (*A. nidulans*). In a preferred embodiment, a dominant selection marker is used such as amdS (Kelly, J. M. et al., *EMBO J.* 4:475–479 (1985); Tiburn, J. et al., *Gene* 26:205–221 (1983)) or a phleomycin resistance gene (Mattern, I. E., et al., in *Abstracts of the 19th Lunteren Lectures on Molecular Genetics of Yeasts and Filamentous Fungi and its Impact on Biotechology*, Lunteren, the Netherlands, p.34 (1987)). Auxotrophic selection markers are also available, for example, trpC or argB (Penttilä, M. et al., *Gene* 61:155–164 (1987)). If a desired monoclonal antibody is expressed from two different expression cassettes on two different plasmids (one cassette expressing the light chain and one cassette expressing the heavy chain), it may be desired to utilize two different selection markers to ensure that the host has been transformed with both plasmids.

*T. reesei* grows poorly on acetamide as the sole nitrogen source and the growth can be further inhibited by adding CsCl to the medium. The growth on acetamide as the sole nitrogen source in the presence of CsCl can accordingly be used as a selection medium to identify AmdS$^+$ transformants.

Factors of importance in selecting a particular plasmid include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Once the vector or DNA sequence containing the construct(s) is prepared for expression, the DNA construct(s) is introduced into an appropriate host cell by any of a variety of suitable means, including transformation as described above. After the introduction of the vector, recipient cells are grown in a selective medium, which selects for the growth of transformed cells. Expression of the cloned gene sequence(s) results in the production of the desired protein, or in the production of a fragment of this protein. This expression can take place in a continuous manner in the transformed cells, or in a controlled manner.

The methods described herein can be used to switch the class of any antibody of a given specificity and class to an antibody of the same specificity but of a different class, whether human or non-human. Various types of immunoglobulin molecules may be provided including divalent, dispecific (i.e., with different variable regions), molecules with chimeric heavy chains and non-chimeric light chains, or molecules with variable binding domains attached to peptide moieties carrying desired functions.

Antibodies having chimeric heavy chains of the same or different variable regions binding specificity, and non-chimeric (i.e. all human or all non-human) light chains, can be prepared by appropriate association of the needed polypeptide chains. These chains can be prepared by using two Trichoderma immunoglobulin-expressing clones of the invention (one expressing the heavy chain and one expressing the light chain) or by using one clone which expresses both of the desired chains. The light and heavy chains of such monoclonal antibodies may be allowed to associate in the Trichoderma host cell or may be combined in vitro, by allowing the disulfide bridges which characterize the chain association of such antibodies to form. Methods of reassociating a light chain and a heavy chain so as to form a functional immunoglobulin molecule are known in the art (Boss, M. A. et al., *Nucl. Acids Research* 12:3791–3806 (1984); Cabilly, S. et al., *Proc. Natl. Acad. Sci. USA* 81:3273–3277 (1984)).

Class switching is useful when it is desired to change the association, aggregation or other properties of antibodies obtained from cell fusion or hybridoma technology.

In order for a Trichoderma host cell to produce an intact functional immunoglobulin molecule, a balanced synthesis of both light and heavy chain protein within the host cell is preferred. One approach is to place the light and heavy chain genes on separate cassettes on separate vectors, preferably with the same promoter being used to drive the expression of both chains. Alternatively, if different promoters are used, they should be balanced such that one promoter is not so much stronger or weaker than the other promoter that a disproportionate synthesis of one chain over the other chain occurs.

Efficient secretion of the immunoglobulin chains can be achieved by constructing fusion proteins, where either one or both immunoglobulin chains are preceded by an amino acid sequence which functions as secretion signal in Trichoderma. In a preferred embodiment, such amino acid sequence is derived from an efficiently secreted Trichoderma protein or parts of such protein. Efficiently secreted cellulases of Trichoderma are well suited for fusion constructions. After secretion, the Trichoderma protein part of the fusion could be removed, for example, by adding or otherwise engineering a proteolytic cleavage site between the two protein sequences.

It is understood and obvious to the expert in the art that all specifically mentioned DNA-sequences may be modified by amendment or deletion of a couple of bases non-essential to the encoded product or encoded function. For example, DNA sequences substantially similar to cbh1 or egl1 signal or promoter sequences may be used as long as they exhibit the intended function in Trichoderma. Also the genes for the desired proteins may be altered as long as this has no deleterious effect on the activity of the protein.

VI. Transformation of the Trichoderma Hosts

Any method of transforming Trichoderma with the constructs of the invention may be used. In a preferred embodiment, the transformation technique is adapted from the methods for transformation of A. nidulans (Ballance, J., et al., *Biochem. Biophys. Res. Commun.* 112:284–289 (1983); Tilburn, J., et al., *Gene* 26:205–221 (1983)). This is described in Penttilä, M. et al., *Gene* 61:155–161 (1987). Protoplasts are prepared by known methods by growing mycelium on agar plates and suspending mycelium in a buffered solution of Novozym$^R$ 234. Instead of the conventional sucrose solution of Novozym$^R$ 234 a sorbitol solution may advantageously be used. Transforming DNA is then added to the protoplast solution as described in further detail in the experimental part of the specification. The transformation is usually carried out as a cotransformation by which a nonselectable plasmid is cotransformed into T. reesei with high frequency using a selectable marker inserted in another plasmid (e.g., amdS in p$_3$SR$_2$ or argB in pSal43). A great proportion of the transformants contain the nonselectable plasmid integrated into the genome if equimolar amounts of DNA are used for transformation. When an argB$^+$ T. reesei strain is used in transformation with equimolar amounts of plasmids p3SR2 and pSal43, transformants can be obtained on double selection medium (minimal medium, acetamide, CsCl). Alternatively, a single plasmid may be used for transformation in which also the selectable marker is inserted.

Transformants are then cultured in a suitable medium. To be able to produce the desired product in a simple defined medium a glucose inducible gene (or the glucose inducible promoter thereof) may be used. When Trichoderma is grown on a medium containing 2% glucose, secretion of all extracellular proteins, including proteases is strongly suppressed. When the gene coding for the desired protein, for example, an immunoglobulin, is connected to a promoter strongly expressed in glucose containing medium, the desired protein is preferably secreted to the growth medium. Since other proteins are not produced under these conditions, the desired protein is the major protein secreted into the medium.

When the fungal mycelium is removed from such a culture, the desired protein is present in the resulting solution in a very pure form. If required, such protein can be very easily further purified, since it is almost the only protein present.

The use of solid media permits rapid screening of thousands of colonies arising from transformed Trichoderma conidia for the presence or absence of specific proteins and allows quantitative estimation of the amount of such proteins produced. Several types of solid media for detection of such proteins are known in the art.

Many fungi form large diffuse colonies when grown on solid media. Addition of chemical agents restrictive to colony growth may therefore be desired to allow development of more than one (up to 100) colony per one plate. Among agents used for the purpose are rose bengal, oxgall and phosphon D, Triton X-100 and saponin. With some fungi, replica plating technique analogous to that developed for bacteria can, in certain cases, be used to test the properties of fungal colonies on different growth media.

Screening on plates is usually followed by cultivation of the selected colonies in shake flasks in a liquid production medium for measurement of protein production. Trichoderma is well adapted to fermenter cultivations and can utilize cheap raw materials for growth. The best isolates showing enhanced recombinant protein production in shake flask scale may be utilized in a second round of transformation if it is desired to express more than one recombinant protein in a host. Alternatively, a desired Trichoderma host may be cotransformed with more than one gene of interest at the same time.

VII. The Immunocilobulin Preparation

To obtain the proteins, and especially the immunoglobulins of the invention, the recombinant hosts described above having the desired properties are cultivated under suitable conditions. The desired proteins are secreted from the Trichoderma hosts and into the culture medium, and the proteins are recovered from said culture medium by methods known in the art.

The protein preparation can be produced by cultivating the Trichoderma strain in a fermentor having the desired properties for example in a liquid cultivation medium, which may comprise for example 6% Solka Floc cellulose (BW40, James River Corporation, Hackensack, N.J.), 3% distiller's spent grain (waste after alcohol distillation, ALKO, Ltd., Koskenkorva, Finland), 0.5% $KH_2PO_4$, 0.5% $(NH_4)_2SO_4$, and 0.1% struktol as an antifoaming agent (struktol SB 2023, Schill & Seilacher, Hamburg, FRG). If expression of the recombinant protein is under the direction of the cbh1 promoter, the Trichoderma strain will be sensitive to glucose repression and expression of such protein will require an inducer (cellulose, lactose or sophorose) (Allen et al., *Biotechnology and Bioengineering* 33:650–656 (1989)). The pH should preferably be kept at approximately pH 5 by the addition of phosphoric acid or ammonia and the temperature at 30° C. during the cultivation. However, the temperature and pH may be adjusted according to the strain and according to the protein to be produced (Merivuori et al., *Biotechnology Letters* 12(2):117–120 (1990)).

The recombinant protein preparation is recovered from the culture medium by using methods well known in the art. If the hosts of the invention are partially or completely deficient in cellulase activity or if the product is produced by a promoter which functions in the presence of glucose, the recombinant protein may be pure enough to be utilized directly from the culture medium with no further purification. If desired, such preparations may be lyophilized or the immunological activity otherwise concentrated and/or stabilized for storage. The recombinant protein preparations of the invention are very economical to provide and use because the proteins are secreted into the culture medium, only the culture medium need be recovered to obtain the desired protein preparation; there is no need to extract such protein from the Trichoderma hosts.

If desired, an expressed protein may be further purified in accordance with conventional conditions, such as extraction, precipitation, chromatography, affinity chromatography, electrophoresis, or the like.

VIII. The Pharmaceutical Composition

The proteins of the invention may be conjugated, either chemically or by genetic engineering, to fragments of other agents which provide a targeting of such proteins to a desired site of action. Alternatively, other compounds may be conjugated, either chemically or by genetic engineering, to the recombinant protein or active fragment thereof, so as to enhance or provide additional properties to such protein, especially properties which enhance the protein's function, or its ability to treat or alleviate an undesired condition or physiological state.

Amounts and regimens for the administration of the proteins, and especially immunoglobulins of the invention can be determined readily by those with ordinary skill in the clinical or industrial art. Generally, the amount of protein and especially immunoglobulin will vary depending upon considerations such as: type of application, type of monoclonal antibody employed; age, health, conditions of a patient being treated; kind of concurrent treatment, if any, frequency of treatment and the nature of the effect desired; counterindications, if any, and other variables to be adjusted by the individual physician or scientist.

Dosage can be administered in one or more applications to obtain the desired results. The recombinant protein of the invention can be administered in any appropriate agricultural or pharmacological carrier for administration. The recombinant protein can be administered in any form that effects prophylactic, palliative, preventative or curing conditions of a desired condition, or in any form which retains a desired function, for example, the immunological function of an immunoglobulin preparation.

Preparations of the recombinant proteins of the invention for parenteral administration includes sterile aqueous or non-aqueous solvents, suspensions and emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles include fluid and nutrient replenishers, electrolyte replenishers, such as those based upon Ringer's dextrose and the like.

The recombinant proteins of the invention may also be administered by means of pumps, sprays, and in sustained-release form, especially, when it is desired to prolong the effect of a given application or dose. The proteins of the invention may also be delivered to specific organs in high concentration by means of suitably inserted catheters, or by providing such molecules as a part of a chimeric molecule (or complex) which is designed to target specific organs.

Administration in a sustained-release form is more convenient for a patient when repeated injections for prolonged periods of time are indicated. For example, it is desirable to administer the recombinant proteins, and especially the immunoglobulins of the invention in a sustained-release form when the methods of the invention are being used to treat a genetic or chronic disease, such as a tumor or neoplastic state, so as to maximize the comfort of the patient.

The recombinant proteins of the invention can be employed in dosage forms such as tablets, capsules, powder packets, or liquid solutions for oral administration if the biological activity of the protein is not destroyed by the digestive process and if the characteristics of the compound allow it to be absorbed across the intestinal tissue.

Pharmaceutical compositions providing the recombinant proteins of the present invention are manufactured in a manner which is in itself known, for example, by means of conventional mixing, granulating, dragee-making, dissolving, lyophilizing or similar processes. The compositions of the present invention, in and of themselves, find utility in the diagnosis and control of many physiological and agricultural conditions, in the industrial treatment of wastes, sewage, and in the industrial preparation of biologicals, among other uses.

In intravenous dosage form, the compositions of the present invention have a sufficiently rapid onset of action to be useful in the acute management of a physiological condition needing immediate amelioration.

Additionally, a low potency version is useful in the management of mild or chronic physiological disorders.

Such compositions are conveniently provided in kit form, such kits containing appropriate buffers and mixing solutions for use of the recombinant proteins in a given application. For example, the compositions of the present invention may provide requisite reagents for diagnostic kits or for the laboratory assay of any antigen recognized by the recombinant proteins of the invention.

IX. Summary—Advantages of the Invention

Trichoderma is an especially useful and practical host for the synthesis of recombinant proteins and especially for the synthesis of immunoglobulins because Trichoderma is capable of secreting large amounts of protein, for example, concentrations as much as 40 g/L culture fluid have been reported; the homologous Trichoderma cbh1 promoter provides a very convenient promoter for expression of a desired gene because it is a strong, single copy promoter which normally directs the synthesis of up to 60% of the secreted protein from the Trichoderma host; the transformation system is highly versatile and can be adapted for any gene of interest; the Trichoderma host provides an "animal cell type" high mannose glycosylation pattern; and culture of Trichoderma is supported by previous extensive experience in industrial scale fermentation techniques.

Proteins, and especially immunoglobulins and their derivatives produced by the methods of the invention have applications in, for example, the agricultural, foodstuffs and pharmaceutical industries. Applications of immunoglobulins include their use as immunotoxins, and as immunological contrast media for the location of tumors, milk processing, large-scale purification of enzymes, purification of stereospecific drug substances and other molecules, purification of sewage and the development of sensitive and specific biosensors.

The invention is described in more detail in the following examples, These examples show only a few concrete applications of the invention. It is self evident for one skilled in the art to create several similar applications. Hence the examples should not be interpreted to narrow the scope of the invention only to clarify the use of the invention.

EXAMPLES

Materials

Figure 26A:
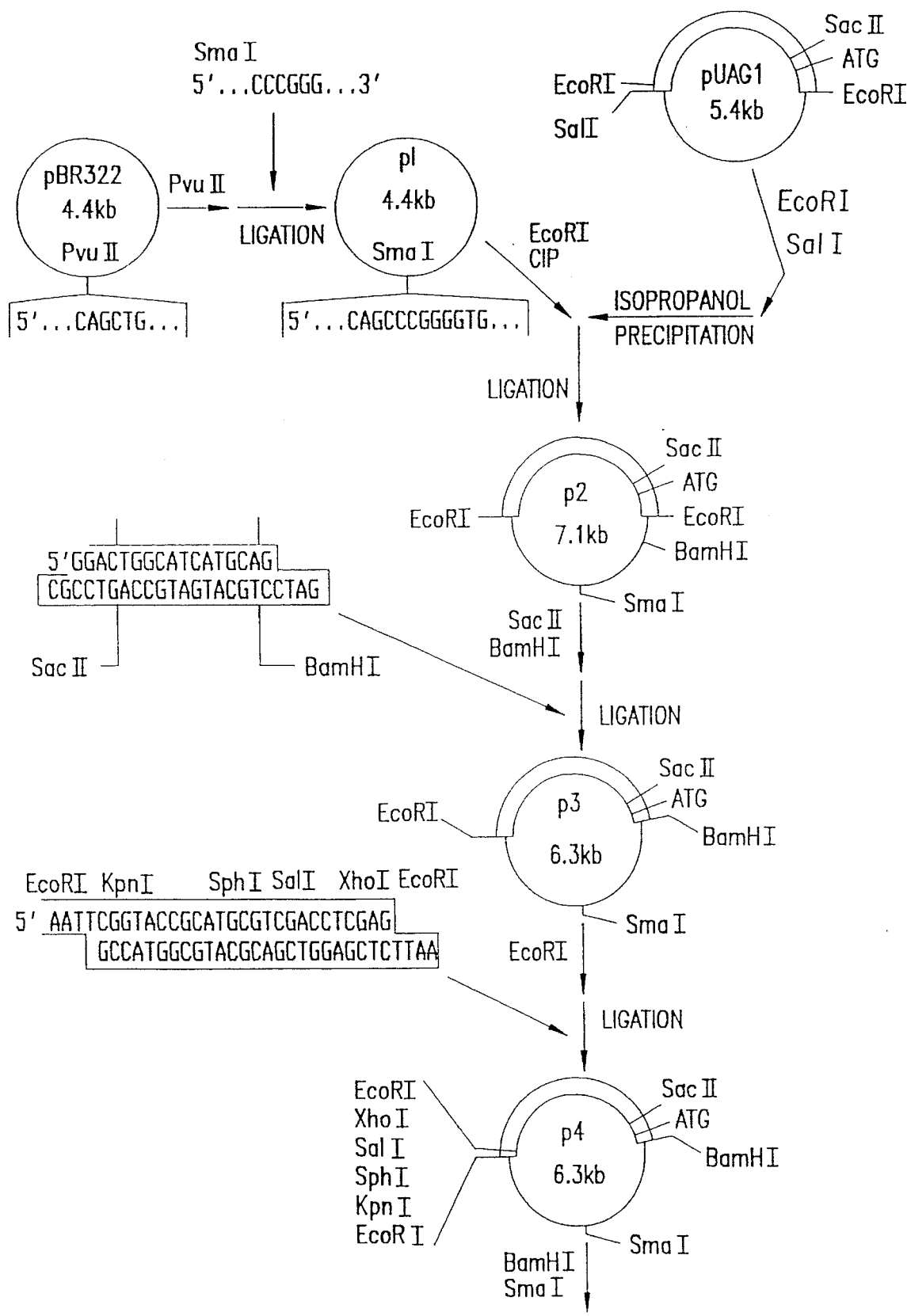
FIG. 26 diagrams the construction of plasmid pUJ10.
Figure 26B:
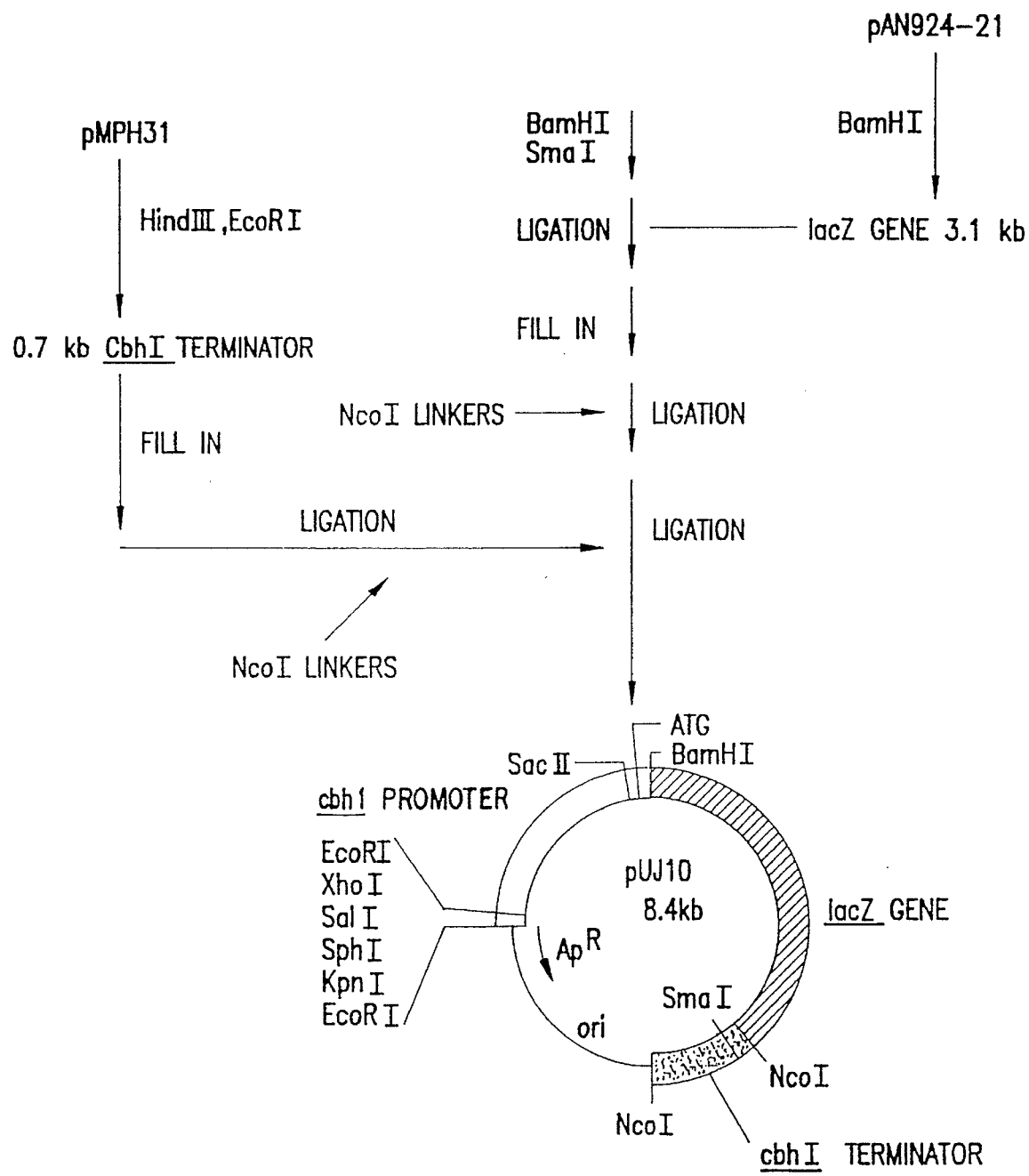
Figure 27:
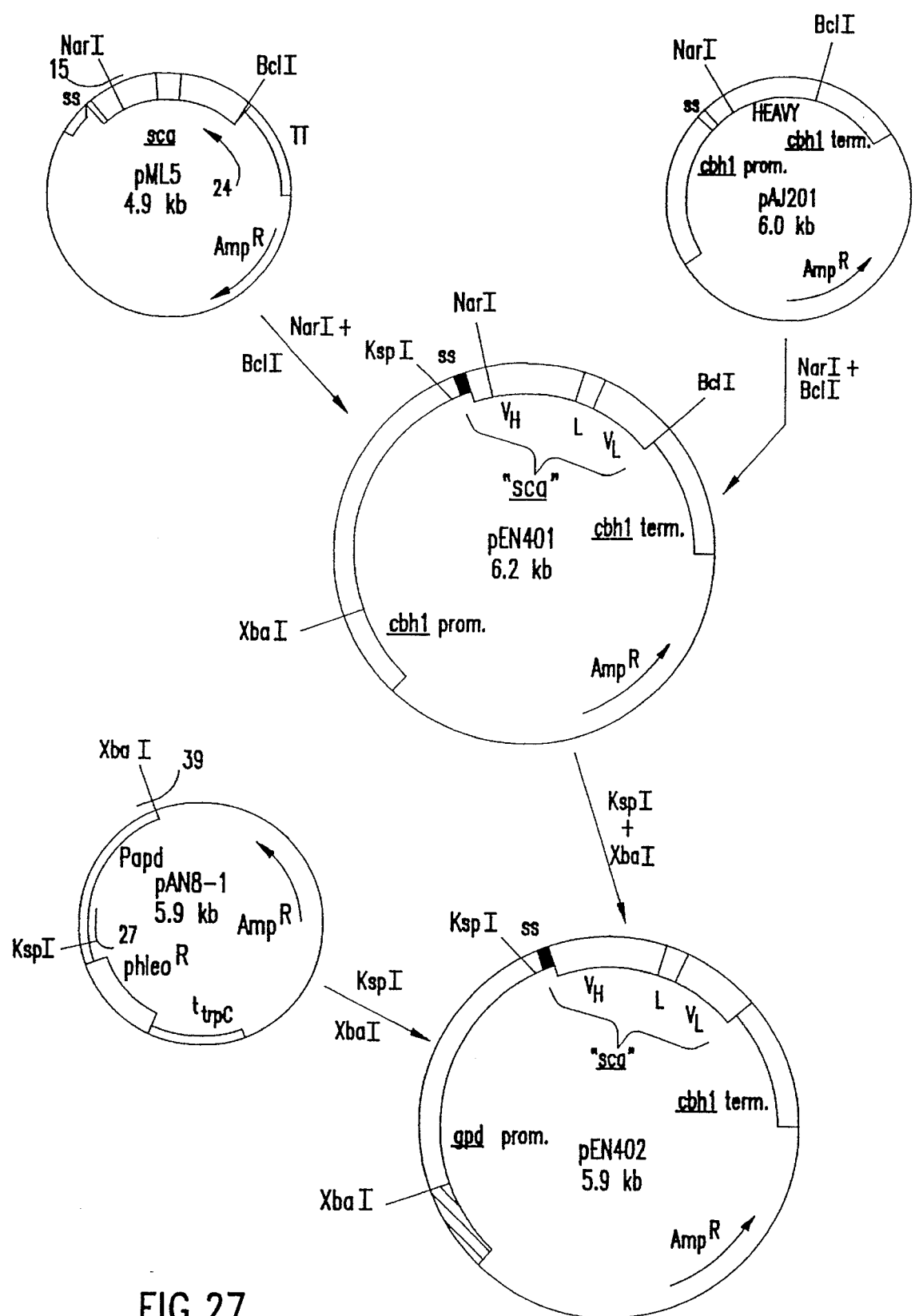
FIG. 27 shows the construction of plasmids pEN401 and pEN402.
Figure 28:
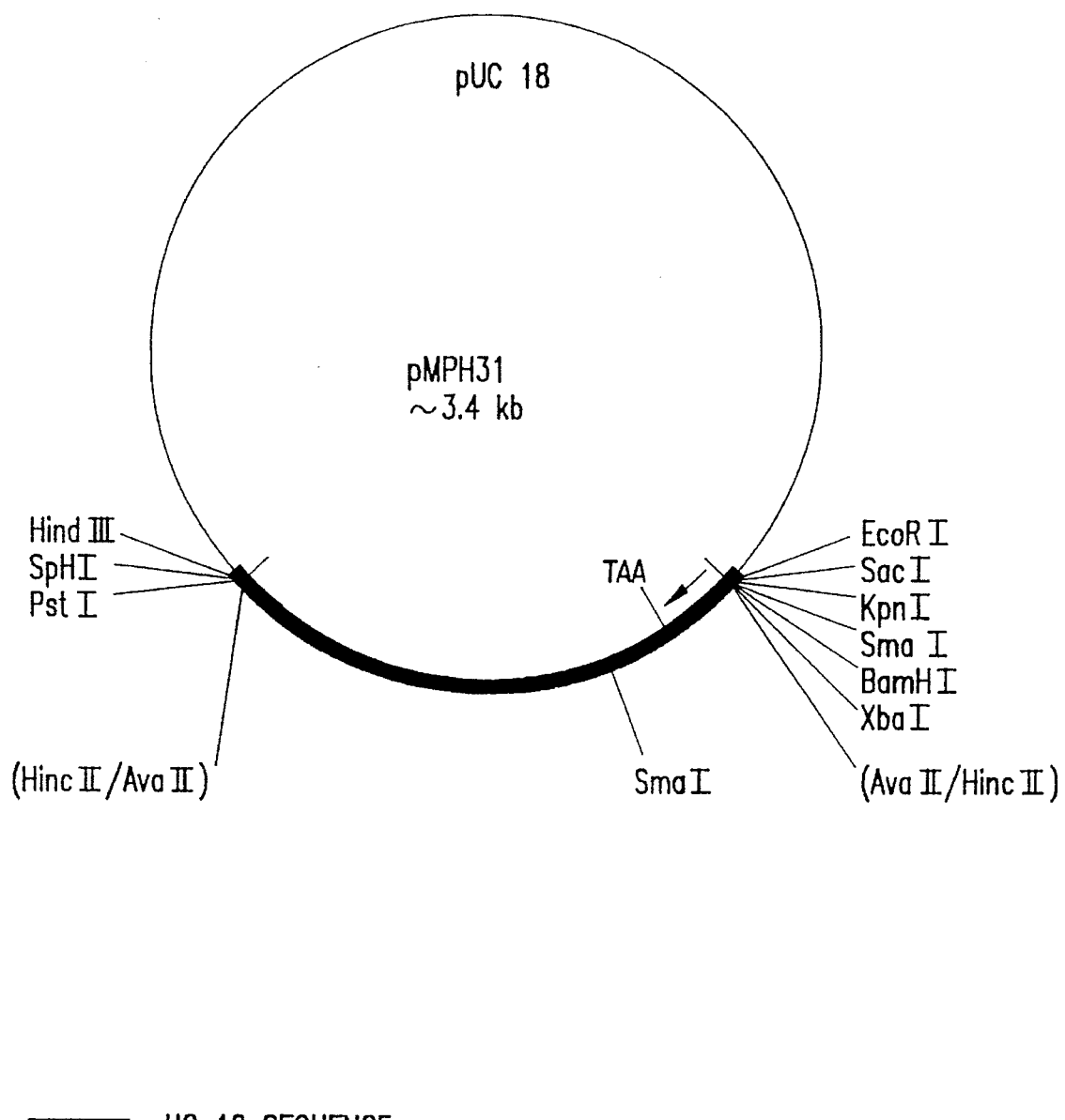
FIG. 28 shows the construction of plasmid pMPH31.

Plasmids
1. p285 is ATCC No. 20681.
2. pCAMG91 is described in Boel, E., etal., *The EMBO Journal* 3:1581–1585 (1984).
3. piCl9R is described in Marsh, J. L., etal., *Gene* 32:481–485 (1984).
4. pSal43 is described in John, M. A., etal., *Enzyme Microb. Technol.* 6:386–389 (1984); Berse, B., et al., *Gene* 25:109–117 (1983).
5. p3SR2 is described in Tilburn, J., et al., *Gene* 26:205–221 (1983); Kelly, J. M., etal., *EMBO Journal* 4:475–479 (1985).
6. pDJB2 is described in Ballanco, D. J., etal., *Gene* 36:321–331 (1985).
7. pMC1871 is described in Casadaban, M. J., et al., *Methods Enzymol.* 100B:293–308 (1983).
8. pTT01 and pTT11 are described in Patent Application WO 85/04672.
9. pUC9 and pUC13 are described in Vieira, J., et al., *Gene* 19:259–268 (1982).
10. pUC18 and pUC19 are described in Yanisch-Perron, C., et al., *Gene* 33:103–119 (1985).
11. pTZ18R and pTZ19R are available from Pharmacia.
12. pAN5-41B is described in Van Gorcom, R. F. M., et al., *Gene* 48:211–217 (1986).
13. pAN8-1 is described in Mattern, I. E., Punt, P. J., Unkles, S. Pouwels, P. H. and van den Hondel, C. A. M. J. J., Transformation of *Aspergillus oryzae*. In: *Abstracts of the 19th Lunteren Lectures on Molecular Genetics of Yeasts and Filamentous Fungi and its Impact on Biotechnology.* Lunteren, The Netherlands (1987), 34.
14. pAMH102 is described in Harkki, A., Uusitalo J., Bailey, M., Penttilä, M. & Knowles, J. K. C., A novel fungal expression system: secretion of active calf chymosin from the filamentous fungus *Trichoderma reesei. Bio/Technology* 7(1989), 596–603.
15. pAMH111 is described in Harkki, A, Mätylä, A, Penttilä, M., Muttilainen, S., Buhler, R., Suominen P., Knowles, J. & Nevalainen, H., Genetic engineering of *Trichoderma* to produce strains with novel cellulase profiles. *Enzyme Microb. Technol.* 13:227–233 (1991).
16. p3SR2 is described in Kelly, J. M. & Hynes, M. J., Transformation of *Aspergillus niger* by amdS gene of *Aspergillus niger EMBO Journal* 4 (1985): 475–479=1 ; Tilburn, J., Schazzocchio, C., Taylor, G. T., Zabjckyzissman, J. H., Lockington, R. A & Davies, R. W., Transformation by integration in *Aspergillus nidulans. Gene* 26 (1983), 205–221.
17. pUA01 from FIG. 26 is also drawn in FIG. 8 and described in example 9.IV.
18. pAN924–21 in FIG. 26 is described in van Gorcom, R. F. M., Pouwels, P. H., Goosen, T., Visser, J., van den Broek, H. W. J., Hamer, J. E., Timberlake, W. E. & van den Hondel, C. A. M. J. J., *Expression of an Escherichia coli β- galactosidase fusion gene in Aspergillus nidulans.* Gene 40:99–106 (1985).
19. pML5 is described in Takkinen, K., Laukkanen, M-L., Sizmann, D., Alfthan, K., Immonen, T., Vanne, L., Kaartinen, M., Knowles, J. K. C., and Teeri, T. T., *An active single chain antibody containing a cellulase linker domain is secreted by Escherichia coli. Protein Engineering,* 4:837–841 (1991).

Host Strains

*E. coli* strains JM101, JM103, JM109 and DH1 (Yanisch-Perron, C. et al., *Gene* 33:103–119 (1980)) and DH5α (BRL) are used as hosts in *E. coli* cloning. *Trichoderma reesei* strains QM9414 (ATCC 26921) and *Trichoderma reesei* strain RUT-C-30 (ATCC 56765) (Montenecourt, B. S. & Eveleigh, D. E., Selective screening methods for isolation of high yielding cellulase mutants of *Trichoderma reesei. Adv. Chem. Ser.* (1979), 289–301) are used in fungal transformation and expression studies.

| Trichoderma minimal medium: | |
|---|---|
| Glucose | 20 g/l |
| $(NH_4)_2SO_4$ | 5 g/l |
| $KH_2PO_4$ | 15 g/l |
| $MgSO_4$ | 0.6 g/l |
| $CaCl_2$ | 0.6 g/l |
| $FeSO_4 \times 7 H_2O$ | 5 mg/l |
| $MnSO_4 \times H_2O$ | 1.56 mg/l |
| $ZnSO_4 \times 7 H_2O$ | 1.4 mg/l |
| $CoCl_2$ | 2 mg/l |

The aim of the study was to produce immunoglobulin molecules in different forms in *Trichoderma reesei*. For this particular study the cDNAs for IgG anti-oxazolone (anti-Ox) kappa light chain IgG3 and IgG1 anti-Ox heavy chain genes were obtained from mice, which were immunized against 2-phenyloxazolone (Kaartinen, M., Griffiths, G. M., Markham, A. F. & Milstein, C, mRNA sequences define an unusually restricted IgG response to 2-phenyloxazolone and its early diversification. *Nature* 304 (1983), 320–324.

EXAMPLE 1

Induction, enrichment and isolation of auxotrophic *T. reesei* mutant strains

Auxotrophic mutants requiring tryptophan or arginine for growth were isolated using filtration enrichment as described by Nevalainen (Nevalainen, H., Technical Research Center of Finland, Publication 26 (1985)). The mutagenic agent used was UV-light. From arginine requiring auxotrophs, mutants deficient in the argB gene were identified by using a series of minimal plates supplied by different intermediates in the arginine biosynthesis (Nevalainen, H., Technical Research Center of Finland, Publication 26 (1985). Mutants requiring citrulline for growth were considered as possible argB⁻ mutants. The argB⁺ character of isolated mutants was confirmed by transforming them into prototrophy using the plasmid pSal43 containing the *A. nidulans* argB gene (example 4).

Tryptophan requiring mutants were characterized on a series of minimal medium plates supplied by anthranilic acid, indole, or tryptophan (Sanchez, F. et al., *Gene* 51:97–102 (1987)). Colonies requiring indole for growth were taken as putative trpC routants and their trpC⁺ character was confirmed by, for example, transformation with the pHY101 plasmid of *A. nidulans* (Van Gorcom, R. F. M. et al., *Gene* 40:99–106 (1985)).

EXAMPLE 2

Preparation of protoplasts

Mycelium was grown on cellophane disks on Potato Dextrose Agar plates (Difco). Mycelium from 5 cellophane cultures was suspended in 15 ml of a 5 mg/ml solution of Novozym$^R$ 234 in 1.2M sorbitol buffered at pH 5.6 with 0.1M potassium-phosphate. The mixture was incubated 1.5–2 h at 30° C. Protoplasts were separated from mycelial debris by filtration through sintered glass (porosity 1) pelleted for 5 min at 4000 g and washed twice with 1.2M sorbitol-10 mM Tris, HCl pH 7.5.

Better purification of protoplasts can be achieved by using a method described by Tilburn et al. (Tilburn, J., et al., *Gene* 26:205–221 (1983)). 5 mg/ml solution of Novozym$^R$ 234 in 1.2M MgSO$_4$ buffered at pH 5.8 was used for protoplasting. After incubation and filtration the protoplast suspension was centrifuged at 4000 g for 15 min with an overlay of an equal volume of 0.6M sorbitol-100 mM Tris, HCl, pH 7.0. Protoplasts formed a sharp band halfway the tube. The protoplasts were suspended in 1 vol of 1.2M sorbitol-10 mM Tris, HCl, pH 7.5, spun down and washed twice in 1.2M sorbitol-10 mM Tris, HCl, pH 7.5. The protoplasts were suspended in 1.2M sorbitol-10 mM CaCl$_2$, 10 mM Tris, HCl, pH 7.5 at a concentration of 5×10$^6$–5×10$^7$ protoplasts/ml.

The viability of the protoplasts was estimated on Trichoderma minimal medium with 1M sorbitol as osmotic stabilizer. The protoplasts were plated in 3% agar overlay. The regeneration frequency was 40–80% for the strain QM 9414 (ATCC 26921).

EXAMPLE 3

Transformation of *T. reesei* using *A. nidulans* acetamidase (amdS) gene

Plasmid p3SR2 was used in transformation. It contained *A. nidulans* DNA carrying the whole acetamidase structural gene amdS and its regulatory region amdI (Hynes, M. J., et al., *Mol. Cell. Biol.* 3:1430–1439 (1983); Tilburn, J., et al., *Gene* 26:205–221 (1983)).

20μl (4–10 μg) of transforming DNA was added to 200 μl of protoplast solution. 50 μl of 25% PEG 6000–50 mM CaCl$_2$-10 mM Tris, HCl, pH 7.5 was added and the mixture was incubated for 20 Min on ice. 2 ml of the PEG-solution was added and the mixture was further incubated 5 min at room temperature. 4 ml of 1.2M sorbitol-10 mM CaCl$_2$-10 mM Tris, HCl, pH 7.5 was added and the protoplasts were plated in 3% agar overlay. The selective medium was Trichoderma minimal medium with 10 mM acetamide as the sole nitrogen source instead of (NH$_4$)$_2$SO$_4$, and supplemented with 1M sorbitol as osmotic stabilizer and 12.5 mM CsCl to repress the background growth.

Transformation frequencies from 40 to 600 transformants per μg DNA were obtained for the strain QM 9414 (ATCC 26921). The highest frequencies were obtained when the DNA was purified with two cycles of CsCl/ethidium-bromide centrifugation.

Sporulation was rarely observed on the selective medium but the transformants sporulate normally when transferred to Potato Dextrose Agar. Their ability to grow on acetamide varied. The diameter of the colonies on the selective medium ranged 1 mm to 10–20 mm.

The mitotic stability of the transformants was investigated. Ten large transformants of varying size were subcultured on acetamide-CsCl plates, sporulated on potato dextrose (PD) and replated on PD. To exclude heterogeneity caused by heterokaryosis, individual colonies arising from one spore were tested for AmdS⁺ phenotype. One positive clone from each original transformant was subjected to successive platings (5 growth cycles) on non-selective medium and phenotype was tested after each generation on the selective medium. Of 10 large transformants tested, after one cycle on non-selective medium six of the ten transformants gave 100% AmdS⁺ conidia, three 47–87% and one transformant gave no AmdS⁺ conidia. This result remained the same through five non-selective growth cycles, suggesting that the initially unstable AmdS⁺ phenotype can be stabilized later on.

From ten original small colonies, three gave spores with variable frequencies of AmdS⁺ phenotype (94%, 44%, and 5% of the spores). The other seven clones gave only spores unable to grow on acetamide. Interestingly, all AmdS⁺ spores obtained showed vigorous growth on acetamide plates, characteristic of large colony transformants.

The presence of the plasmid DNA in the transformants was analyzed by Southern blots of total DNA, isolated from transformants (Raeder, U. et al., *Lett. Appl. Microbiol.* 1:17–20 (1985)), cut with XhoI or SalI and EcoRI. The vector pUC18 and the SalI-EcoRI fragment containing the amdS gene of plasmid p3SR2 were used as probes. The transformation was shown to have occurred by recombination at a number of different sites in the Trichoderma genome DNA, one to several copies per genome.

EXAMPLE 4

Transformation of argB⁻ and trpC$^{31}$ *T. reesei* with the *A. nidulans* argB and trpC genes Complementation of auxotrophic mutations in *T. reesei* by heterologous DNA was demonstrated. The plasmid pSal43 containing the argB gene from *A. nidulans* was used to transform *T. reesei* argB⁻ mutant strains. The plasmid pHY101 (Van Gorcom, R. F. M. et al., *Gene* 40:99–106 (1985) containing the trpC gene from *A. nidulans* was used to transform *T. reesei* trpC⁻ mutant strains. The transformants were selected on minimal medium without arginine or tryptophan. The frequency of transformation varied, depending on the plasmid, from 10 to 300 transformants per microgram DNA.

Chromosomal DNA was isolated from the transformants and used for Southern hybridization experiments to verify the proper integration of plasmid DNA into the chromosomal DNA of *T. reesei*. Multiple tandem copies of pSal143 were integrated in the genome. Southern and dot blot hybridizations showed that in transformants analyzed the copy number of argB varies from appr. 2 to over 100. The ArgB⁺ transformants were shown to be phenotypically 100% stable through at least 3 generations. This was tested by successive platings of conidia from five transformants onto complete medium and thereafter testing the Arg⁺ phenotype on minimal medium (50–80 colonies/transformant).

EXAMPLE 5

Cotransformation of *T. reesei* with amdS and argB plasmids

The possibility of cotransforming Trichoderma with a nonselectable plasmid was first shown with the arginine auxotrophic mutant.

The argB⁻ *T. reesei* strain was transformed with equal molar amounts of *A. nidulans* plasmids pSal43 (argB) and p3SR2 (amdS), transformants were selected for Arg⁺ phenotype and tested for acquisition of amdS by streaking on acetamide-CsCl-plates. Of the ArgB transformants, 86% were also AmdS⁺. Southern analysis of cotransformants indicated that both plasmids were integrated as variable amounts of copies in several different locations in the genome.

Double selection on minimal acetamide-CsCl-medium resulted in ~100 big Amd+Arg⁺ transformants per µg of DNA and a number of small colonies, characteristic of amdS transformation.

When the stability of the ArgB⁺ phenotype of the argB amdS cotransformants was tested, three out of five proved 100% stable, whereas the other had lost the ArgB⁺ character in 7% or 80% of the progeny analyzed. The same individual colonies had also lost the AmdS⁺ phenotype. Whether this instability was caused by e.g. the cointegration of argB with the amdS to the same chromosomal location is not known.

The plasmid pAN5-4IB which contains the *E. coli* lacZ gene coupled in phase to the promoter and N-terminal protein coding region of the *A. nidulans* glycerol phosphate dehydrogenase gene (gpd) (Van Gorcom, R. F. M., et al., *Gene* 48:211–217 (1988)) was also used for cotransformation. In addition, this plasmid contains the A. nidulans argB gene and pBR322 sequences. Prototrophic *T. reesei* (QM 9414) was cotransformed with the plasmid p3SR2 (amdS) and pAN5-4IB, transformants were selected for Amd⁺ phenotype and screened for β-gal expression on acetamide-CsCl-plates containing Xgal. No endogenous *T. reesei* β-galactosidase activity could be detected when glucose was present in the medium and pH of the Xgal plates was neutral.

After 1–4 days of growth blue color was visible. When 1.0/0.7 molar ratio of the plasmids (p3SR2/pAN5-4IB) was used in transformation 13% of the big and 6% of the small Amd⁺ clones showed β-galactosidase activity, with molar ratio of 1.0/2.6, 39% and 7% of Xgal⁺ clones, respectively, were obtained. The presence of both plasmids in Amd⁺ transformants showing blue color was verified by Southern hybridization.

EXAMPLE 6

Construction of a cbh1⁻ *Trichoderma reesei* strain

Figure 2:
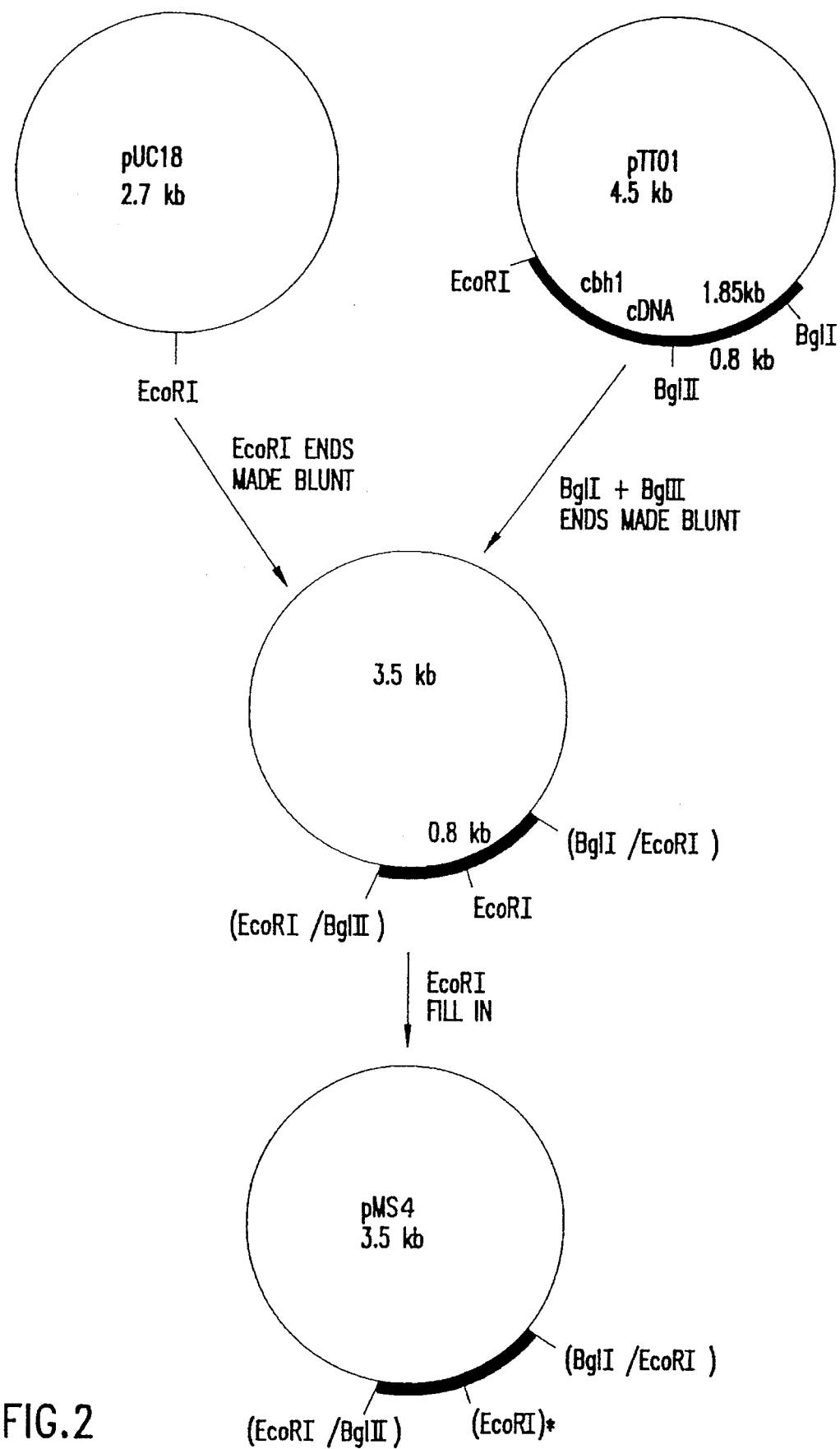
FIG. 2 shows the construction of plasmids pMS4 used for insertion mutagenesis of the *T. reesei* chromosomal CBHI locus. Position of a frameshift mutation generated by inactivation of EcoRI site is marked with *.

The activation of different cellulase genes in the manner described allows the construction of a series of *T. reesei* strains producing a particular combination of cellulase. cbh1⁻ strains are also important for the efficient production of heterologous proteins when using the cbh1 promoter. *Trichoderma reesei* strain QM 9414 (ATCC 26921) was shown to contain only one chromosomal copy of cbh1 gene by Southern hybridization using cbh1 specific probes and so one recombination event should inactivate the gene. An inactive gene was constructed as follows. The plasmid pTT01 (WO 85/04672) containing the full length cDNA clone of the cbh1 gene in the vector pUC8 was cut with restriction enzymes BglI and BglII. The 0.8 kb fragment from the 5' terminal region of the cbh1 gene was isolated from agarose gel by conventional techniques. The fragment was made blunt-ended using S1 nuclease and it was ligated to an EcoRI cut, blunt-ended pUC18 vector and transformed to *E. coli* JM109. DNA from the clone containing the cbh1 gene fragment was isolated and digested with restriction enzyme EcoRI which cuts in the middle of the BglI-BglII fragment of cbh1. The EcoRI-generated termini were filled in and back-ligated. A plasmid pMS4 containing a frameshift mutation in the middle of the truncated chb1 gene fragment was generated (FIG. 2).

Trichoderma was cotransformed with the plasmid pMS4 and the *A. nidulans* amdS containing plasmid p3SR2 with 3–4 times molar excess of plasmid pMS4.

Transformants were selected on the basis of the amdS⁺ phenotype as described (example 3) and purified on selective medium containing acetamide as a sole carbon source. Purified transformants were grown on microtiter plates in 200 µl of Trichoderma minimal medium with 1% Solka floc cellulose as carbon source and 0.2% proteose peptone as nitrogen source. The cellulase phenotype was tested by the Ouchterlony immunodiffusion by using undiluted growth media against the CBH I specific antiserum (sheep) as described (Nummi, M. et al., *Biochem. J.* 215:677–683 (1983)). A number of transformants were identified which produced normal amount of CBH II but no detectable CBH I.

EXAMPLE 7

I. Preparation of Plasmid 285' proC Containing the Prochymosin Gene (FIG. 3)

Figure 3:
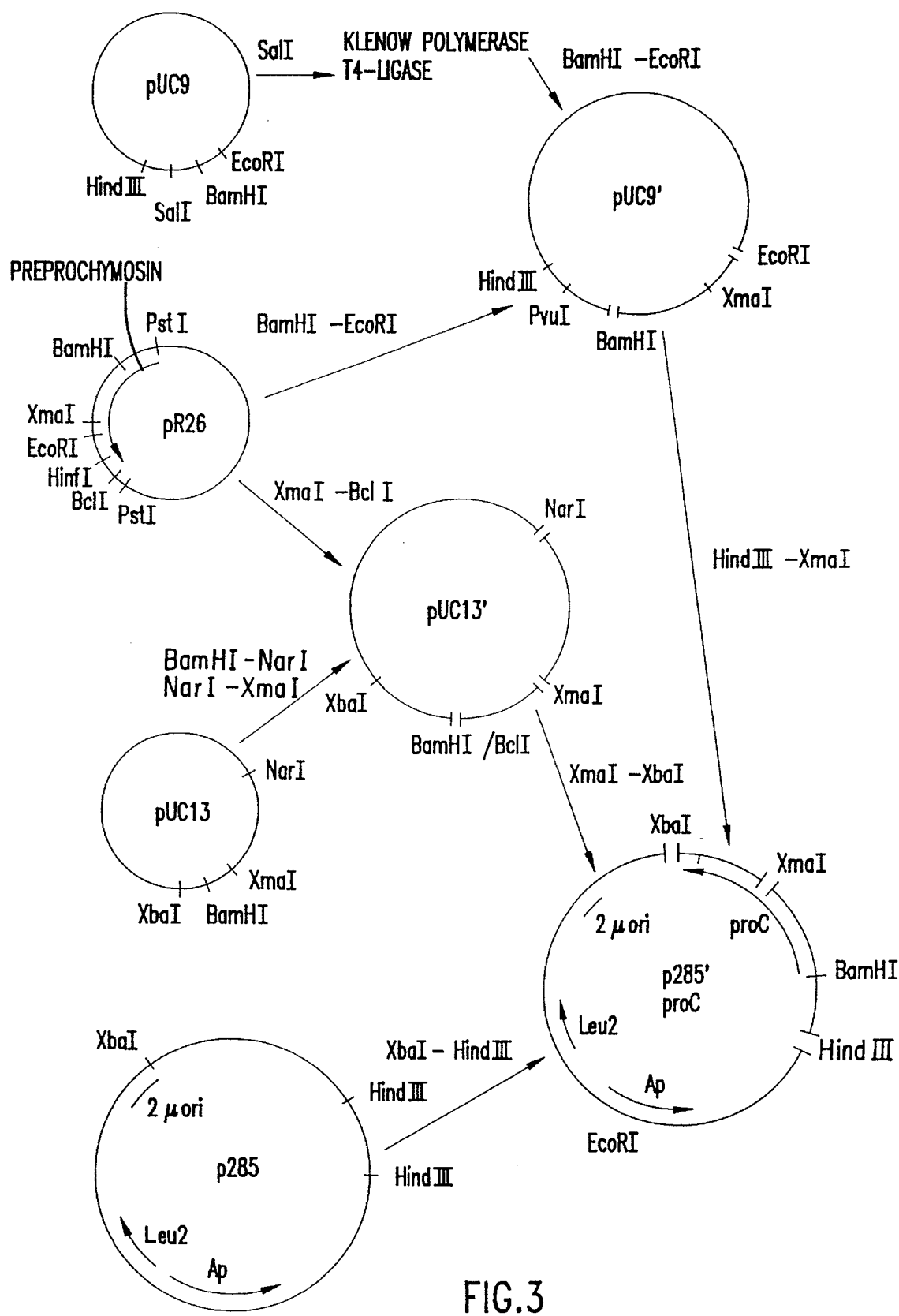
FIG. 3 shows the construction of plasmid p285' proC.

As an example of a heterologous protein in *T. reesei* we chose to express the prochymosin cDNA (FIG. 3). The preprochymosine gene was isolated from a calf stomach cDNA library and inserted into the PstI site of pBR322 by G-C tailing (Sollazzo, M., et al., *Gene* 37:199–206 (1985); Kunkel, T. A., *Proc. Natl. Acad. Sci. USA* 82:488–492 (1985)) to obtain pR26. pUC9 was cut with SalI and filled out with Klenow polymerase and ligated with T4 ligase. The obtained plasmid was cut with BamHI-EcoRI and the 2.7 kb large fragment was ligated with a 0.47 kb BamHI-EcoRI fragment from pR26 to create pUC9' containing a HindIII site N-terminally of the prochymosin gene. pUC13 was cut with BamHI-NarI and NarI-XmaI and the large respective small fragment was ligated with a 0.64 kb XmaI-BclI fragment of pR26 to obtain plasmid pUC13' containing a XbaI-site C-terminally of the prochymosin gene. A 0.65 kb XmaI-XbaI fragment of pUC13' was ligated with 0.46 kb HindIII-XmaI fragment of pUC9' and a 11 kb XbaI-HindIII fragment of p285 to create plasmid p285' proC containing the prochymosin gene as illustrated in FIG. 3.

II. Construction of Plasmid pAMG/Term pCAMG91 was digested with SalI and PstI restriction endonucleases. From such a digests a 698 bp fragment was isolated on an agarose gel. This SalI-PstI fragment contains the region encoding the 140 bp 3' untranslated part of the glucoamylase mRNA plus 540 bp 3' to the poly(A)-addition site. This 3' fragment was treated with T4-DNA polymerase to "blunt end" the restriction sites before the addition of XbaI linkers and digestion with XbaI restriction enzyme. This 3' end of the glucoamylase gene was ligated to pUC13 linearized with XbaI to create plasmid pAMG/Term containing the glucoamylase gene poly(A) addition region.

III. Construction of plasmid pMT837

Figure 4:
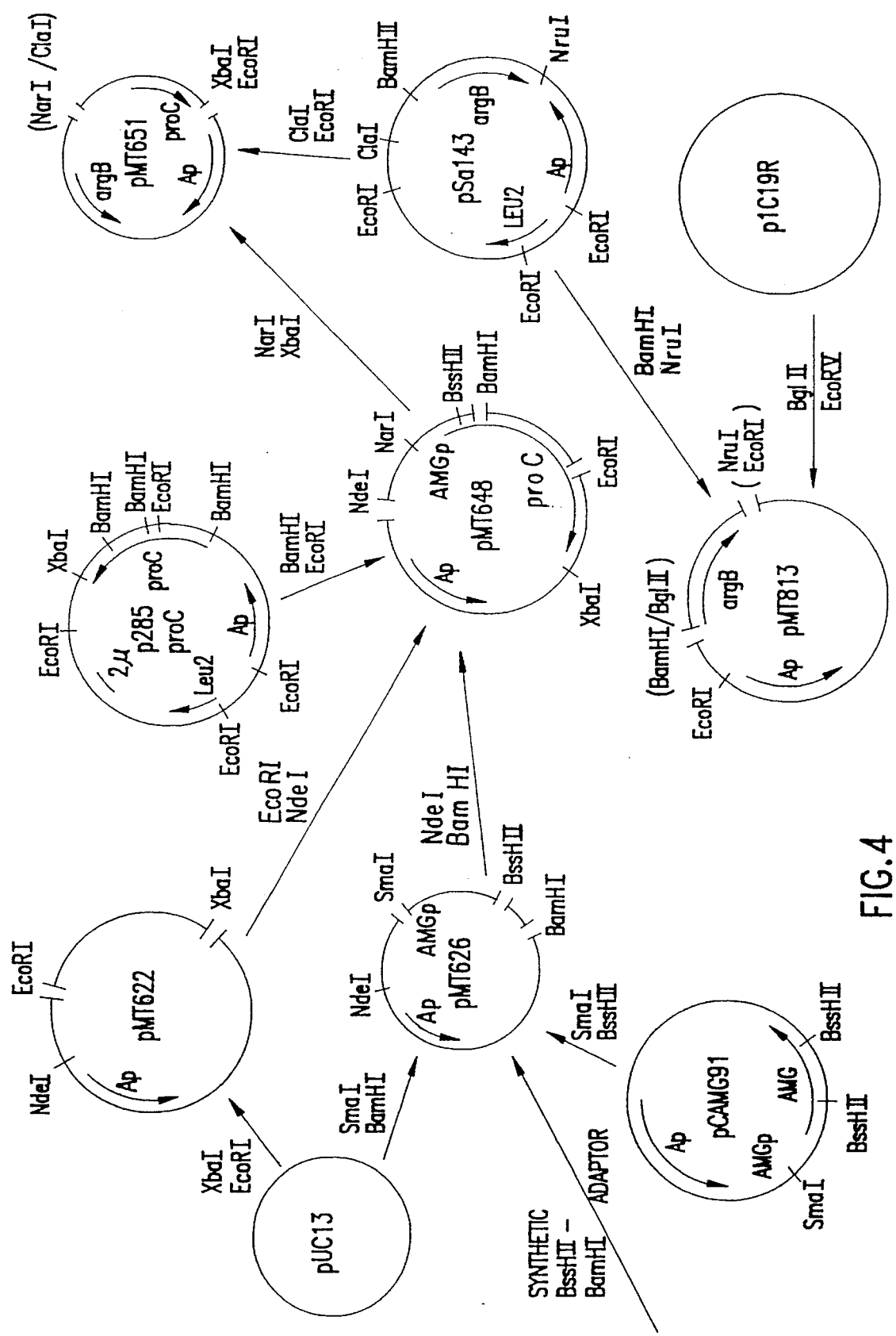
FIG. 4 shows the construction of plasmids pMT648 and pMT813.
Figure 5:
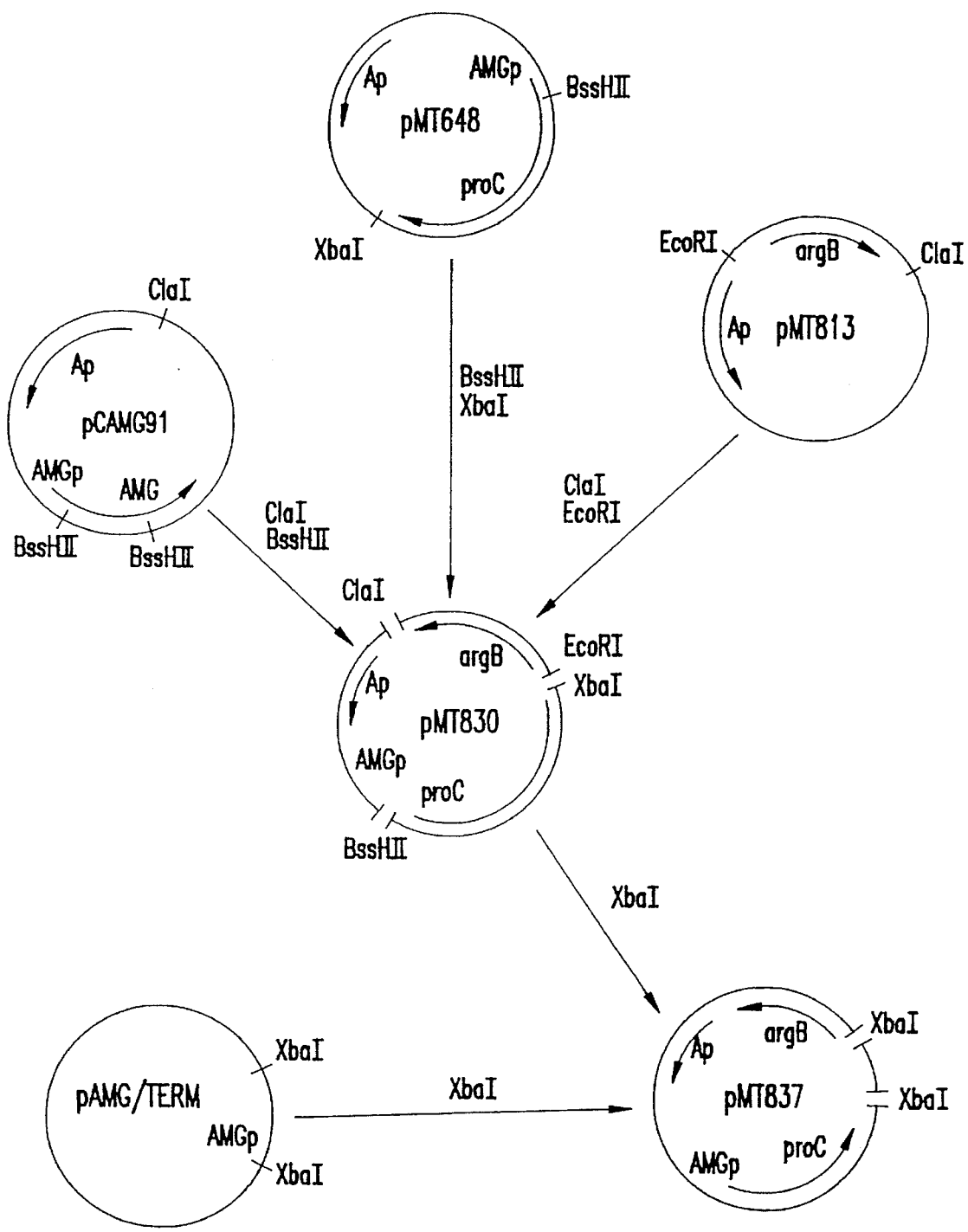
FIG. 5 shows the construction of plasmid pMT837.

A 0.5 kb SmaII-BssHII fragment of pCAMG91 containing the promoter and the sequences coding for the glucoamylase (AMG) signal and leader peptide was ligated to SmaI-BamHI digested pUC13 and a synthetic BssHII-BamHI adaptor encoding the first 6 amino acids of prochymosin. From the resulting plasmid, pMT626, a 0.8 kb NdeI-BamHI fragment was isolated and ligated to a 0.5 kb BamHI-EcoRI fragment from p285' proC containing the sequence for the N-terminal half of proC and to a 3.0 kb EcoRI-NdeI fragment of pMT622 containing the C-terminal part of the sequence for proC. (pMT622 is simply an EcoRI-XbaI subclone of p285' proC in pUC13). The resulting plasmid pMT648 (see FIG. 4) contains the entire prochymosin gene preceded by AMG promoter and signal/leader encoding sequences. pMT648 was further modified to contain the argB gene of A. nidulans (John, M. A., et al., *Enzyme Microb. Technol.* 6:386–389 (1984)). A 1.8 kb NarI-filled in XbaI fragment of pMT648 was ligated to a 6.8 kb ClaI filled-in EcoRI fragment of pSal43, to give pMT651. Sequences further upstream of the AMG promoter (upstream activating sequences; UAS's) were furthermore inserted. This was achieved by ligating a 3.7 kb ClaI-BssHII fragment from the original clone pCAMG91 to the 1.1 kb BssHII filled in XbaI fragment of pMT648 containing the proC sequences, and the argB gene as a 3.1 kb ClaI-filled in EcoRI fragment from pMT813 (pMT813 is the argB gene cloned as a 3.1 kb BamHI-NruI fragment cloned into EcoRV-BglII cut piCl9R). The resulting plasmid, pMT830, has got an expression unit containing the UAS's, promoter, signal and leader sequences from AMG and the entire gene for proC. Finally, the terminator sequence of AAIG is taken as a 0.6 kb XbaI-XbaI fragment from plasmid pAMG/Term and inserted into the XbaI cut and dephosphorylated pMT830 to give pMT837. The construction of pMT837 is illustrated in FIG. 5.

Example 8

Production of chymosin using pMT837

*T. reesei* strains QM 9414 and RUT-C-30 were cotransformed with plasmids pMT837 and p3SR2. Plasmid pMT837 contains the prochymosin gene preceded by the AMG promoter and signal/leader sequence. The construction of plasmid pMT837 was described in Example 7 (see also FIGS. 3–5). Cotransformation and selection was carried out as in Example 5.

For chymosin production, transformants were cultured on minimal medium containing 1% Solka floc cellulose and 0.2% proteose peptone.

The mycelia were collected and the supernatant was concentrated, when necessary, by TCA precipitation and diluted with 2M NaOH 10 mM Tris (pH 8.5). The samples were fractioned on SDS-page (7.5%–15% polyacrylamide gradient) and electroblotted to a nitrocellulose filter. The filters were incubated with rabbit prochymosin antiserum and stained with 4-chloro-1-naftol using α-rabbit-IgG-peroxidase conjugate purchased from Sigma.

Chymosin was shown to be secreted into the medium approximately at the level of 1 μg/l. Since the AMG promoter clearly functions inefficiently in *T. reesei* homologous *T. reesei* promoter-terminator vectors were constructed to improve the production level of chymosin.

Example 9

Figure 6:
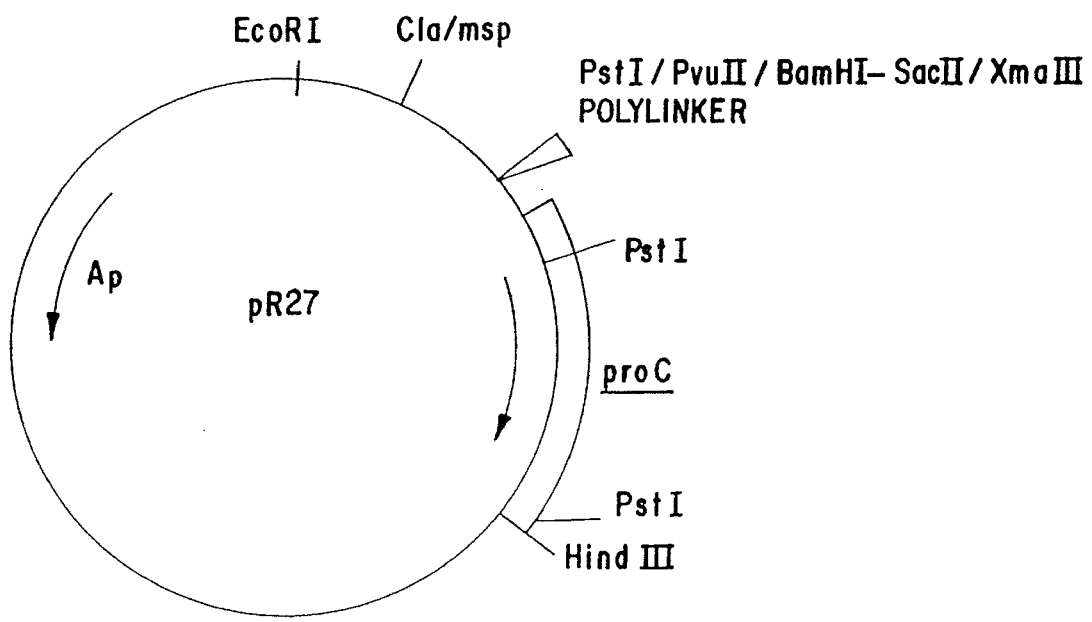
FIG. 6 shows the restriction map of plasmid pR27.

The construction of heterologous expression vectors for production of calf prochymosin in *T. reesei* using the cbh1 promoter I. The joining of prochymosin gene to cbh1 terminator region The calf prochymosin gene was obtained from plasmid pR27 (FIG. 6). The PstI-PstI fragment (~1110 bp) containing almost the whole gene was isolated from agarose gel by conventional techniques and ligated to the PstI site of pUC19.

This plasmid was partially digested with PstI, ends made blunt with S1 nuclease and an AvaII terminator fragment (~750 bp) of cbh1 gene (blunt ends with Klenow fragment) was ligated into this plasmid. The terminator region of cbh1 gene was obtained from the terminal 1.8 kb BamHI fragment of cbh1 cDNA subcloned in pBR322 (Teeri, T., et al., *Bio/Technology* 1:696–699 (1983)).

Figure 7:
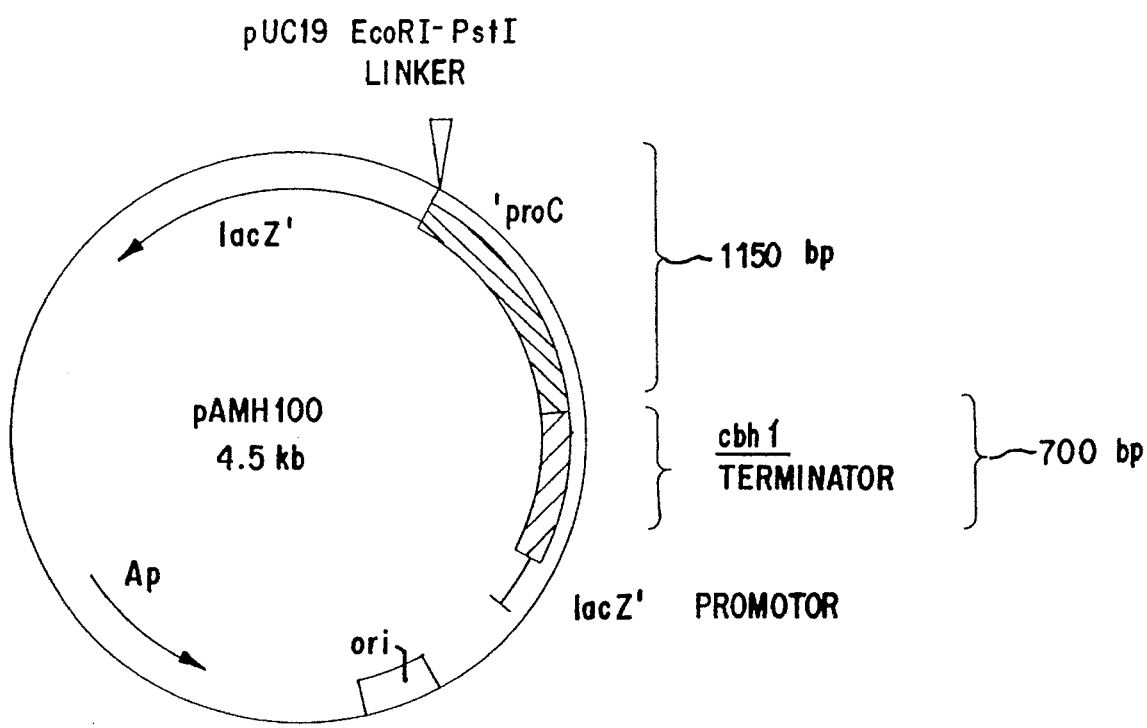
FIG. 7 shows the restriction map of plasmid pAMH100.

This plasmid containing the proC' fragment coupled with the terminator region of cbh1 gene in pUC19 was called pAMH100 (FIG. 7).

II. Fusion of the cbh1 promoter region and prochymosin coding region using BglI-SacII adaptor The SacII-PstI fragment (80 bp) coding for the N-terminal region of prochymosin was isolated from plasmid pR27 (see FIG. 6). The cbh1 promoter region was first subcloned from the genomic clone λ44A as a 2.8 kb long EcoRI-EcoRI fragment into pUC18 (plasmid pUA01, FIG. 8), and then a ~2.2 kb long EcoRI-BglI fragment was isolated from this subclone. The BglI site is located in the middle of the signal sequence of cbh1 gene. The precise joining of the ~2.2 kb long EcoRI-BglI fragment, containing the promoter and about half of the signal peptide coding region of cbh1 gene, to the ~80 bp SacII-PstI prochymosin fragment is mediated by the BglI-SacII adaptor (NOR 202+NOR 203, FIG. 10). These fragments together with the adaptor were ligated into pUC19 digested with EcoRI-PstI. This plasmid codes for a complete signal sequence of CBH I fused to the first amino acid of prochymosin followed by some of its N-terminal sequences. Finally, from this construction the EcoRI- pcbh1 ss-proC-PstI fragment was isolated, ligated from its 3' end into pAMH100 digested with PstI. A fragment of about 6.7 kb was isolated from the ligation mixture by gel electrophoresis and the 5' end of the fragment (the EcoRI end) and the 3'-end of plasmid pAMH100 was S1 treated and ligated. Thus, the promoter of the cbh1 gene and proC' fragment was transferred in front of proC followed by the cbh1 terminator area. The construction was named pAMH102 (FIG. 11).

III. The addition of a selectable marker to chymosin expression plasmid

As a selectable marker in the expression plasmids either the amdS gene of *A. nidulans* (Hynes, M. J. et al., *Mol. Cell. Biol.* 3:1430–1439 (1983)) or the argB gene of *A. nidulans* can be used (John, M. A. et al., *Enz. Microbiol. Technol.* 6:386–389 (1984)).

The amdS gene was isolated as a PvuI-SalI fragment from p3SR2 and ligated to the 6 kb long PvuI-SalI fragment of pAMH102. This selectable vector was named pAMH104 (FIG. 11).

Figure 8:
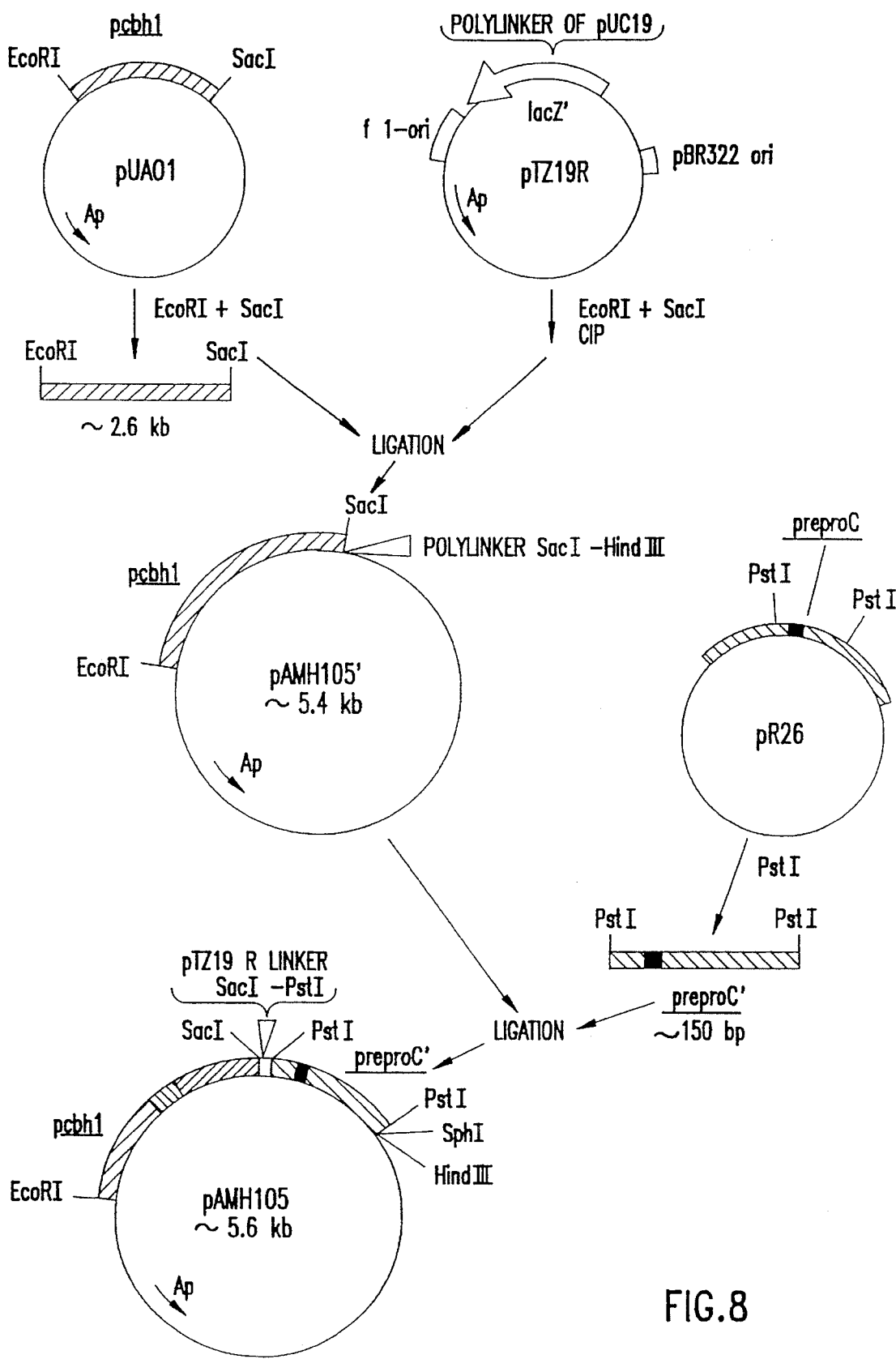
FIG. 8 shows the construction of plasmid pAMH105.
Figure 12:
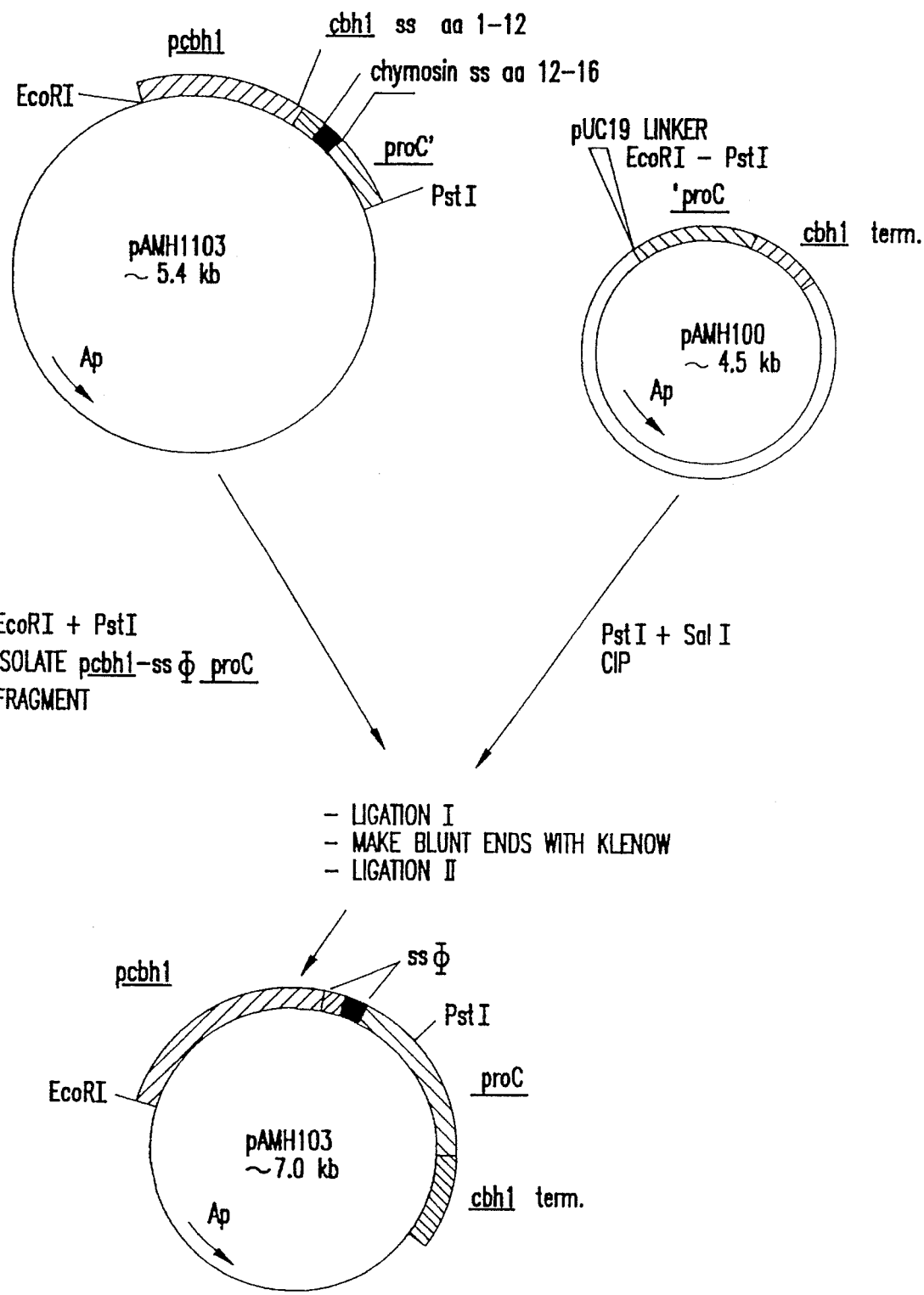
FIG. 12 shows the restriction map of plasmid pAMH1103 and the construction of pAMH103.
Figure 14:
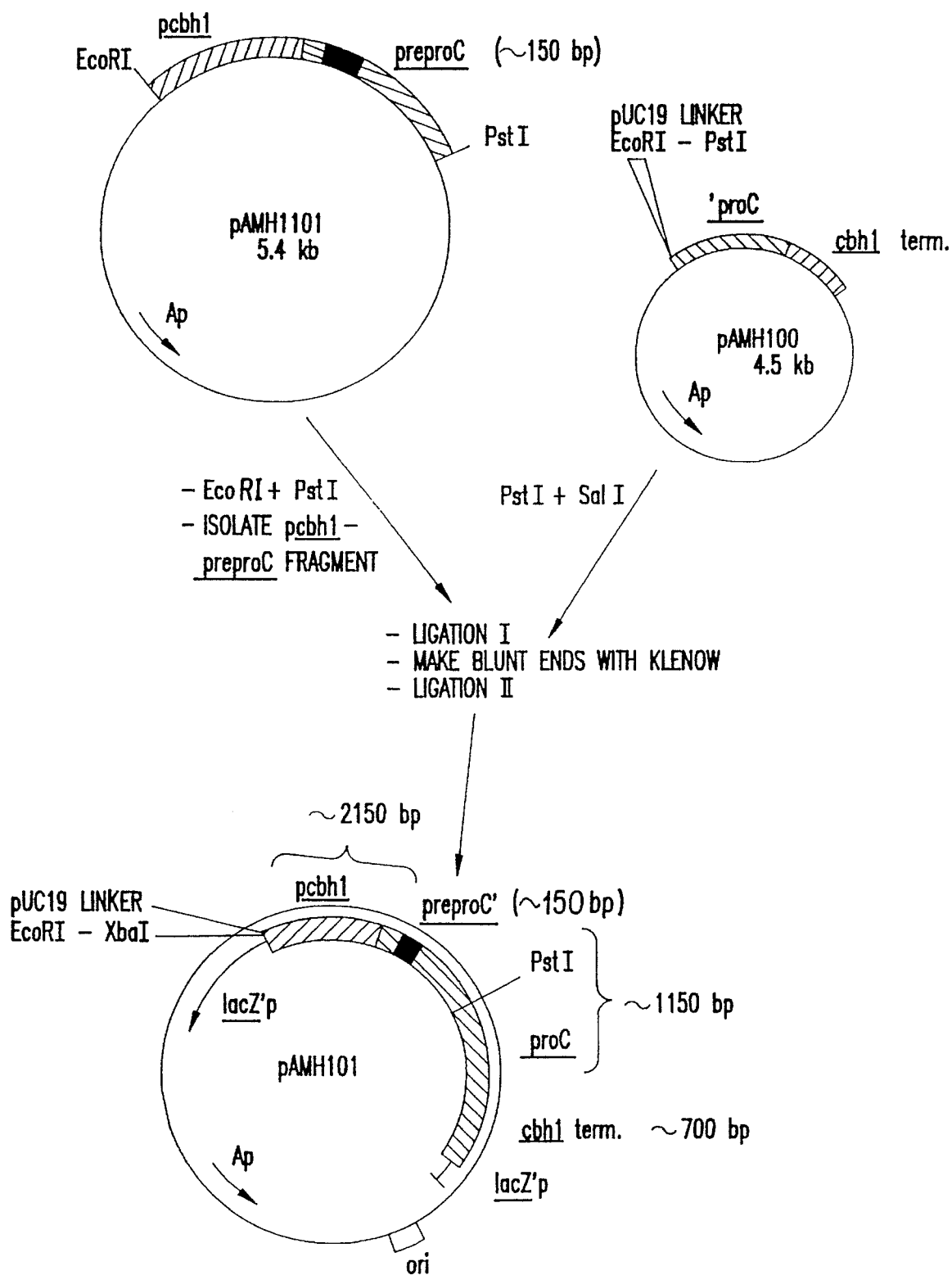
FIG. 14 shows the restriction map of plasmid pAMH1101 and the construction of pAMH101.

IV. The precise fusion of the cbh1 promoter and preprochymosin coding sequences using oligonucleotides The aminoterminal PstI fragment (~150 bp) of prepro-chymosin was isolated from pR26 (FIG. 3) which includes a complete preprochymosin cDNA clone, starting 12 bp upstream from ATG, inserted into PstI site in pBR322. This fragment was subcloned into the polylinker of pTZ19R together with the cbh1 EcoRI-SacI (~2.6 kb) promoter fragment which also includes the signal sequence coding region of cbh1 (FIG. 8). The cbh1 EcoRI-SacI fragment is obtained from a 2.8 kb EcoRI-EcoRI subclone in pUC18 (pUA01, FIG. 8) of the original λ44A clone (Teeri, T., et al., *Bio/Technology* 1:696–699 (1983)). pTZ19R (Pharmacia) is a pUC19 based plasmid including the F1 origin of replication and the T7 promoter enabling the use of ss-templ ate (single-stranded) for oligonucleotide mutagenesis. The construction of the resulting plasmid (pAMH 105) is illustrated in FIG. 8. From this plasmid the sequences between cbh1 promoter area and proC ATG were deleted by loop-mutagenesis using a specific oligonucleotide, OAMH 3 (FIG. 10). The performance of oligonucleotide directed mutagenesis is illustrated in FIG. 9. The oligonucleotide in question was phosphorylated, annealed to ss pAMH 105 DNA (Marsh, J. L., et al., *Gene* 32:481–485 (1984), ss-DNA was isolated from JM103/pAMH105 (as described by Pharmacia) in a 20:1 molar ratio, respectively. The oligonucleotide primer was elongated using Klenow polymerase and T4 ligase as described in Eghtedarzadeh, M. K. et al., *Nucl. Acids Res.* 14:5115 (1986). The elongated mixture was digested with SmaI (resides in the polhylinker of pTZ19R, see FIG. 9) prior to transformation into the mutl mismatch repair deficient strain of *E. coli*, BMH71.18 (Vieira, J., et al., *Gene* 19:259–268 (1982)). The pool of transformants was grown overnight in 5 ml liquid culture (Luria broth as described in Miller, J. H., in *Experiments in Molecular Genetics*, Cold Spring Harbor Laboratory, New York, (1972), with 100 µg/ml ampicillin). Plasmid DNA was isolated from pool of transformants and it was redigested with SmaI and retransformed into *E. coil* JM109 strain. The screening of potential deletion clones was performed by digestion using different restriction enzymes and the specificity of deletion was further confirmed by sequencing. The resulting plasmid was called pAMH1101 (FIG. 12). This plasmid was further digested with EcoRI and PstI and the resulting pcbh1-preproC fragment was isolated (FIG. 14) and ligated at its PstI-end to pAMH100 plasmid digested with PstI and SalI. The ends of the resulting ligated fragment were made blunt by Klenow and ligated. The resulting plasmid was called pAMH101 and it contains the cbh1 promoter area fused to the signal sequence of prochymosin and the whole prochymosin coding region fused to the terminator area of cbh1 gene (FIG. 14).

V. The precise fusion of the cbh1 promoter and preproC gene by signal sequence fusion performed by using oligonucleotides The construction of plasmid pAMH1103 (FIG. 12) was performed essentially as pAMH1101 described in details in the preceding section IV with the exception that the specific oligonucleotide used for this construction was OAMH1 (FIG. 10 and 9). The resulting plasmid pAMH 1103 contains a signal sequence fusion including amino acids (aa) 1–12 from the cbh1 signal sequence fused to aa 12–16 from the preproC signal sequence preceding the aminoterminal part (~140 bp) of the coding region of proC gene (FIG. 12). From plasmid pAMH 1103 the pcbh1 -sso-proC' (o=fusion) fragment was subcloned into pAMH 100 essentially as described in the preceding section IV (see FIG. 12). The resulting plasmid pAMH 103 includes the promoter area of cbh1 and signal sequence fusion of cbh1 and prepraC preceding the proC coding region fused to the cbh1 terminator area.

Figure 13:
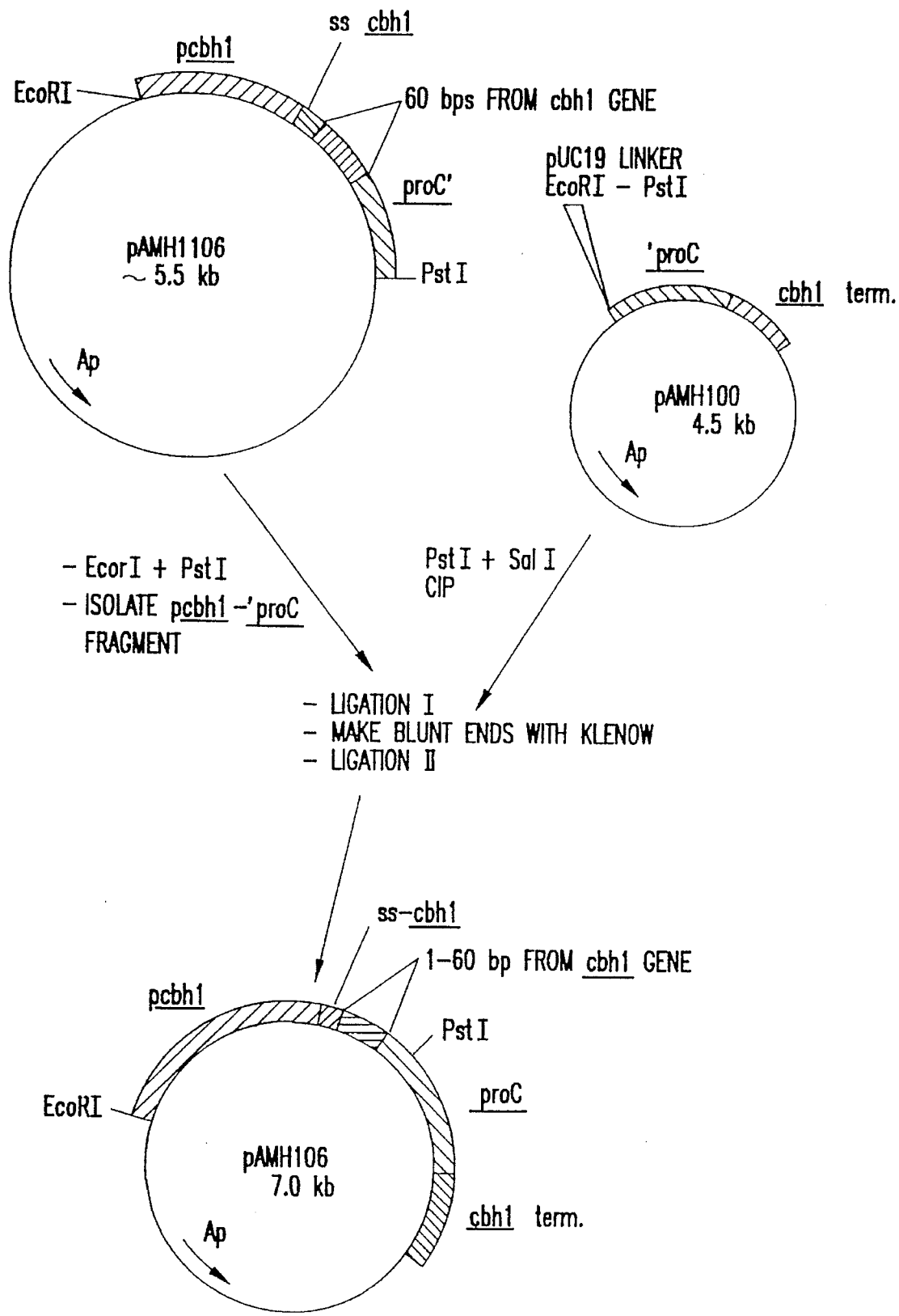
FIG. 13 shows the restriction map of plasmid pAMH1106 and the construction of pAMH106.

VI. The precise fusion of the cbh1 coding region to proC coding region by using oligonucleotides The construction of plasmid pAMH 1106 (FIG. 13) was performed essentially as pAMH 1101 described in details in the preceding section IV with the exception that the specific oligonucleotide used for this construction was OAMH2 (FIG. 10 and 9). From the resulting plasmid pAMH 1106 including the promoter area of cbh1, signal sequence of cbh1 and the coding region of 1–20 first aa of mature CBH I fused to the coding region of proC the fragment containing pcbh1-mature o-proC' was subcloned into pAMH100 essentially as described in the preceding section IV (FIG. 12). The resulting plasmid pAMH106 includes the promoter area of cbh1, signal sequence of cbh1, coding region of aa 1–20 of mature CBHI fused to the coding region of proC.

Example 10

Production of chymosin using pAMH102 and pAMH104

*T. reesei* strains QM 9414 and RUT-C-30 were cotransformed with plasmids pAMH102 and p3SR2 in molar ratio 5:1, respectively. The construction of plasmid pAMH102 was described in Example 9 section II. Cotransformation and selection was carried out as in Example 5. The transformants were purified on selective acetamide plates as described in Example 3.

Figure 17:
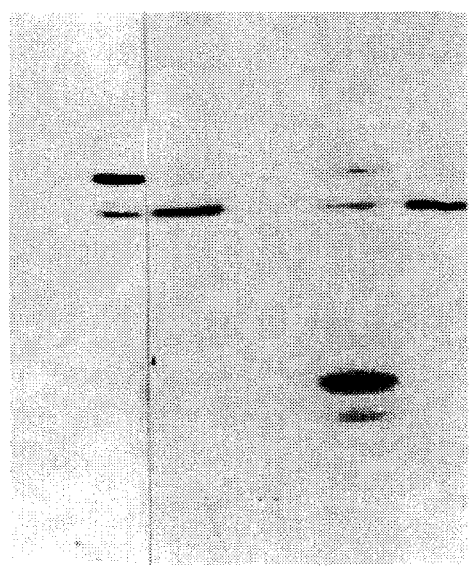
FIG. 17 shows the expression of chymosin in *T. reesei*, Western blot. Lane 1; purified prochymosin control, includes traces of pseudochymosin and chymosin. Lane 2; culture supernatant from growth of strain including pAMH102. Lane 3; control supernatant from strain without plasmids. Lane 4; mycelia from strain including pAMH102.

For chymosin production transformants were cultured on minimal medium (10 to 50 ml) containing 1% Solka floc cellulose and 0.2% proteose peptone. The mycelia were collected and the supernatant was concentrated by TCA precipitation and diluted into 2M NaOH 10 mM Tris (pH 8.5). The mycelia were broken in the presence of liquid nitrogen, broken cells were pelleted and the supernatant treated in the same way as the culture media. The samples were fractioned on SDS-page (7.5%–15% polyacrylamide gradient) and electroblotted to a nitrocellulose filter. The filters were incubated with rabbit prochymosin antiserum and α-rabbit-IgG-AP (alkaline phosphatase) conjugate and stained with nitro blue tetrazolium and 5-bromo-4-chloro-3-indolyl phosphate purchased from Promega Biotec. The amount of chymosin inside and outside the mycelium was compared (FIG. 17). It was shown by Southern hybridization that the clones containing higher number of copies of plasmid pAMH102 integrated into the fungal chromosomal DNA also produced more chymosin. When using a one-copy transformant the amount of secreted chymosin was 100 µg/l of culture medium when approximated from Western gels (FIG. 17). The secreted prochymosin was shown to be processed to an active chymosin by Western gels and by the milk clotting activity (chymosin clots milk by cleavage of β-casein determination) (Bailey, M. J., et al., *Biotechnol. Lett.* 10:161–166 (1988)). The amount of various forms of chymosin (preproC, proC, C and chymosin derived degradation products inside the cell) inside the mycelium was determined to be 0.04 % of mycelial total protein (FIG. 17) and the amount of secreted chymosin was 60% of the total chymosin produced. This shows the efficiency of *T. reesei* to secrete even heterologous gene products outside the mycelia.

Transformants with several copies of plasmid pAMH104 (FIG. 11), able to secrete larger amounts of prochymosin were screened for by determining the milk clotting activity of the growth media. The best transformant out of the 40 studied was found to secrete 500 µg/l of culture medium as determined on Western gels and by milk clotting activity.

Since the amount of secreted, active chymosin was increased 200-fold when cultures were grown in a 5 l laboratory fermenter compared to the small-scale cultures (10–50 ml), the amount of chymosin produced by this type of strain is around 100 mg/l.

Example 11

Construction of a general expression vector for production of homologous and heterologous proteins in *T. reesei*

Figure 15:
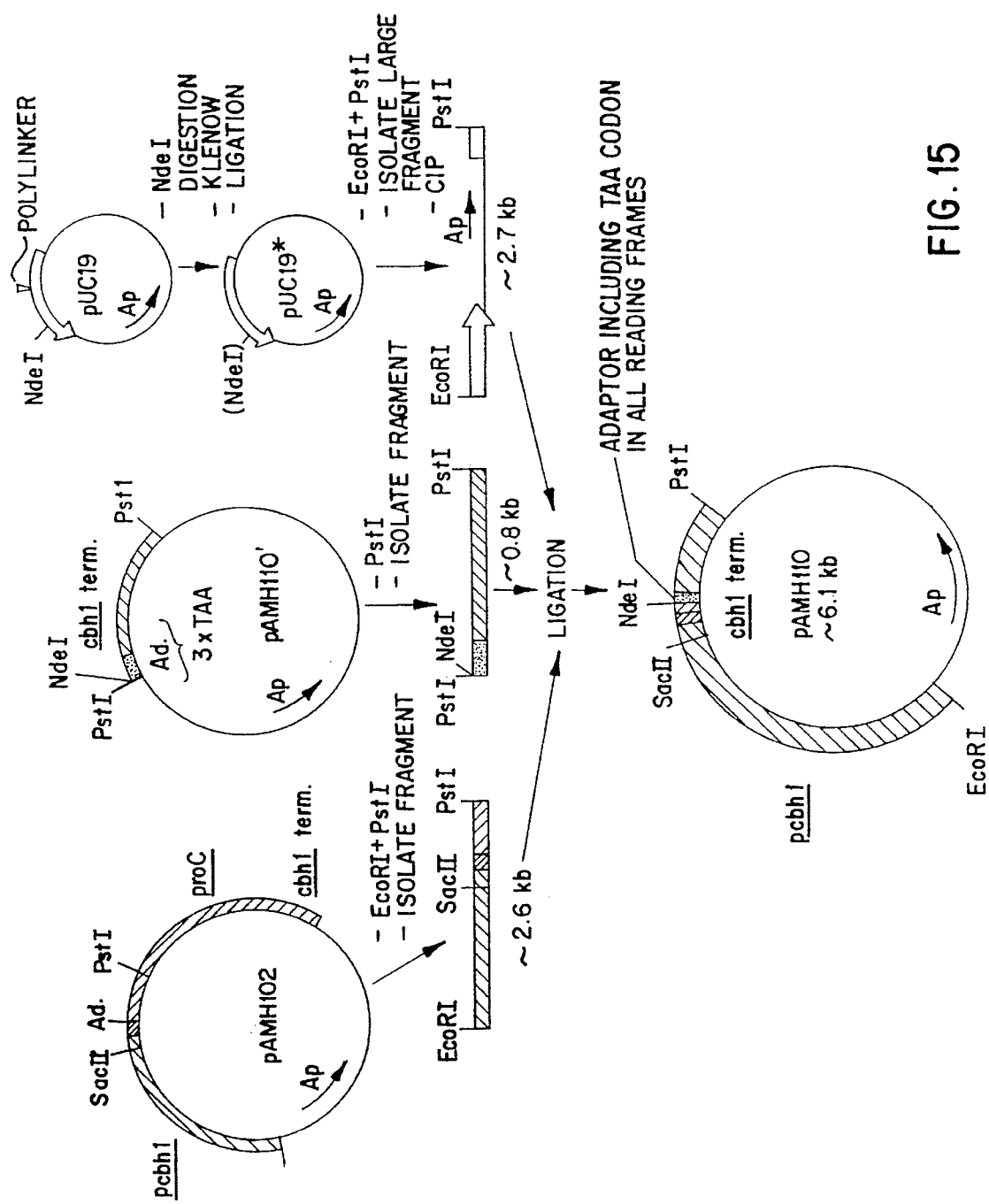
FIG. 15 shows the construction of plasmid pAHM110.

In order to be able to construct vectors for production of various proteins in *T. reesei* a general expression vector including the promoter and terminator areas of the cbh1 gene was constructed. The cab1 terminator was subcloned together with an adaptor including the stop codon TAA in three reading frames into the PstI site of pUC19 resulting in plasmid pAMH110' (FIG. 15). The PstI terminator fragment was isolated from pAMH110', the cbh1 promoter area was isolated from pAMH102 as an EcoRI-PstI fragment including the amino terminus of proC gene and these fragments were subcloned into an EcoRI-PstI digested pUC19* from which the single NdeI site had been made blunt with Klenow prior to this subcloning step. The resulting plasmid pAMH110 includes the promoter and terminator of cbh1 gene and between these sequences a stuffer fragment which can be removed by digestion with SacII and NdeI. After the ends are made blunt any cDNAs or chromosomal copies of genes can be inserted between the promoter and terminator (FIG. 15).

Example 12

The expression of *T. reesei* endoglucanase I under cbh1 promoter

Figure 16:
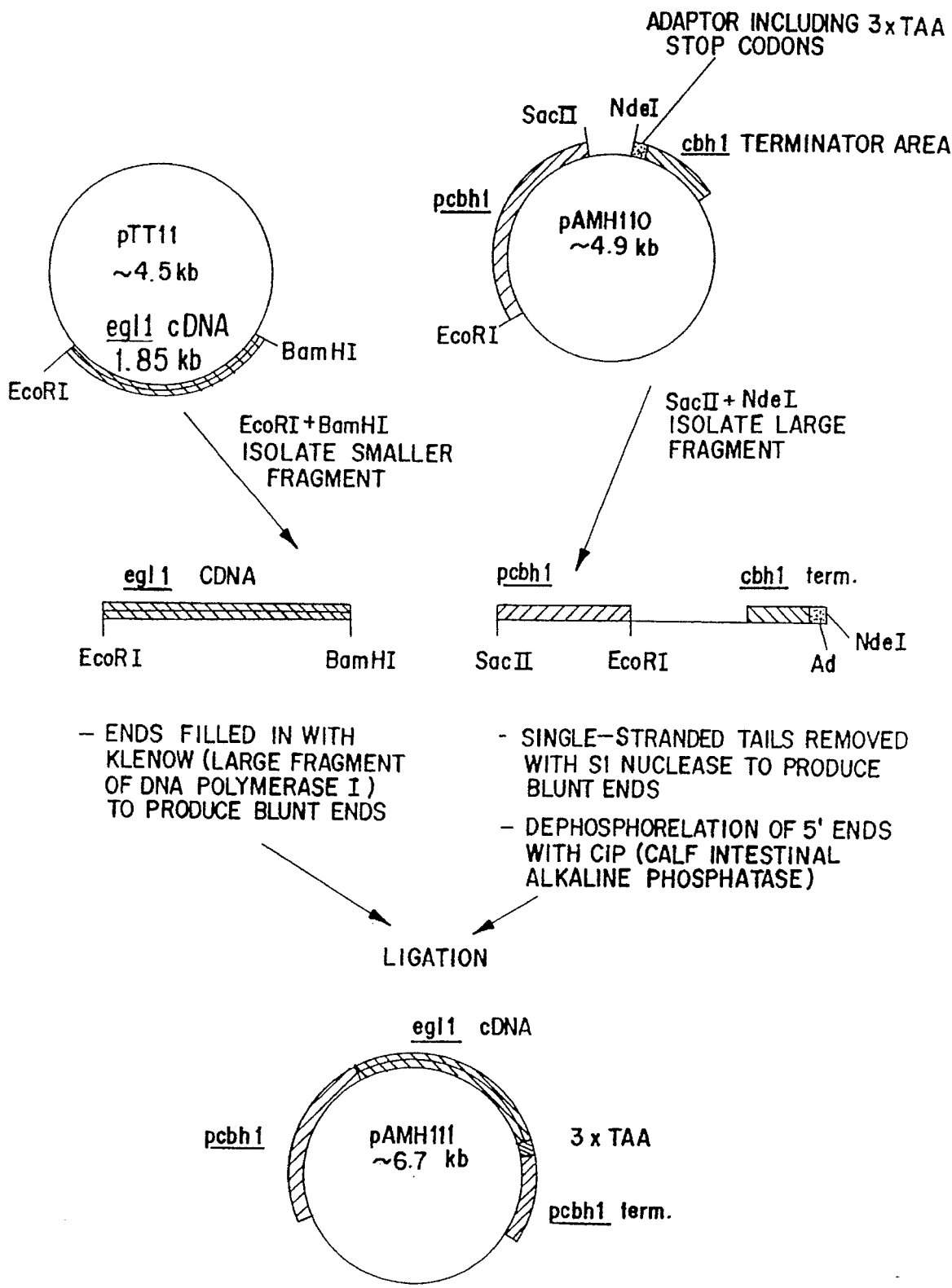
FIG. 16 shows the construction of plasmid pAMH111 used for expression of EGI under CBHI promoter function.

In order to increase the amount of endoglucanase produced, the egl1 gene was linked to the more powerful cbh1 promoter. The cDNA for *T. reesei* endoglucanase I was subcloned as an EcoRI-BamHI fragment into general expression vector pAMH110 (described in example 11) which was first digested with SacII-NdeI to delete the stuffer fragment (FIG. 16). The resulting plasmid pAMH111 including egl1 gene between the promoter and terminator of cbh1 gene was cotransformed with p3SR2 to *T. reesei* QM 9414 (ATCC 26921) in a 5:1 molar ratio, respectively. The transformants were selected for AmdS+ phenotype and further purified on selective medium. Six individual transformants were grown for 4 days in cellulase inducing medium (Solka floc as a carbon source, 1%) in 50 ml liquid cultures. The culture supernatants were then tested for endoglucanase activity by measuring the release of reducing sugars from hydroxyethylcellulose (0.1%, ref. 12). The EG I activities of transformants were compared to a control (QM 9414) and the best transformant was shown to secrete 4 times the endoglucanase activity of the control strain. This example shows that it is possible to modify the amounts of different cellulolytic enzymes in *T. reesei* by changing the respective promoter.

Example 13

Construction of the expression vector for kappa light chain

Figure 22:
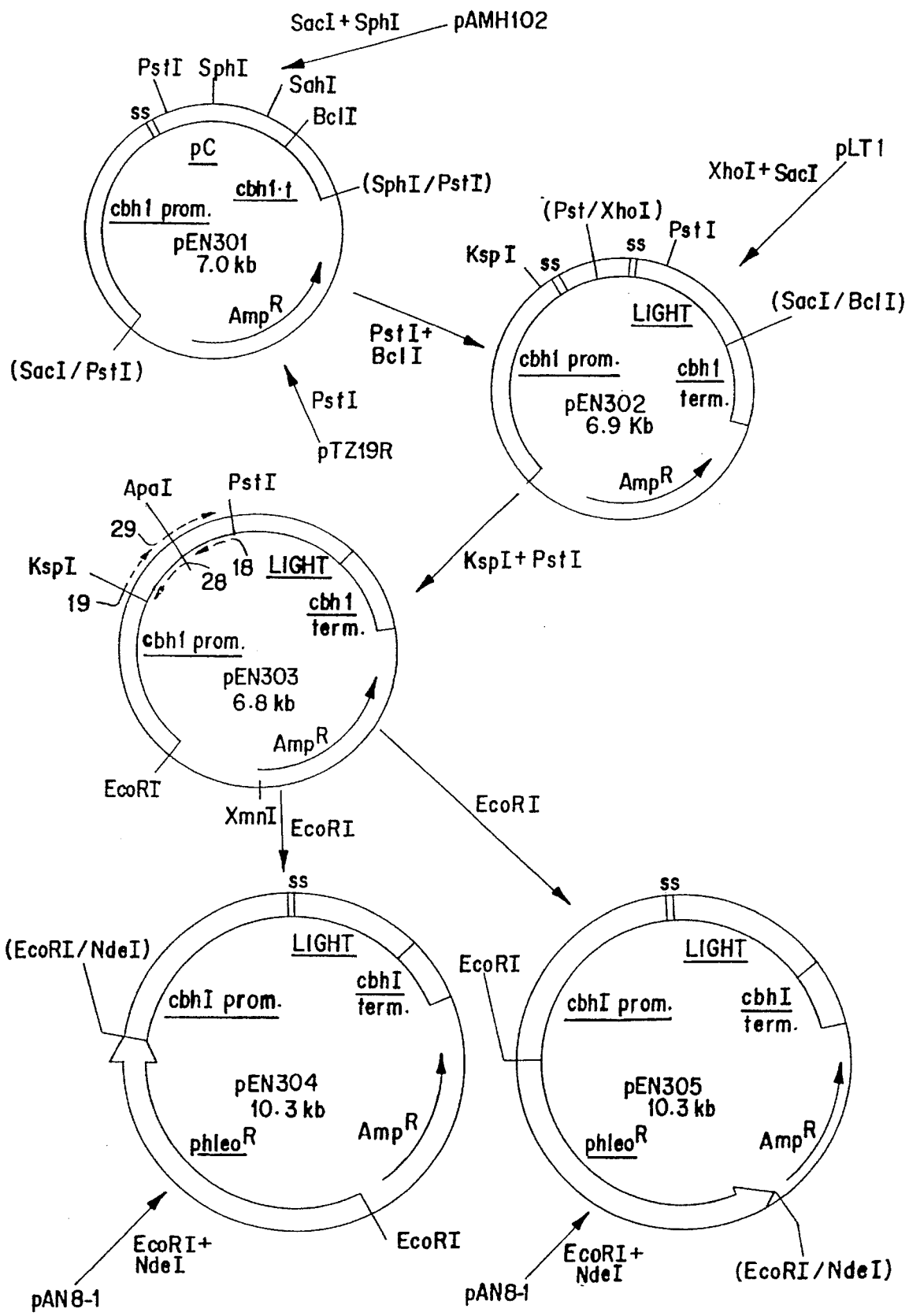
FIG. 22 diagrams the construction of plasmids pEN304 and pEN305, fungal expression vectors for the light chain cDNA.

Construction was made in four steps, resulting in vectors, pEN301, pEN302, pEN303, pEN304 and pEN305 (FIG. 22).

I. Joining of a fungal expression cassette to an *E. coli* vector

To build plasmid pEN301, a chymosin expression cassette (~4200 bp) was cut out from plasmid pAMH102 by SacI and partial SphI digestion. Plasmid pTZ19R (2860 bp; Pharmacia) was linearized by PstI digestion. Ends of both fragments were made blunt by mung bean nuclease treatment. The blunt ended SacI—SphI-fragment was ligated to the blunt ended PstI opened vector. The resulting plasmid was termed pEN301.

II. Substitution of chymosin cDNA by light chain cDNA

Figure 18:
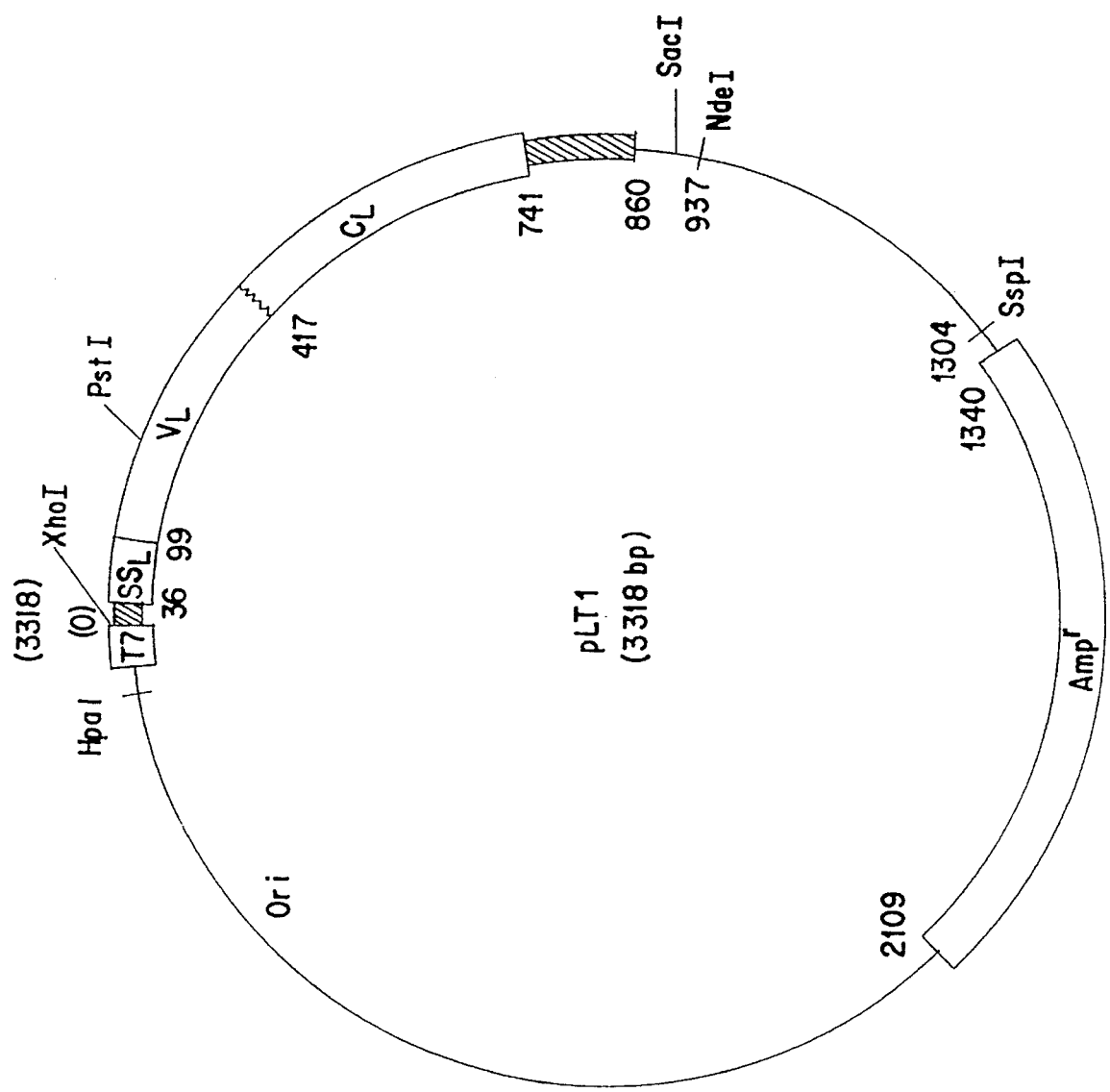
FIG. 18 is a diagram of plasmid pLT1 which carries a subclone of the light chain cDNA.

Plasmid pEN301 was cut with PstI and BclI to give a 5.9 kb vector. The light chain cDNA insert was cut from pLT1 (FIG. 18) by XhoI—SacI digestion (896 bp). Fragment ends were made blunt (mung bean nuclease) and ligated to form plasmid pEN302 (6.9 kb).

III. Making an exact joint: cbh1 signal sequence—light chain cDNA

Polymerase chain reaction (PCR) method was used to delete 198 bp between the cbh1 signal sequence and the light chain cDNA by creating new ApaI sites. The primers used are depicted in FIG. 22 on plasmid pEN303 and are identified by their size in nucleotides. 83 bp fragment was amplified by using one oligo (19 nt) with a KspI site that could hybridize to the promoter region and another oligo (28 nt) with an ApaI site in the junction between the signal sequence and the light chain cDNA. The ApaI site was created by changing the sequence CGTGCT to CGGGCC at the end of the cbh1 signal sequence, retaining the codons for Arg and Ala. The other fragment (88 bp) was created by using one oligo (29 nt) from the junction area, with an ApaI site and another oligo (18 nt) having a PstI site (within the light chain cDNA). The 83 bp fragment was digested with KspI and ApaI, the 88 bp fragment was digested with ApaI and PstI. The fragments were ligated at their ApaI sites to create a 132 bp fragment, which was then ligated to the KspI-PstI opened vector pEN302. The new joint was checked by sequencing. The plasmid is referred as pEN303.

IV. Adding a fungal marker, phleomycin resistance cassette, to the light chain expression vector Plasmid pAN8-1 (Mattern, I. E., Punt, P. J., Unkles, S. Pouwels, P. H. and van den Hondel, C. A. M. J. J., Transformation of *Aspergillus oryzae*. In: *Abstracts of the 19th Lunteren lectures on Molecular Genetics of Yeasts and Filamentous Fungi and its Impact on Biotechnology*, Lunteren, the Netherlands (1987), 34) was cut with EcoRI—NdeI to release a 3.5 kb phleomycin resistance cassette from the vector. Plasmid pEN303 was cut with EcoRI and the 6.8 kb fragment was isolated. Fragments were first ligated at their EcoRI sites. Ends of the 10.3 kb product were filled in with Klenow and the fragment was circularized by ligation. The resulting plasmid pEN304, had the phleomycin cassette in the same orientation as the light chain expression cassette.

Plasmid pEN305 had the expression cassettes in the opposite orientation to each other.

Example 14

Construction of the expression vector for the cbh1—heavy chain fusion protein

Figure 23A:
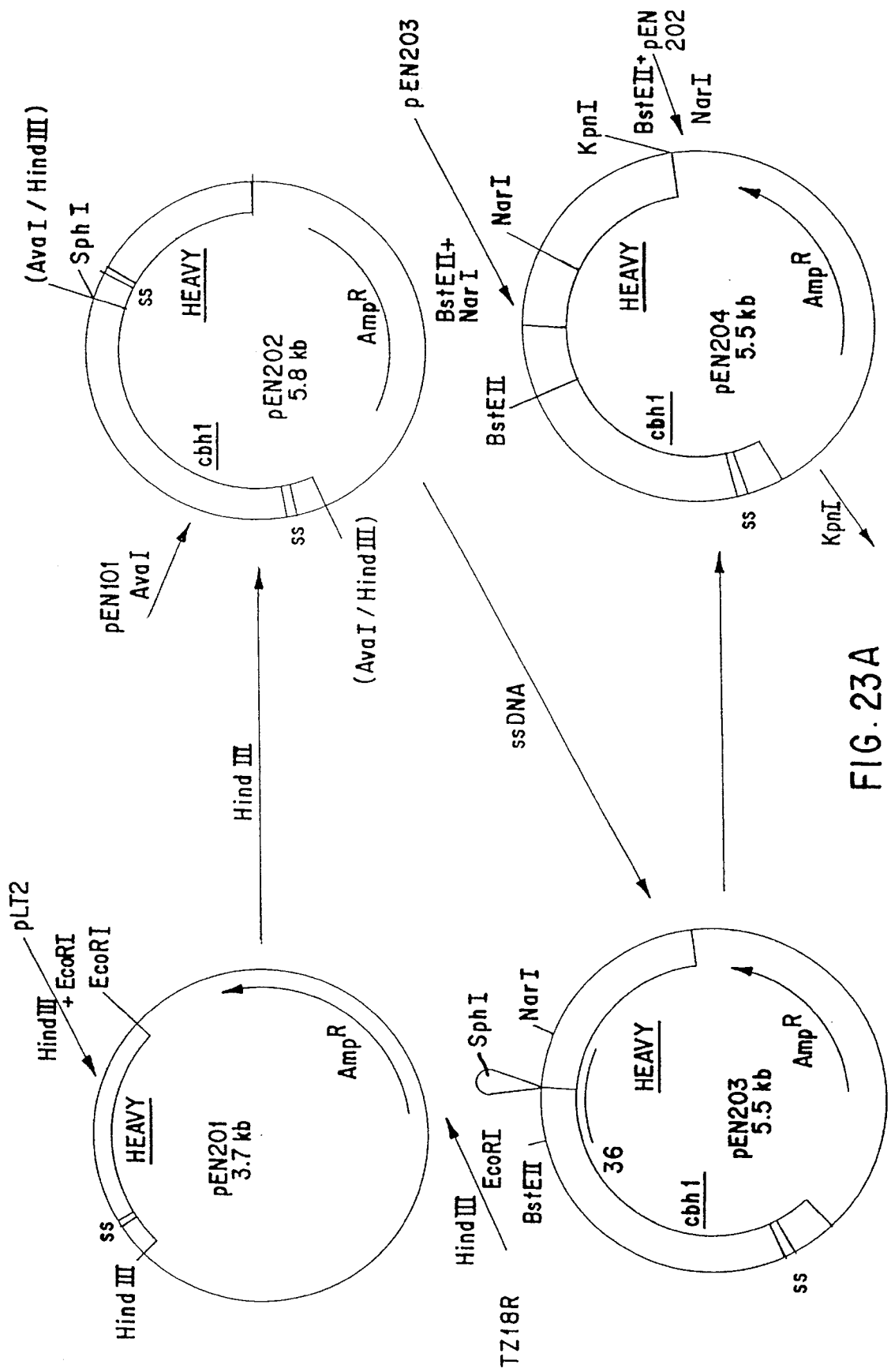
FIG. 23 diagrams the construction of plasmid pEN207, an intermediate vector for construction of plasmid pEN209.
Figure 23B:
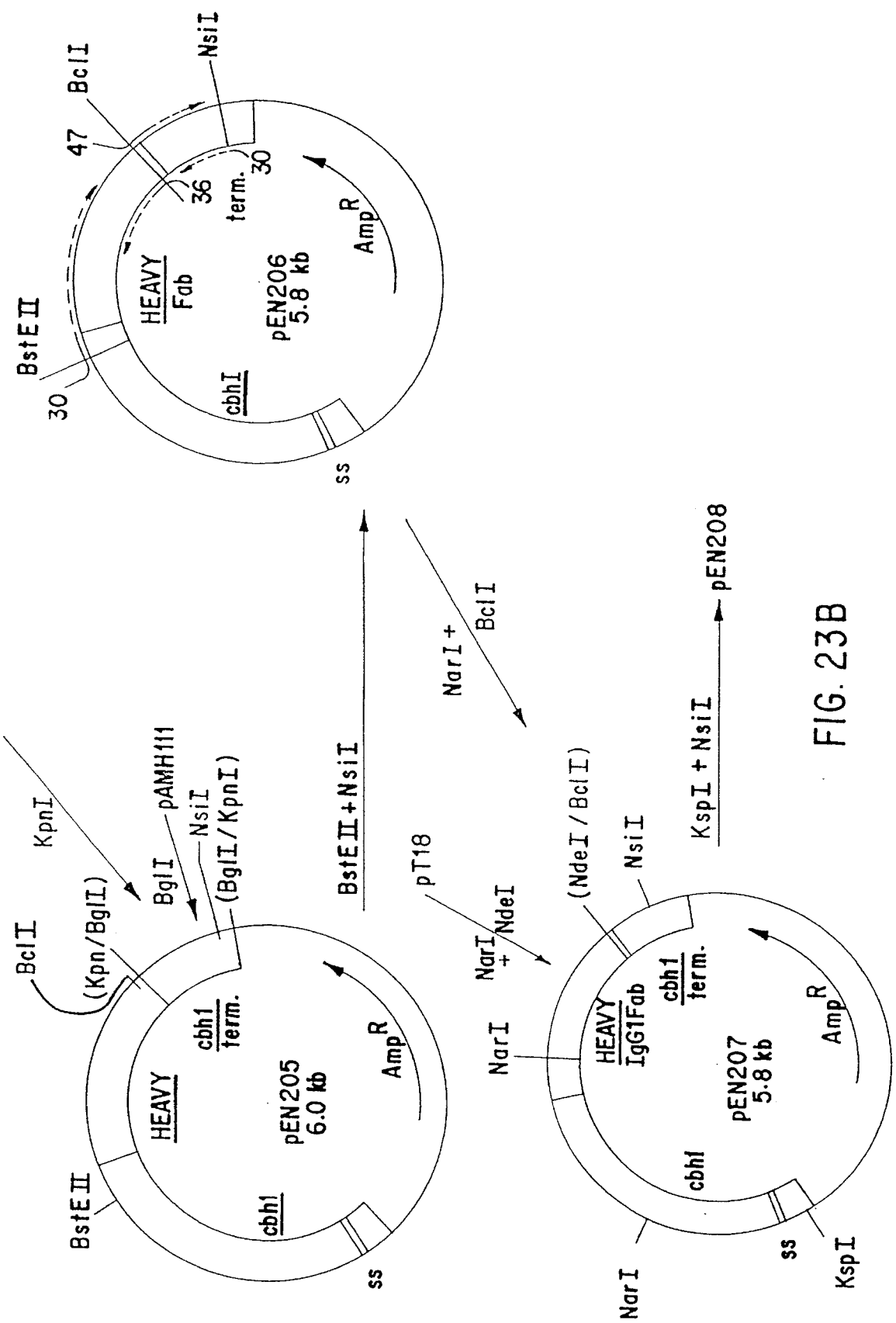
Figure 24:
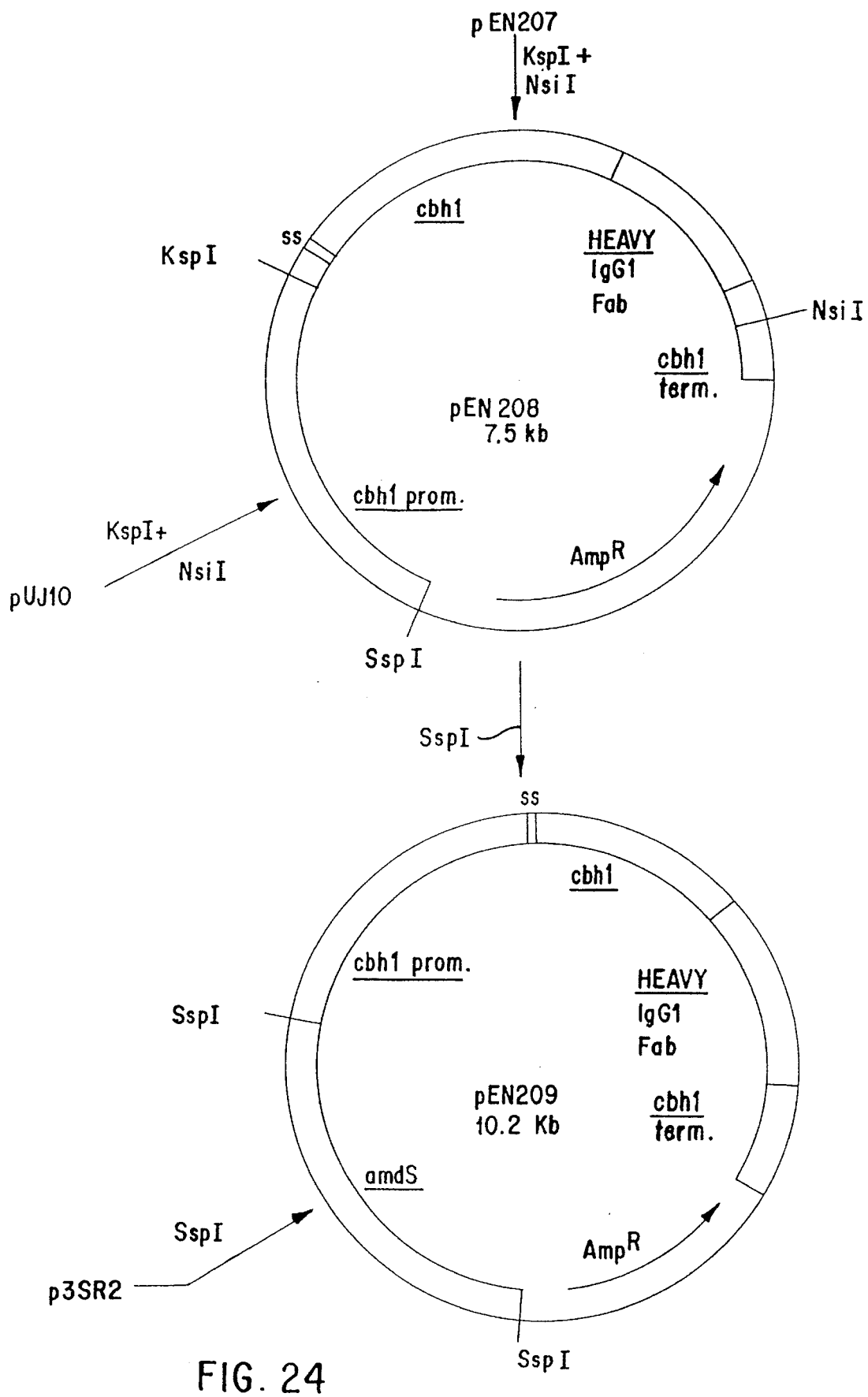
FIG. 24 diagrams the construction of plasmid pEN209, an expression vector for the cbh1—heavy chain Fab fusion.

The construction was made in nine steps, resulting in plasmids from pEN201 to pEN209 (FIG. 23, FIG. 24).

I. Linking the heavy chain cDNA to a vector

Figure 19:
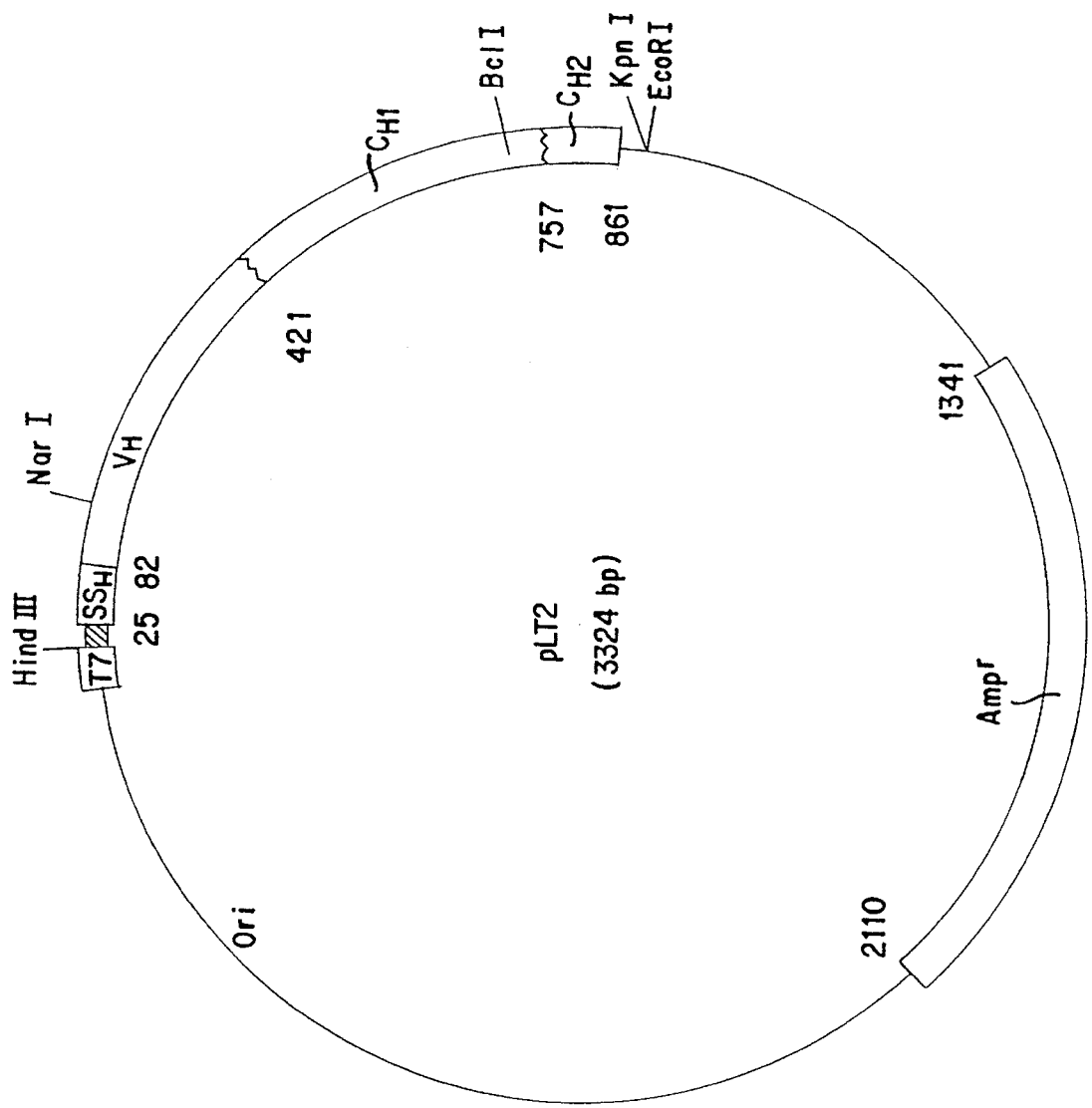
FIG. 19 is a diagram of plasmid pLT2, which carries a subclone of the IgG3 heavy chain cDNA ($V_H$, $C_H$, partly $C_{H2}$).

A gene coding the heavy chain (IgG3) was cut from plasmid pLT2 (FIG. 19) by HindIII and EcoRI, resulting a 870 bp insert, which was ligated to HindIII—EcoRI opened plasmid pTZ18R (2.8 kb; Pharmacia). The resulting 3.7 kb plasmid is referred as pEN201.

II. Adding the chromosomal cbh1 gene to the 5' site of the heavy chain cDNA.

Figure 21:
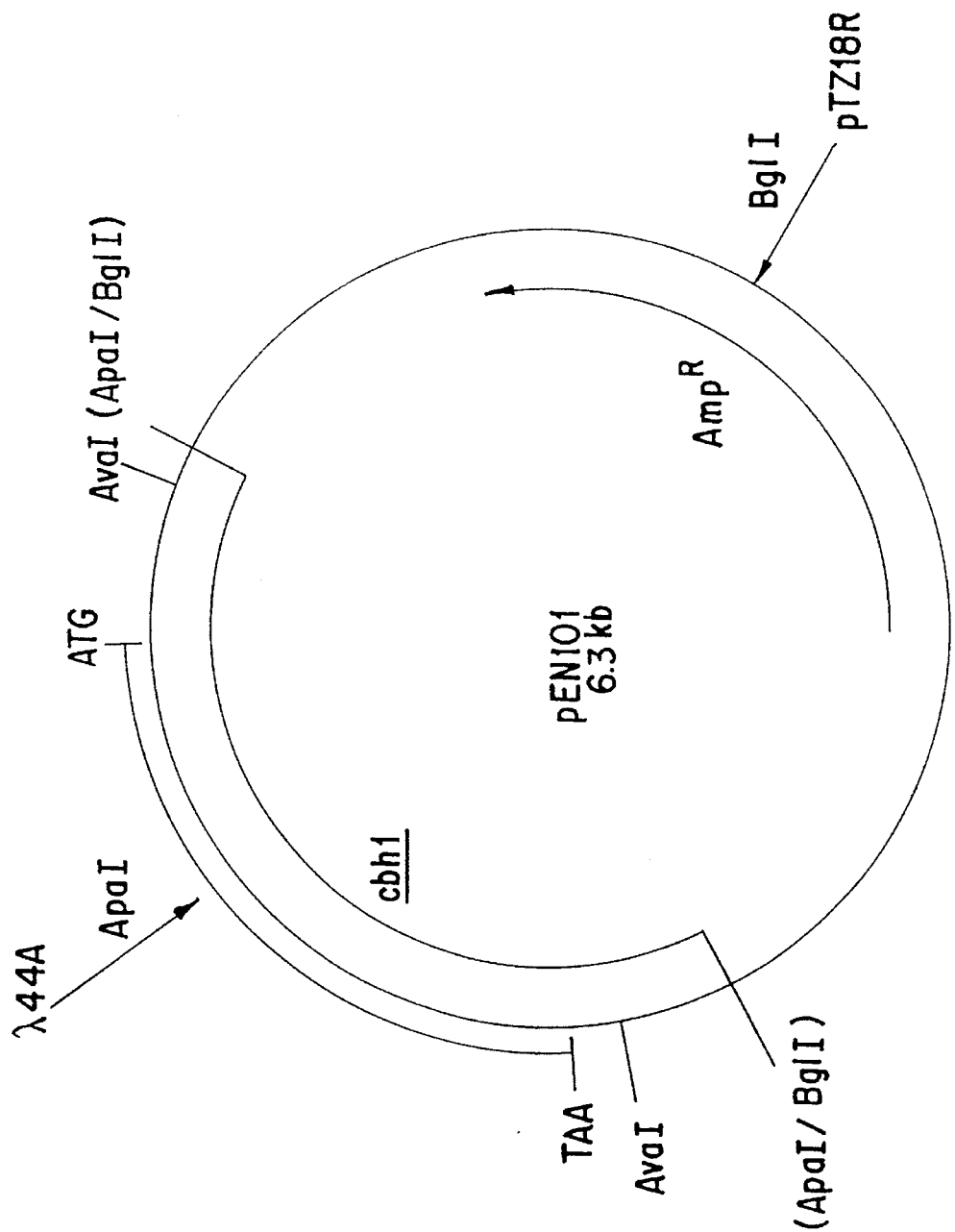
FIG. 21 is a diagram of plasmid pEN101, which carries a subclone of the chromosomal cbh1 gene.

Plasmid pEN202 (5.8 kb) was build by cutting the chromosomal cbh1 gene from pEN101 (FIG. 21) with AvaI (2.1 kb). (Plasmid pEN101 is a subclone, where the chromosomal cbh1 gene was removed from λ44A clone (Teeri, T., Salovuori I. & Knowles, J., The molecular cloning of the major cellulase gene from *Trichoderma reesei* BIO/TECH-NOLOGY 1: 696–699(1983)) to plasmid pTZ18R. Lambda DNA was cut with ApaI and pTZ18R opened by BglI—fragments were treated with mung bean nuclease before ligation). Plasmid pEN201 was opened with HindIII (3.7 kb). Both fragments were blunt ended by mung bean nuclease before ligation.

III. Making an exact joint between the cbh1 and the heavy chain

The aim was to fuse a large part of the efficiently secreted CBHI protein (corresponding to amino acids 1–484) to the heavy chain in order to facilitate the secretion of the heavy chain from the Trichoderma host cell. In all fusion protein constructs in which a signal sequence is joined to an immunoglobulin sequence, it is necessary to construct such fusions so as not to alter the translational reading phase of the immunoglobulin RNA sequence. In addition, as this CBHI fragment was meant to serve only as a secretion "carrier," that is, a secretion signal, and its secretion-promoting functions are not needed in the final product, a Factor Xa recognition site was added between the two regions to allow the CBHI part to be easily proteolytically removed after secretion by methods known in the art. An exact joint was made by deleting 265 bp. A single stranded DNA preparation of pEN202 was made with help of phage: M13K07. A 36 nt long oligonucleotide, which contained the exact joint, was hybridized to the single stranded DNA. Using the oligonucleotide as a primer the plasmid was made double stranded with dNTPs, Klenow polymerase and ligase. Double stranded DNA mixture was digested with SphI (site in the loop; single site in the plasmid), to enrich the deleted plasmids. Digested DNA mixture was transformed to JM109, and the whole pool of transformants was grown in liquid medium. A DNA preparation was made from the pool, and the mixture was digested with SphI—again to enrich the correct plasmids. Digested mixture was transformed to JM109. Correct clones were identified by sequencing the joint area. The resulting plasmid is referred as pEN203 (5.5 kb).

IV. Moving the joint area to a clean background

Mistakes can easily occur in elongation done in vitro. To avoid any mistakes in the construction, the sequenced and correct joint area (190 bp) was cut out from pEN203 by BstEII—NarI digestion and moved to the clean background: to BstEII—NarI opened plasmid pEN202. The resulting plasmid was referred as pEN204.

V. Adding a fungal terminator to the construction

A 476 bp long cbh1 terminator was cut out from plasmid pAMH111 by BglI digestion. Plasmid pEN204 (5.5 kb) was opened by KpnI. Fragment ends were blunt ended by mung bean nuclease treatment before ligation. The plasmid is referred as pEN205 (6.0 kb).

VI. Making an exact joint between the heavy chain and the cbhI terminator

The heavy chain cDNA in the construction thus far consists of V, C1, hinge and part of C2 region. When making Fab molecules, the translation stop signal has to be placed after C1 region. Deletion (235 bp) of the heavy hinge and the C2 region and fusion of the cbh1 transcription terminator with its translation stop signal to the end of C1, was accomplished by using PCR method. The primers used are depicted in FIG. 23 on plasmid pEN206 and are identified by their size in nucleotides. A 890 bp long sequence was amplified by PCR by using a 30-mer hybridizing to the cbh1 gene and having a BstEII site in it and another 30-mer hybridizing to the end of heavy CI and having a BclI site in it. Another ~240 bp fragment was made, where a 47-mer hybridizing to the cbh1 terminator region and having a BclI site in it and one 30- hybridizing further down in the terminator and having a NsiI site in it. The first amplified fragment was cut with BstEII and BclI, the other with BclI and NsiI. The fragments were ligated at their BclI sites, between which the deleted sequence is located, and the formed ~1100 bp fragment was ligated to BstEII—NsiI opened plasmid pEN205. The PCR made region in the resulting plasmid was sequenced and the plasmid is referred as pEN206.

VII. Exchanging the IgG3 heavy chain cDNA to the IgG1 heavy chain cDNA

To make the exchange of the IgG3 heavy chain cDNA to the IgG1 heavy chain cDNA, a 640 bp long IgG1 heavy chain cDNA was cut out from plasmid pTI8 (FIG. 20) by NarI—NdeI digestion. Plasmid pEN206 was cut with NarI and BclI (5.2 kb). The fragments were ligated at their NarI sites. The fragment ends were made blunt (mung bean nuclease) and ligated to form a 5.8 kb plasmid pEN207.

VIII. Adding the cbh1 promoter to the construction

Plasmid pEN207 was digested by KspI (=SacII) and NsiI digestion. The cbhI promoter was cut from plasmid pUJ10 (FIG. 26) with KspI and NsiI. A 2.5 kb fragment from pEN207 was ligated to a 5.0 kb fragment from pUJ10 to form a 7.5 kb plasmid pEN208.

XI. Adding a fungal marker, amdS, to the construction

The amdS expression cassette was cut from plasmid p3SR2 (Cabilly, S., et al., EP 125,023; Kaiser, C. A., et al., *Science* 235:312–317 (1987)) with SspI, resulting a 2.7 kb insert, which was ligated to the SspI opened plasmid pEN208 (7.5 kb). The resulting 10.2 kb plasmid was referred as pEN209.

Example 15

Construction of expression vector for the IgG1 heavy chain

I. Removing the cbh1 gene from fusion vector pEN207

Figure 25:
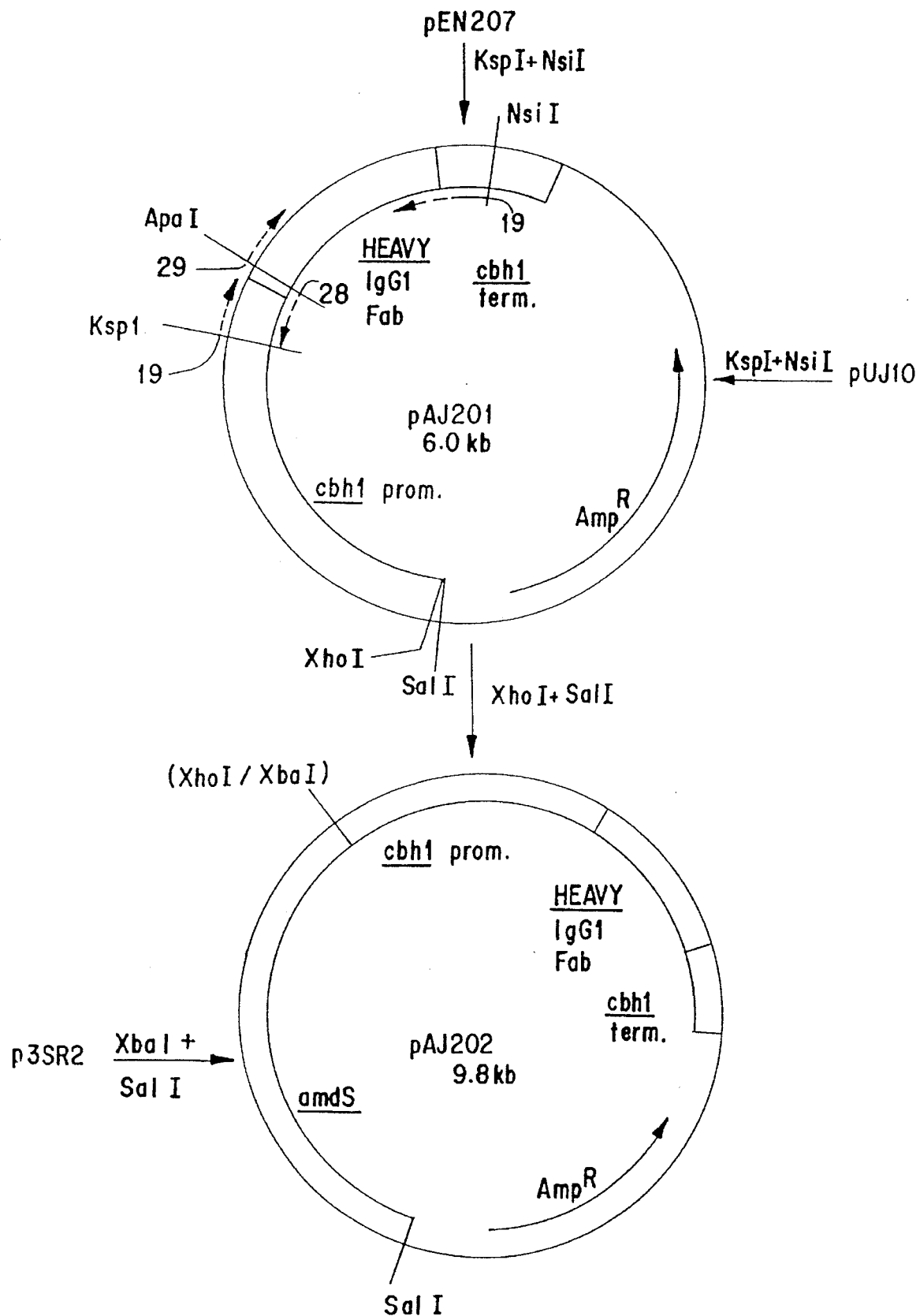
FIG. 25 diagrams the construction of plasmid pAJ202, an expression vector for the heavy chain Fab cDNA.

The cbh1 gene (1533 bp) was deleted from plasmid pEN207 by using PCR. The primers are depicted in FIG. 25 on plasmid pAJ201 and were identified by their size in nucleotides.

An 83 bp fragment was amplified by using an oligo (19 nt) with a KspI site that hybridized to the cbh1 promoter region and another oligo (28 nt) with an ApaI site in the junction between signal sequence and heavy chain gene. The ApaI site was created by changing the sequence CGTGCT to CGGGCC at the end of the cbh1 signal sequence, so that the codons for Arg and Ala were retained. The other fragment (943 bp) was created by using one oligo (29 nt) from the junction area, with an ApaI site and another oligo (19 nt) having a NsiI site (within the cbh1 terminator). The 83 bp fragment was digested with KspI and ApaI, the other (943 bp) fragment was digested with ApaI and NsiI. The fragments were ligated at their ApaI sites to create an approximately 1000 bp fragment, which was then ligated to KspI—NsiI opened vector pUJ10 (FIG. 26). The new joint was checked by sequencing. The plasmid is referred as pAJ201 (6.0 kb).

II. Adding a fungal marker, amdS, to the construction

Plasmid pAJ201 (6.0 kb) was opened by SalI-XhoI digestion. The amdS expression cassette from p3SR2 was cut with XbaI—SalI (3.8 kb). Fragments were ligated at their SalI sites. Ends of the 9.8 kb product were filled in with Klenow and the plasmid was circularized by ligation to result plasmid pAJ202 (9.8 kb).

Example 16

Expression of the light chain

Trichoderma reesei strain RUT-C-30 (ATCC 56765) was transformed with expression vectors for the light chain, pEN304 and pEN305 (both have phleomycin$^R$ marker). A cotransformation was also made, where plasmid pEN303 (no marker) and plasmid pAN8-1 (containing the phleomycin resistance gene) were both transformed into RUT-C-30 at the same time. Transformation in Trichoderma may be made using a standard *T. reesei* transformation method (Penttilä, M., Nevalainen, H., Ratto, M., Salminen E. & Knowles, J., *A versatile transformation system for the cellulolytic filamentous fungus Trichoderma reesei* Gene 61:155–164 (1987)) which is based on the use of selection markers amdS and argB. The same system can be used to select routants with the trpC marker. In this experiment, transformants were selected by phleomycin resistance.

Two different kinds of plate/overlay media were used. One was based on *T. reesei* minimal medium, where $KH_2PO_4$, was substituted by $K_2HPO_4$, and 0.44M sucrose was added as osmotic stabilizer. The other, rich medium (MnR) consisted of 0.3 g K-phtalate, 2.5 g yeast extract, 2.5 g glucose and 150 g sucrose/liter. In both media pH was adjusted to 7 to avoid breakage of phleomycin. In bottom medium 1.5% agar and in overlays 0.6% agarose was used as a solidifying agent.

After transformation the protoplasts were plated and incubated 2–3 h at room temperature, after which 5 ml of phleomycin (Cayla, France) containing overlay was added to the plates. Two phleomycin concentrations were used, 35 µg/ml or 50 µg/ml total plate medium. A fresh stock (30 mg/ml) of phleomycin was made in sterile water.

Transformation plates were incubated at +28° C. for 5–7 days, after which the transformants were picked and grown on slants in MnR+100 µg/ml phleomycin either for three cycles, one week each (pEN304 and pEN305), or just for one cycle/one week (pEN303—pAN81) to select for stable transformants.

Before screening, the transformants were transferred to PD slants (Potato Dextrose Agar) for better sporulation. Spores were suspended to 5 ml 0.9% NaCl per slant and transferred to 50 ml of liquid medium (*T. reesei* minimal medium supplemented with 2% Solca Floc cellulose and 1% spent grain, pH 5.0). Transformants were grown in shake flasks for four days at +28° C. shaking in 160 rpm. The best producers were cultivated in 500 ml medium (inoculum from two slants) for five days and 250 rpm. Culture medium was separated from mycelia by either filtration or centrifugation (3000 g). From filtrations the mycelia were collected for Southern analysis.

Production of light chain was screened from culture medium by using ELISA test. Microtiter plates were coated with a purified IgG fraction of anti-Ox IgG3 Fab antiserum (Department of Bacteriology and Immunology, University of Helsinki). 100 µl of anti-Ox-I Fab antibody, 7.5 µg/ml in 0.1M bicarbonate buffer, pH 9.6, was pipetted to the wells and incubated overnight at +4° C. The wells were washed between every step with 100 µl 50 mM phosphate buffer, pH 7.4–0.9% NACl (PBS). 0.5% BSA in PBS was used for one hour in room temperature to block the uncoated regions. Culture supernatant samples (100 µl) were added to microtiter wells, both undiluted and in 1:20 dilution in 0.5% BSA in PBS. Purified Fab molecules derived from mouse ascites fluid, 1–10 ng, were used as standards and diluted into RUT-C-30 culture medium or 0.5% BSA in PBS. Samples were incubated at room temperature for two hours. Secondary antibody: goat anti-mouse kappa-alpha (alkaline phosphatase; Southern Biotechnology Associates, Inc.) was added in 1:500 dilution to the wells and incubated for one hour at room temperature. The substrate used for color reaction was 2 mg di-Na-salt of p-nitrophenylphosphate (Orion company, Helsinki) per one ml of diethanolamine-$MgCl_2$-buffer (Orion). The wavelength used for absorbance measurement was 405 nm.

The amount of secreted light chain (pEN304/RUT-C-30) was 200 µg/l of culture medium (500 ml cultivation), when approximated from EL1SA test. Light-chain producing *T. reesei* strain was deposited as accession number CBS 252.90 on Jun. 25, 1990 at the Centraalbureau voor Schimmelcultures, P.O. Box 273; Oosterstraat 1, 3740 AG Baarn, The Netherlands.

Preliminary integration studies were done, in which culture supernatants were blotted to a nitrocellulose filter. The filter was blocked with 0.5% milk in TBS (20 mM Tris, pH 7.5–500 mM NaCl) and incubated with monoclonal anti-CBHI antibody (1:50 in TBS) (CH5 provided by Professor C. P. Kubicek, Institut fur Biochemische Technologie und Microbiologie, Wien, Austria). Secondary antibody used was anti-mouse polyvalent immunoglobulins alkaline phosphatase conjugate (Sigma). The filter was stained by the Protoblot Immunoblotting System (Promega Biotec.). Positive signal was found for the control strain (RUT-C-30) only, which indicates that both of the two positive, light chain producing transformants (out of 130 transformants screened) have their light chain expression cassette integrated into cbh1 locus.

Example 17

Expression of the cbh1—heavy chain fusion

The heavy chain construction, pEN209 (amdS marker), is transformed to *Trichoderma reesei* strain RUT-C-30. Plasmids pEN208 (no marker) and p3SR2 are cotransformed to RUT-C-30. Transformants are selected by their ability to use acetamide as their sole nitrogen source.

Plate and overlay medium used in transformation is *T. reesei* minimal medium, in which 0.5% ammonium sulfate is substituted by 12 mM acetamide. 15 mM CsCl is added to inhibit background growth. The osmotic stabilizer used is 1M sorbitol.

From transformation plates, after 8–10 days from plating, transformants are removed to PD slants for sporulation.

Transformants are grown in shake cultivations and tested by ELISA test and western analysis as described in example 4.

Example 18

Expression of the heavy chain

The heavy chain construction pAJ202 is transformed to strain RUT-C-30, and selected for AmdS$^+$ phenotype.

Procedures used are as described in examples 16 and 17.

Example 19

Expression of the different forms of antibodies

I. Fungal transformations

Heavy chain constructions, pEN209 and pAJ202, were transformed to the light chain expressing parent strain. Transformants were screened for AmdS$^+$ phenotype for their ability to use acetamide as their sole nitrogen source. *T. reesei* transformants, pEN304/pEN209 and pEN304/pAJ202, were deposited as accession numbers CBS 287.91 (on Jun. 3, 1991) and CBS 288.91 (on Jun. 3, 1991), respectively, at the Centraalbureau voor Schimmelcultures P.O. Box 273, Oosterstraat 1, 3740 AG Baarn, The Netherlands.

Cotransformations were also made, in which pEN208 (no fungal marker)/pEN304 (marker: phleomycin resistance) and pAJ201 (no fungal marker)/pEN304 were transformed and screened for their phleomycin resistance.

Transformations were carried out as described earlier in Examples 16 and 17.

II. Screening of the Antibody Producing Transformants

Transformants were cultivated in 50 ml of liquid medium (*T. reesei* minimal medium supplemented with 3% whey and 1.5% spent grain, pH 5.0). Transformants were grown in shake flasks for four days at 28° C., 200 rpm.

Production of antibodies was screened from culture supernatants by using the ELISA test as described in Example 16.

ELISA was also used for measuring the immunoreactivity of the Fabs produced. Microtiter plates were coated with the hapten i.e., phenyloxazolone conjugated to BSA (Mäkelä, O., Kaartinen, M., Pelkonen, J. L., and Karjalainen, K., *Inheritance of Antibody Specificity V. Anti-2-Phenyloxazolone in the Mouse, J. Exp. Med.* 48:1644–1660 (1978)). Ox-BSA was used in 50 µg/ml concentration in 0.1M bicarbonate buffer, pH 9.6. Otherwise, the ELISA test was carried out as described in Example 16.

The yield of secreted Fab and CBHI-Fab of the best transformants was about 0.8 mg/l and about 45 mg/l, respectively, when approximated for immunoreactivity from ELISA test.

III. Preliminary Fermentations

Two transformants, Fab and CBHI-Fab producing, were fermented. The medium contained, in g/l: Whey 60; spent grain 30; (NH$_4$)$_2$SO$_4$ 6; KH$_2$PO$_2$ 3. Initial pH was 4.8 without adjustment. The inculum was grown on half-strength medium (buffered with 15 g/l KH$_2$PO$_4$) in two stages of 1×200 ml for two days and 5×200 ml for one day. The fermenter used was a Chemap CF 2000 bioreactor, working volume 15 l+1 l inoculum and with automatic control of temperature (33° C. for 48 h, subsequently 29° C.), pH (between 4.0 and 5.5 was controlled by NH$_4$OH and H$_3$PO$_4$) and pO$_2$.

Samples were collected daily and growth medium and mycelia were separated by filtration through GF/B microfibre filters (Whatman). The mycelia were washed with 0.9% NaCl. The samples were stored at −20° C.

Fermentations were continued for four and five days for Fab and CBHI-Fab producing strains, respectively. The growth medium and mycelia were separated by centrifugation and the growth medium was clarified by adding 50 g/l silica, mixing and filtering through GF/B micro fiber filters (Whatman) before storing at −20° C.

The supernatants were screened for antibody production by ELISA and western analysis. According to ELISA, the amount of produced, immunoreactive Fabs and CBHI-Fabs were 0.5 mg/l (the fourth day) and 150 mg/l (the fifth day, level was slightly better on the fourth day), respectively. The amount of total protein (Lowry) in Fab/RUT-C-30 fermentation was 9.3 g/l and in CBHI-Fab/RUT-C-30 6.5 g/l.

IV. Purification Of the CBH)-Fab Fusion Protein

Protein purification was made only from the fusion protein growth medium, because of the better antibody yield. Purification was performed in the three major steps. An anion exchange separation was used as a crude purification step. Affinity chromatography, in which hapten was used as a ligand, resulted in a pure antibody preparation. Gel filtration was used as a last step to separate autoproteolytically cleaved, Fab resembling antibody from the original fusion antibody.

CBHI-Fab protein containing fermented growth medium was transferred to the starting buffer, 10 mM sodium phosphate buffer, pH 7.2, through Sephadex G-25 (coarse) for subsequent ion exchange chromatography. For crude purification an anion exchange chromatography was done using DEAE-Sepharose FF. Elution was achieved by increasing NaCl molarity, from 100 mM NaCl to 1M NACl. CBHI-Fab behaved in the anion exchange chromatography like the wild-type CBHI, i.e, the fusion antibody was eluted with high salt.

Pooled and concentrated sample was dialyzed against 10 mM Tris-HCl, pH 7.5–0.9% NACl, the starting buffer for affinity chromatography. Ox-BSA was coupled to CNBr-activated Sepharose 4B (Pharmacia) in a ratio of 5 mg protein/ml gel. Affinity chromatography was performed as described (Harlow, E., and Lane, D., *Antibodies. A Laboratory Manual*, Cold Spring Harbor Laboratory, Cold Spring Harbor, N.Y. (1988)). Bound antibodies were eluted by 100 mM glycine-HCl, pH 2.5 and fractions were immediately neutalized by 0.25M Tris, pH 8.0.

CBH I-Fab preparation was contaminated by autoproteolytically cleaved, Fab resembling antibody. The two antibody forms were separated by gel filtration using Sephacryl S-200, the buffer used was 0.1M Tris-HCl, pH 7.2–0.2M NaCl. Samples were dialyzed against storage buffer, PBS, pH 7.4.

V. Characterization of the Purified Fusion Protein

Protein concentrations of the fusion and cleaved forms of antibodies were determined from the absorbance at 280 nm using calculated molar extinction coefficients at 280 nm based on the Trp and Tyr content of each protein sequence (167 760M$^{-1}$cm$^{-1}$ and 86 670 m$^{-1}$ cm$^{-1}$ for the fusion antibody and the cleaved antibody, respectively) (Wetlaufer, D. E., *Adv. Prot. Chem.* 17:303–390 (1962)).

Sizes of the antibody chains were verified by SDS-PAGE electrophoresis and western analysis. Protein samples were tested against anti-IgG1 (Southern Biotechnology Associates, Inc.) and anti-CBHI core (CHS, provided by C. P. Kubicek). The size of the fusion heavy chain is about 86 kD, its cleaved counterpart is about 24 kD, the same as the size of the nonfused Fab heavy chain. Size of light chain is 23 kD.

Immunoreactivity of the fusion and cleaved antibodies were tested on the ELISA. The autoproteolytically cleaved antibody and the authentic proteolytically digested Feb derived from ascites were 27 times more active on binding oxazolone than the original fusion antibody.

The N-terminal amino acid sequence of the purified fusion and cleaved antibodies was determined on an Applied Biosystems 477A on line 120 A modified pulsed liquid phase/gas phase sequencer (Baumann, M., *Comparative Gas Phase and Pulsed Liquid Phase Sequencing on a Modified Applied Biosystems 477A Sequencer, Anal. Biochem.* 190:198–208 (1990)). The N-termini of the chains have been correctly processed. The cleavage of the fusion has occurred two amino acid residues before the authentic N-terminus of the heavy chain. The cleavage after tyrosine residue implies the existence of low chymotrypsin like protease activity in Trichoderma growth medium. Only about 0.02% of the fusion was cleaved immediately after fermentation (fifth day) according to the ELISA results from ion exchange fractions, in which cleaved antibody was eluted in the first fractions.

Example 20

Construction and Expression of Single Chain Antibody

Figure 29:
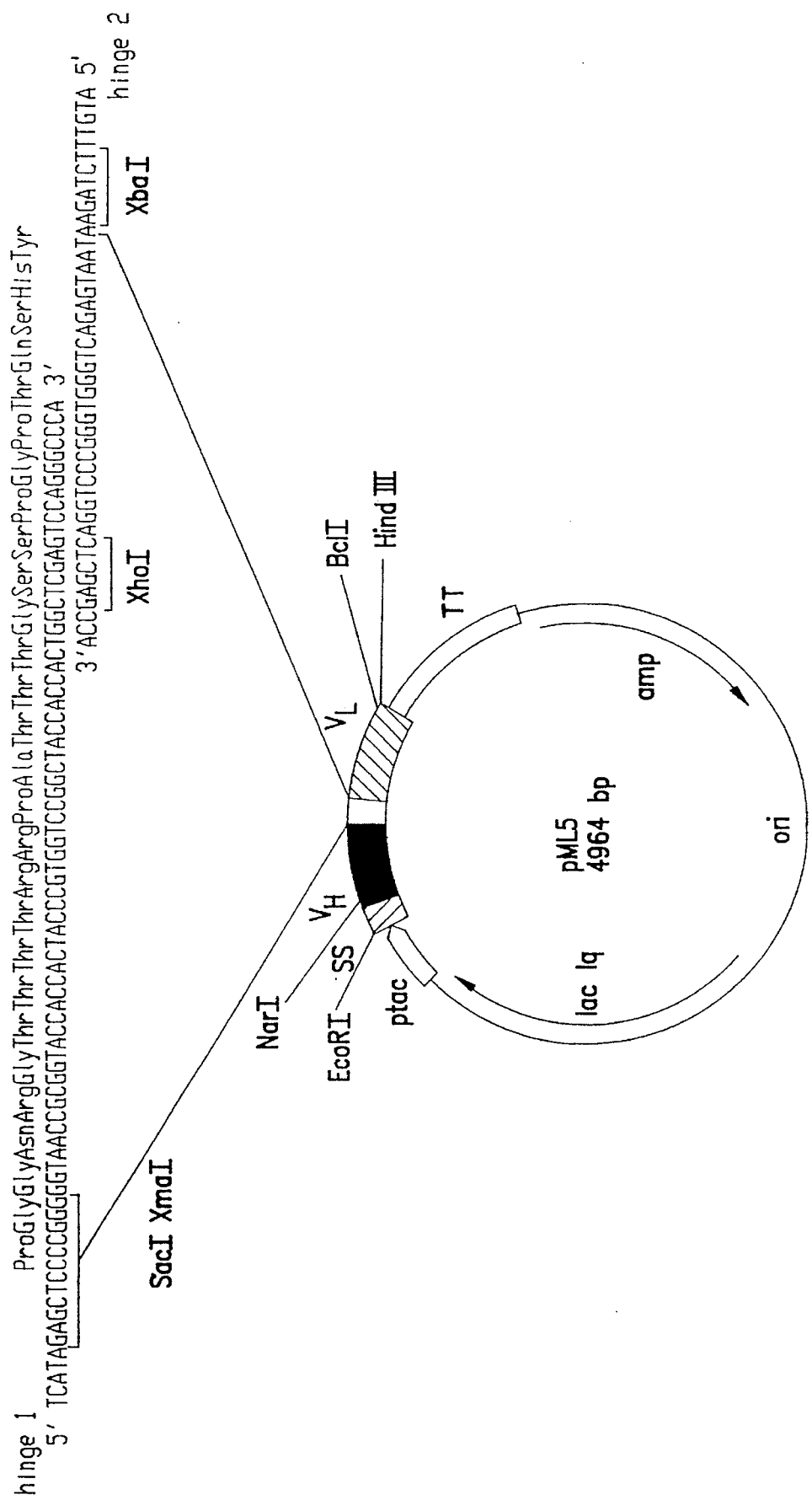
FIG. 29 diagrams the elements of plasmid pML5, which carries a structural gene of single chain antibody, having cbh1 hinge as a linker.

A single chain antibody (SCA) containing variable regions of both light and heavy chains linked to each other by a flexible hinge region of CBHI was used. Construction of the functional gene was as described in Teeri, T., Takkinen, K., Laukkanen, M.-L., Alfthan, K., Sizmann, D., and Knowles, J. K. C., *Recombinant secretable fusion proteins*. U.S. Utility patent application, Ser. No. 07/552,751; filed Jul. 16, 1990. The structure of the functional gene is shown in FIG. 29. The regulatory regions were rebuilt for Trichoderma expression.

The SCA encoding gene was amplified from plasmid pML5 (FIG. 29) by PCR, using a 15 mer oligo binding to the heavy chain $V_H$-region on both sides of NarI site, and a 24 mer having the end of $V_L$-region, STOP codon and created BclI site in the end. PCR amplified 730 bp fragment was digested with NarI and BclI. Plasmid pAJ201 was cut by NarI-BclI digestion. A 5.4 kb fragment of pAJ202 was ligated with a 730 bp PCR fragment to create a plasmid pEN401 (6.2 kb). SCA encoding gene is regulated by cbh1 promoter and terminator regions in plasmid pEN401.

The SCA encoding gene was also cloned under a promoter expressed on glucose, i.e., Aspergillus gpd promoter. The gpd promoter (1.2 kb) was amplified from plasmid pAN8-1. A 39 mer oligo was used from the 5' end of the published gpd promoter (Punt, J. P., Dingemanse, M. A., Kuyvenhoven, A., Soede, R. D. M., Pouwels, P. H., and van den Hondel, C. A. M. J. J., *Functional elements in the promoter region of the Aspergillus nidulans gpdA gene encoding glyceraldehyde-3-phosphate dehydrogenase, Gene* 93:101–109 (1990)) with created EcoRI and XbaI sites in the extreme 5' end. Second, 27 mer oligo bound to the 3' end of the gpd promoter with a change of CCCCGC (+151+ $_o$+156) to CCGCGG to create a KspI site. Amplified, XbaI-KspI digested gpd promoter was ligated with XbaI-KspI digested plasmid pEN401 to replace cbh1 promoter and create plasmid pEN402 (5.9 kb).

Plasmids pEN401 and pEN402 were transformed to RUT-C-30 strain by cotransformation using phleomycin resistance as a marker (pAN8-1).

Transformants were grown in shake flasks in 50 ml *T. reesei* minimal medium supplemented with 3% whey and 1.5% spent grain, pH 5.0. pEN402/RUT-C30 transformants were also cultivated in 50 ml *T. reesei* minimal medium supplemented with 2% glucose and 0.5% peptone, pH 5.0.

Expression of immunoreactive SCAs was tested from culture supernatants by ELISA using Ox-BSA coated microLiter wells as described in Example 19. Purified IgG fraction of rabbit anti-Ox IgG3 Fab antiserum was used as a first detection antibody (1:300). Second detection antibody layer was goat anti-rabbit IgG (H+L) alkaline phosphatase conjugate (Bio-Rad Laboratories).

Example 21

I. Cloning of the Light and Heavy Chain cDNA Fragments Encoding the Fab-Fragment of an Anti-2-Phenyloxazolone IgG3 Subclass Antibody The mRNAs of the light and heavy chain Ox IgG3 subclass antibody were isolated from hybridoma cell clone DHK-2, 6 (received from M. Kaartinen, Department of Bacteriology and Immunology, University of Helsinki, 00290 Helsinki 29, Finland).

The first strand of the cDNA was synthesized using specific primers. The light chain primer was complementary to the 3' noncoding region of the light chain mRNA containing a XbaI restriction site used in the cloning of the cDNA fragment. The heavy chain primer was complementary to the region of constant two domain containing a XbaI restriction site. The first strand cDNA synthesis was carried out as described by Maniatis e( al., *J. Molecular Cloning*: A Laboratory Manual, New York, Cold Spring Harbor Laboratory (1982). After alkaline hydrolysis of the mRNAs, the second strand synthesis for both light and heavy chain was carried out by using specific primers. The second strand primers of the light and heavy chain were identical with sequences of the 5' noncoding regions of the mRNAs and they both contained a SphI restriction site. After second strand synthesis the 3' ends of the cDNA fragments were trimmed with T4 DNA pol I as described in Maniatis et al. (1982). The blunt ended cDNA fragments of the light and heavy chain were first digested with SphI and XbaI restriction enzymes and then cloned into the pSP73 vector (Promega). The light chain cDNA clone was designated pLT1 and the heavy chain cDNA clone was designated pLT2.

Figure 20:
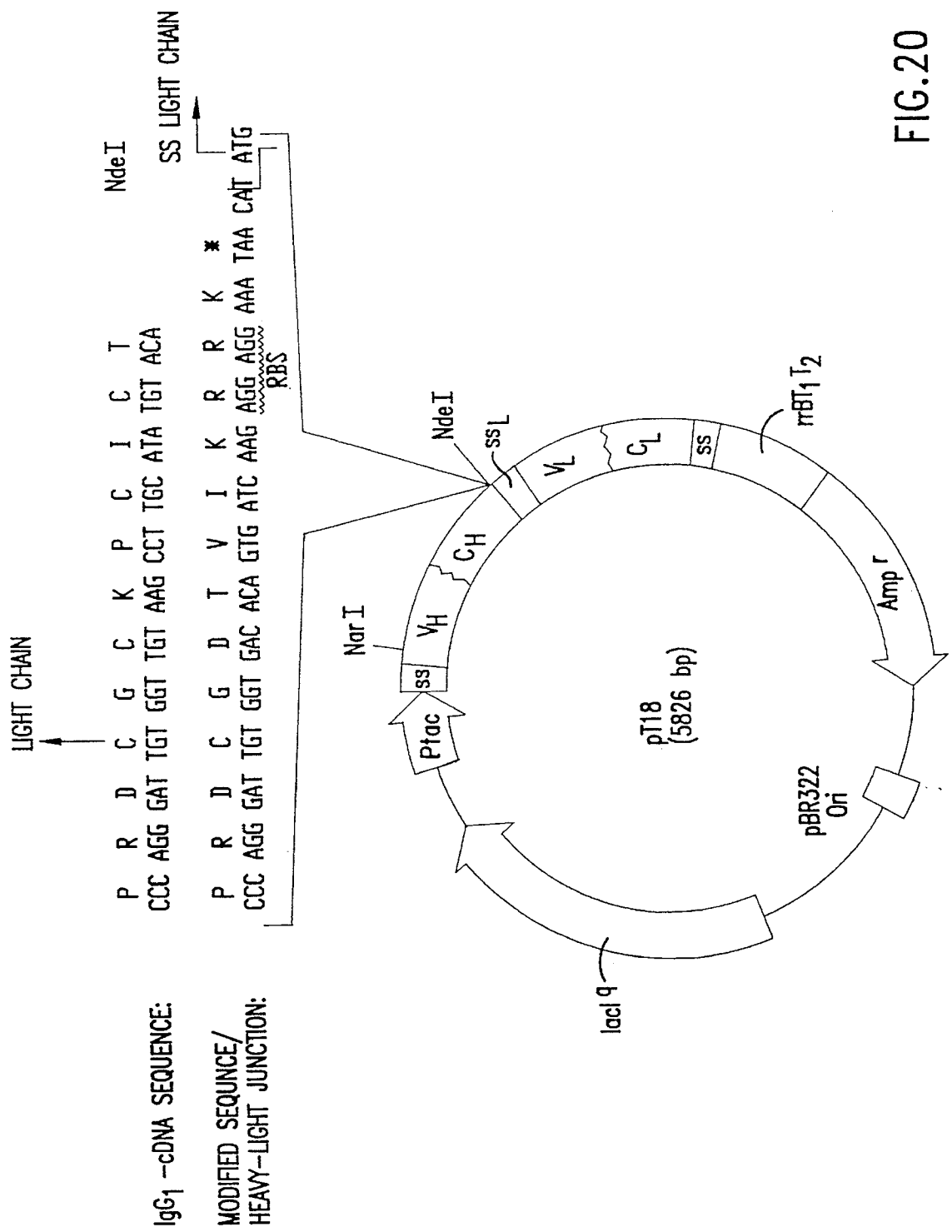
FIG. 20 is a diagram of plasmid pT18, which carries a subclone of the IgG1 heavy chain cDNA ($V_H$ and $CH_1$).

II. Cloning of the Heavy Chain cDNA Fragment Encoding the Variable and First Constant Domain of an Anti-2-Phenyloxazolone IgG1 Subclass Antibody The mRNA of the IgG1 subclass antibody was isolated from hybridoma cell clone NQ-17.4.1 (Kaartinen et al., *Nature* 304:320 (1983)). The first strand of the heavy chain cDNA was synthesized using oligo(dT) primer (Maniatis et al., 1982). The cDNA:mRNA hybrid was directly subjected to PCR amplification. The 5' end PCR-primer was identical with the sequence of the 5' end of the variable domain containing an EcoRI restriction site. The 3' end PCR primer was complementary to the heavy chain constant two domain coding region containing a HindIII restriction site. The amplified IgG1 heavy chain region cDNA was cloned as an EcoRI-HindIII restriction fragment into the pSP73 vector (Promega). The heavy chain cDNA was modified with PCR before cloning it into the *E. coli* expression vector. The very 3' end of the coding region of the heavy constant one domain was modified by changing the three cysteine residues involved in disulfide linkages with the other heavy chain in an intact IgG1 molecule (FIG. 20). In addition, a ribosome binding site sequence for the light chain translation and a NdeI restriction site used in the frame cloning with the light chain coding region were introduced in the modified 3' sequence of the heavy chain (FIG. 20). The modified heavy chain cDNA of the Ox IgG1 subclass was cloned into *E. coli* expression vector by replacing the NarI-NdeI restriction fragment of the heavy chain coding region in the Ox IgG3 subclass Fab-fragment expression vector with that of the modified IgG1 subclass cDNA clone. The *E. coli* expression vector of the Ox IgG1 subclass Fab-fragment was designated pTI8.

Only the heavy chains differ from each other in different IgG antibody subclasses. The hybridoma cell clones DHK-2,6 and NQ-17.4.1 produce identical light chains (kappa). The mRNA sequence for the light chain from NQ-17.4.1 clone has been published by Kaartinen et al., *Nature* 304:28 (1983)). Eventually, only IgG1 Fab has been used for Trichoderma expression studies, though IgG3 heavy chain cDNA exists in the early steps on the construction of the heavy chain expression vector (see Example 15).

All references cited herein are fully incorporated herein by reference. Having now fully described the invention, it will be understood by those with skill in the art that the scope may be performed within a wide and equivalent range of conditions, parameters and the like, without affecting the spirit or scope of the invention or any embodiment thereof.

What is claimed is:

1. A method for producing an immunoglobulin, wherein said method comprises the steps of:
 a. transforming a Trichoderma host cell with a recombinant construct encoding an immunoglobulin heavy chain or an immunologically active fragment thereof wherein the DNA encoding said immunoglobulin heavy chain or said fragment thereof is operably linked to DNA elements selected from the group consisting of Trichoderma and Aspergillus transcriptional regulatory elements;
 b. transforming said host cell with a recombinant construct encoding an immunoglobulin light chain or an immunologically active fragment thereof wherein the DNA encoding said immunoglobulin or said fragment thereof is operably linked to DNA elements selected from the group consisting of Trichodertna and Aspergillus transcriptional regulatory elements;
 c. culturing said host cell under conditions which express said heavy chain and said light chain; and
 d. recovering the immunoglobulin produced by said host cell of part c.

2. A method for producing an immunoglobulin, wherein said method comprises the steps of:
 a. transforming a first Trichoderma host cell with a first recombinant construct encoding an immunoglobulin heavy chain or an immunologically active fragment thereof wherein the DNA encoding said immunoglobulin heavy chain or said fragment thereof is operably linked to DNA elements selected from the group consisting of Trichoderma and Aspergillus transcriptional regulatory elements;
 b. transforming a second Trichoderma host cell with a second recombinant construct encoding an immunoglobulin light chain or an immunologically active fragment thereof wherein the DNA encoding said immunoglobulin light chain or said fragment thereof is operably linked to DNA elements selected from the group consisting of Trichoderma and Aspergillus transcriptional regulatory elements;
 c. culturing said first host cell and said second host cell under conditions which express said heavy chain and said light chain;
 d. recovering said immunoglobulin heavy chain or said immunologically active fragment thereof produced by said first host cell and said immunoglobulin light chain or said immunologically active fragment thereof produced by said second host cell; and
 e. incubating said heavy chain and said light chain under conditions which promote the reassociation of said heavy chain and said light chain into an immunologically active conformation.

3. The method of claim 1 or 2, wherein said recombinant construct encoding an immunoglobulin light chain or an immunologically active fragment thereof and said recombinant construct encoding an immunoglobulin heavy chain or an immunologically active fragment thereof are each operably linked to a nucleotide sequence encoding a Trichoderma or Aspergillis secretion signal.

4. A method for producing an immunoglobulin or immunologically active fragment thereof, wherein said method comprises:
 (A) expressing a gene encoding an immunoglobulin light chain or an immunologically active fragment thereof, and a gene encoding an immunoglobulin heavy chain or an immunologically active fragment thereof, in a Trichoderma host cell transformed with said genes, wherein said genes are operably linked to DNA elements selected from the group consisting of Trichoderma and Aspergillus transcriptional regulatory elements, and
 (B) producing an immunoglobulin that contains said heavy chain or said immunologically active fragment thereof and said light chain or said immunologically active fragment thereof.

5. The method of claim 4, wherein said DNA regulatory elements comprise Aspergillus sequences.

6. The method of claim 4, wherein said DNA regulatory elements are Trichoderma genomic sequences.

7. The method of any one of claims 4, 5, or 6, wherein said DNA regulatory elements are selected from the promoter and terminator regions of a gene selected from the group consisting of a gene that is expressed when said Trichoderma is grown on glucose and a cellulase gene.

8. The method of claim 7, wherein said cellulase gene is selected from the group consisting of the cbh1 gene, the chb2 gene, the egl1 gene and the egl2 gene.

9. The method of claim 8, wherein said DNA regulatory elements are the promoter and terminator regions of the cbh1 gene.

10. The method of claim 4, wherein said immunoglobulin or immunologically active fragment thereof comprises a Fab region.

11. The method of claim 4, wherein said immunoglobulin or immunologically active fragment thereof comprises a Fc region.

12. The method of any one of claims 1, 2, or 4, wherein said immunoglobulin light chain is an immunologically active fragment of said light chain.

13. The method of any one of claims 1, 2, or 4, wherein said light chain is a λ chain.

14. The method of anyone of claims 1, 2, and 4, wherein said light chain is a κ chain.

15. The method of any one of claims 1, 2, or 4, wherein said immunoglobulin heavy chain is an immunologically active fragment of said heavy chain.

16. The method of any one of claims 1, 2, or 4, wherein said immunoglobulin heavy chain is a μ chain.

17. The any one of claims 1, 2, or 4, wherein said immunoglobulin heavy chain is a γ chain.

18. The method any one of claims 1, 2, or 4, wherein said immunoglobulin heavy chain is an α chain.

19. The method any one of claims 1, 2, or 4, wherein said immunoglobulin heavy chain is a δ chain.

20. The method any one of claims 1, 2, or 4, wherein said immunoglobulin heavy chain is an ε chain.

21. A Trichodernm host cell transformed with
(1) a gene encoding an immunoglobulin light chain or an immunologically active fragment thereof, and a gene encoding an immunoglobulin heavy chain or an immunologically active fragment thereof,
wherein said genes encoding said heavy chain, and said light chain are operably linked to DNA elements selected from the group consisting of Trichoderma and Aspergillus transcriptional regulatory elements.

22. The host cell of claim 21, wherein said DNA elements comprise Aspergillus sequences.

23. The host cell of claim 21, wherein said DNA elements Trichaderma genomic sequences.

24. The host cell of any one of claims 21, 22, or 23, wherein said DNA elements are selected from the promoter and terminator regions of a gene selected from the group consisting of a gene that is expressed when said Trichoderma is grown on glucose and a cellulase gene.

25. The host cell of claim 24, wherein said cellulase gene is selected from the group consisting of the cbh1 gene, the chb2 gene, the egl1 gene and the egl2 gene.

26. The host cell of claim 25, wherein said DNA regulatory elements are the promoter and terminator regions of the cbh1 gene.

27. The host of claim 21, wherein said immunoglobulin light chain is an immunologically active fragment of said immunoglobulin light chain.

28. The host of claim 21, wherein said light chain is a λ chain.

29. The host of claim 21, wherein said light chain is a κ chain.

30. The host of claim 21, wherein said immunoglobulin heavy chain is an immunologically active fragment of said immunoglobulin heavy chain.

31. The host of claim 21, wherein said immunoglobulin heavy chain is a μ chain.

32. The host of claim 21, wherein said immunoglobulin heavy chain is a γ chain.

33. The host of claim 21, wherein said immunoglobulin heavy chain is an α chain.

34. The host of claim 21, wherein said immunoglobulin heavy chain is a δ chain.

35. The host of claim 21, wherein said immunoglobulin heavy chain is an ε chain.

36. The host of claim 21, wherein said fragment of said light chain comprises the variable region, and said fragment of said heavy chain comprises the variable region and wherein said variable region of said light chain is linked to said variable region of said heavy chain so as to form a single chain antibody.

37. Plasmid pEN304.

38. A Trichoderma host cell transformed with the plasmid of claim 37.

39. The Trichoderma host cell of claim 38, wherein said host cell possesses the Centraalbureau voor Schimmelcultures accession number 252.90.

40. A plasmid, wherein said plasmid is selected from the group consisting of pEN303, pEN305, pEN208, pEN209, pEN401, pEN402, pAJ201, and pAJ202.

41. A Trichoderma host cell transformed with a plasmid of claim 40.

42. *Trichoderma reesei* (pEN304/pEN209/RUT-C-30) which possesses the CBS accession number 287.91.

43. *Trichoderma reesei* (pEN304/pAJ202/RUT-C-30) which possesses the CBS accession number 288.91.

44. Plasmid pAJ202 in *Escherichia coli* possessing the accession number DSM 6584.

45. Plasmid pEN209 in *Escherichia coli* possessing the accession number DSM 6585.

46. Plasmid pEN304 in *Escherichia coli* possessing the accession number DSM 6586.

47. Plasmid pEN401 in *Escherichia coli* possessing the accession number DSM 6587.

48. Plasmid pEN402 in *Escherichia coli* possessing the accession number DSM 6588.

* * * * *